United States Patent
Campbell et al.

(10) Patent No.: US 12,417,540 B2
(45) Date of Patent: Sep. 16, 2025

(54) METHODS AND APPARATUS FOR IMAGING, ANALYSING IMAGES AND CLASSIFYING PRESUMED PROTEIN DEPOSITS IN THE RETINA

(71) Applicants: Melanie Crombie Williams Campbell, Waterloo (CA); Yunyi Qiu, Kitchener (CA); Peter Andrew Charles Neathway, Paris (CA)

(72) Inventors: Melanie Crombie Williams Campbell, Waterloo (CA); Yunyi Qiu, Kitchener (CA); Peter Andrew Charles Neathway, Paris (CA)

( * ) Notice: Subject to any disclaimer, the term of this patent is extended or adjusted under 35 U.S.C. 154(b) by 462 days.

(21) Appl. No.: 18/009,839

(22) PCT Filed: Jun. 14, 2021

(86) PCT No.: PCT/CA2021/050812
§ 371 (c)(1),
(2) Date: Dec. 12, 2022

(87) PCT Pub. No.: WO2021/248253
PCT Pub. Date: Dec. 16, 2021

(65) Prior Publication Data
US 2023/0222664 A1    Jul. 13, 2023

Related U.S. Application Data
(60) Provisional application No. 63/038,256, filed on Jun. 12, 2020.

(51) Int. Cl.
*G06T 7/00*    (2017.01)
*A61B 3/00*    (2006.01)
(Continued)

(52) U.S. Cl.
CPC .......... *G06T 7/0016* (2013.01); *A61B 3/0008* (2013.01); *A61B 3/12* (2013.01);
(Continued)

(58) Field of Classification Search
CPC ......... G06T 7/0016; G06T 2207/20084; G06T 2207/30041; G06T 2207/30204;
(Continued)

(56) References Cited

U.S. PATENT DOCUMENTS

| | | | |
|---|---|---|---|
| 8,097,253 B2 * | 1/2012 | Li .......................... | A61P 9/10 424/139.1 |
| 2010/0204973 A1 * | 8/2010 | Parkinson .............. | G16B 50/30 703/11 |

(Continued)

*Primary Examiner* — Mohammed A Hasan
(74) *Attorney, Agent, or Firm* — HILL & SCHUMACHER

(57) ABSTRACT

The present disclosure provides methods and an apparatus for imaging and analysing images of presumed protein deposits in the retina, retinal tissue or retinal structures and discloses methods differentiating or classifying these deposits and other optical signals from retinal structures into 1) whether they contain or do not contain classes, of proteins or protein deposits called amyloids or other proteins and/or protein deposits related to neurodegenerative eye and brain disease(s): 2) which type(s) of amyloid or other proteins or protein deposits they contain, as well as 3) whether the form and/or properties of the deposit are associated with a class of diseases or with one or another specific condition(s) (or disease(s)); whether or not this is a disease or class of disease associated with the retina or more generally with the nervous system, including the brain or 4) classified as associated with one or another level of severity of condition(s), or disease(s).

21 Claims, 33 Drawing Sheets

(51) Int. Cl.
    *A61B 3/12*       (2006.01)
    *A61B 5/00*       (2006.01)
    *G06V 10/22*     (2022.01)
    *G06V 10/60*     (2022.01)
    *G06V 10/764*   (2022.01)

(52) U.S. Cl.
    CPC .......... *A61B 5/4088* (2013.01); *G06V 10/225* (2022.01); *G06V 10/60* (2022.01); *G06V 10/764* (2022.01); *G06T 2207/20084* (2013.01); *G06T 2207/30041* (2013.01); *G06T 2207/30204* (2013.01); *G06V 2201/03* (2022.01)

(58) Field of Classification Search
    CPC . G06T 2207/10024; G06T 2207/20081; G06T 7/0012; A61B 3/0008; A61B 3/12; A61B 5/4088; G06V 10/225; G06V 10/60; G06V 10/764; G06V 2201/03
    USPC ........................................................ 351/206
    See application file for complete search history.

(56) References Cited

U.S. PATENT DOCUMENTS

2013/0208245 A1*   8/2013   Campbell ............ A61B 3/0025
                                                          351/246
2022/0007937 A1*   1/2022   Govari ................ A61F 9/00825

* cited by examiner

Fluorescence images

Deposit 1

Deposit 2

Deposit 3

Deposit 4

Pure 1

Pure 2

Linear diattenuation (LD)

AB-42 *1*

AB-42 *2*

Alpha-syn *1*

Alpha-syn *2*

Combination image

AB-42 *1*

AB-42 *2*

Alpha-syn *1*

Alpha-syn *2*

METHODS AND APPARATUS FOR IMAGING, ANALYSING IMAGES AND CLASSIFYING PRESUMED PROTEIN DEPOSITS IN THE RETINA

CROSS-REFERENCE TO RELATED PATENT APPLICATIONS

This patent application is a National Phase of PCT/CA2021/050812 filed on Jun. 14, 2021, and published on Dec. 16, 2021 as WO2021/050812, in English, which claims the priority benefit from, U.S. Provisional Patent Application No. 63/038,256 filed on 12th June 2020, the whole contents of which are incorporated herein by reference in their entireties.

FIELD

The present disclosure relates to methods and apparatus for imaging, analyzing images and classifying presumed protein deposits in the retina for detection and diagnosis of protein deposits in neurodegenerative disease(s) of the retina and brain, such as but not limited to Alzheimer's disease.

BACKGROUND

Current methods for diagnosing Alzheimer's disease and many other neurodegenerative diseases are primarily via clinical evaluation of symptoms. Other methods used are invasive, including assessment of amyloid beta (Aβ) and other substances in the cerebral spinal fluid, the blood or genetic markers, among others. Other methods of scanning the brain are expensive and not widely available, including brain scans via MRI and PET scanning, using molecules which bind to Aβ, tagged with radionucleotide markers. The presence of Aβ in neural tissue is recognized as indicative of Alzheimer's disease. There is a need for a readily available, objective, relatively inexpensive detection and diagnostic of neurodegenerative disease(s) of the retina and brain, such as but not limited to Alzheimer's disease, with the potential to allow longitudinal quantification of progression (or severity) of proteins found in the disease, which is sensitive and specific and would enable earlier and more accurate diagnosis. Differential detection of protein deposits in the neural tissue of the retina provides such an advantage.

Earlier and more precise differentiation and classification of proteins and protein deposits in the retina would lead both to a better understanding of condition and disease processes, a more precise knowledge of the particular condition(s) present and to earlier interventions.

Optical imaging of the retina is advantageous because it is relatively non-invasive and without the risk of radiation exposure. It has the potential to facilitate diagnosis of neurodegenerative disease(s) of the retina and brain and assessment of their severities. Optical imaging of the brain has been proposed but this is most suitable for imaging through the thinner skull of rodent models of the disease, rather than through the human skull.

It would be advantageous to provide an optical method of imaging in the eye which would provide a differential diagnosis of eye and brain diseases involving neurodegeneration and an assessment of their severity. Optical imaging in the eye has the advantage of scattering much less light than the brain with an optical window through the front of the eye, transparent to wavelengths in the visible and infrared. This allows the neural tissue at the rear of the eye, the neural retina, to be imaged. There is also an ongoing need to image the induction, the progression and the results of treatment of the proteins involved in neurodegenerative diseases in the eye and brain in humans and in animal models of these conditions. The methods disclosed herein will also allow for a way for differentiation of different conditions and an assessment of their severities.

SUMMARY

The present invention describes methods and apparatus for the classification of deposits in the retina into classes, firstly whether or not they contain amyloid protein and subsequently whether they contain a particular subtype of amyloid protein or other protein deposits related to neurodegenerative eye and brain disease(s). In a third classification, once the type(s) of amyloid protein present have been classified, the position, shape and other properties of the deposits singly or in combination can be used to classify and differentiate the likelihood that condition(s) or disease(s) are present. In a fourth classification, the severity of a condition(s) in the retina and, by inference a condition(s) in the brain can be differentiated and classified.

Thus, the methods and apparatus described are aimed at imaging and analysing images of presumed protein deposits in the retina, retinal tissue or retinal structures and discloses methods differentiating or classifying said deposits and other optical signals from retinal structures into 1) whether they contain or do not contain classes, of proteins or protein deposits called amyloids or other proteins and/or protein deposits related to neurodegenerative eye and brain disease(s); 2) which type(s) of amyloid or other proteins or protein deposits they contain, as well as 3) whether the form and/or properties of the deposit are associated with a class of diseases or with one or another specific condition(s) (or disease(s)); whether or not this is a disease or class of disease associated with the retina or more generally with the nervous system, including the brain or 4) classified as associated with one or another level of severity of condition(s) (or disease(s)).

Other properties of the deposits singly or in combination can be used to classify and differentiate the severity of the condition(s) or disease(s) present. The four classifications above are described as a branching tree when at each level there are at least two categories of classification. Moreover, the imaging and classification methods described can be generalized and used much more broadly to categorize deposits, retinal tissues or structures as containing more than one category of amyloid or other protein or protein deposit, whether there is more than one condition or disease present in either the retina or by inference the brain. And the severity of the more than one condition or disease present in the retina and/or the brain can also be differentiated and classified.

The methods and classification schemes described here could also be used to distinguish additional non amyloid proteins and/or protein deposits associated with additional conditions or diseases present in the retina or by inference in the brain. Properties used for classification and differentiation of proteins or protein deposits into the groups described above may include but are not limited to: interactions with polarised light, the distribution of intensities within an image taken with any type of light which makes the deposits visible; size and shape of said deposits, fractal dimensions of deposits, or other properties of the images of the deposit defined on average or spatially resolved across the deposit.

Either the differences within the images or a subset of images or differences in the images themselves of the retina may be classified into categories of conditions or diseases, either affecting only the retina and thus vision or it could be inferred from the identification of one or more proteins or protein deposits that these conditions or diseases are also affecting or likely to affect the brain and giving rise to either prodromal conditions (which precede disease or indicate disease or precede or indicate explicit multiple conditions or diseases of the brain.

An embodiment of the invention, requires the measurement of the optical properties of the protein deposits within the retina in such a way as to allow differentiation and/or classification of the deposits into the classes described above where these classes can be defined by the type of protein therein and/or the condition that the protein is associated with and/or the severity of said condition: firstly, whether the protein falls into a class of amyloid proteins which would stain positively to an amyloid specific protein stain (such as thioflavin) if such a stain were used. Secondly, within the amyloid deposits, (or non amyloid deposits) which protein has high likelihood of being present (influenced by other information available on potential conditions, the position of the deposit in the retina and/or the optical and/or morphological and/or fractal properties of the deposits within the retina either measured directly or imaged as part of a retinal image.

Either the properties within both the raw and/or the calculated images of the retina (including the pixel-by-pixel representation of the Mueller or the Jones matrices), or a subset of images or properties in the images may be classified into categories of amyloid positive protein or not, type(s) of protein(s), type(s) of condition(s) or disease(s) and/or severity of condition(s) or disease(s). Or the images may be combined in any way to further analyse the properties of the structures and potential protein deposits. These protein deposits either affect only the retina and thus vision or it could be inferred from the identification of one or more proteins or protein deposits in the retina that these condition(s) or disease(s) are also affecting the brain and giving rise to either prodromal condition(s) (which precede disease or indicate disease or precede or indicate explicit multiple conditions or diseases of the brain) or to diseases. The intent is to determine properties of the protein(s) or protein deposit(s), whether the form of a given protein deposit or group of protein deposits is associated with a class of diseases or with one or another specific condition(s) (or disease(s)), whether or not this disease or class of disease is associated with the retina or more generally with the nervous system, including the brain and the severity of said condition or disease. One can also classify proteins or protein deposits as associated with one or another level of severity of condition(s) (or disease(s)).

In various embodiments, properties used for differentiation and classification of proteins and/or protein deposits into the groups described above may include but are not limited to the following: interactions with polarised light, the distribution of intensities within an image taken with any type of incident light which makes the deposits visible; size and shape of said deposits, fractal dimensions or spectra of deposits, or other optical properties of either the deposits or of the images taken.

Herein, there is also disclosed the classification schemes which use the images obtained, or features extracted from the images to perform a classification of the protein(s) or protein deposit(s) present, to perform one or more of the following classifications: firstly broadly as to whether proteins or deposits containing amyloid proteins are present in the retina, then what specific type(s) of protein or protein deposit(s) are present, what disease or conditions are consistent with the protein(s) or protein deposits or distribution of proteins or protein deposit(s) present and then the severity of the pathology, the disease(s) or disorder(s) present. Besides the machine learning approaches outlined herein, other known classification schemes within the broad definition of machine learning and artificial intelligence can also be used to perform said classification. We use machine learning methods to differentiate and classify protein(s) and protein deposit(s) known as non-parametric discriminant analysis in SAS, including linear discriminant analysis, Random forrest, referred to as "bagged trees" in Matlab, supporting vector machines and Convolutional Neural Networks using Resnet 101.

The present disclosure provides a method for detecting, imaging, differentiating and classifying proteins or protein deposits in the retina of the eye for detecting neurodegenerative diseases of the retina and/or of the brain or their prodromal stages, comprising the steps of:

a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;

b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and c) differentiating and classifying the markers detected at each position in the retina by using their measured morphology, including size, shape, fractal properties of the proteins or protein deposits, or characterizing a strength of a marker(s) of protein or protein deposits or strength of signal(s) coming from any interaction with light, separately for each protein(s) or protein deposit(s) so as to determine if the properties including position and morphology, markers and or interaction with light, of said protein(s) or protein deposit(s) are consistent with said protein(s) or protein deposit(s) found in a particular disease or condition which occurs in either the retina or the brain or both where properties of protein(s) and or protein deposit(s) consistent with a particular disease or condition have been determined from ex vivo tissue of those with said disease or condition, from animal models or from previous measurements of those with known conditions.

The present disclosure provides a method for detecting, imaging, differentiating and classifying proteins or protein deposits in the retina of the eye for detecting neurodegenerative diseases of the retina and/or of the brain or their prodromal stages, comprising the steps of:

a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;

b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and c) differentiating and classifying the markers detected at each position in the retina by using the properties of the protein(s) or protein deposit(s) of the morphology, including size, shape, and fractal properties of the protein(s) or protein deposit(s) or characterizing a strength of a marker(s) of protein(s) or protein deposit(s) or strength of any measured signal(s) coming from any interaction with light so as to determine if the proteins or protein deposits belong to a class known as amyloid or thioflavin positive deposits which would stain with thioflavin and fluoresce or are proteins or protein deposits which would not stain with thioflavin and would not fluoresce known as thioflavin negative deposits, where said classification compares with results previously obtained in ex vivo tissue where the combination of properties, known as markers, corresponding to a thioflavin positive deposit; has been determined using thioflavin staining as a gold standard.

The present disclosure provides a method for detecting, imaging, differentiating and classifying proteins or protein deposits in the retina of the eye for detecting neurodegenerative diseases of the retina and/or of the brain or their prodromal stages, comprising the steps of:

a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;

b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and c) differentiating and classifying the markers detected at each position in the retina by using their measured morphology, including size, shape, fractal properties of the proteins or protein deposits; or characterizing a strength of a marker(s) of protein(s) or protein deposit(s) or strength of signal(s) coming from any interaction with light so as to determine if the areas detected contain a particular protein type, where the properties measured are compared with the properties previously determined for pure proteins or pure protein deposits.

The present disclosure provides a method for detecting, imaging, differentiating and classifying proteins or protein deposits in the retina of the eye for detecting neurodegenerative diseases of the retina and/or of the brain or their prodromal stages, comprising the steps of:

a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;

b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and c) differentiating and classifying the markers detected at each position in the retina by using their measured morphology, including size, shape, fractal properties of the proteins or protein deposits; or characterizing a strength of a marker(s) of protein(s) or protein deposit(s) or strength of signal(s) coming from any interaction with light for each protein type associated with a neurodegenerative disease where said neurodegenerative disease diagnosis is already known, or the identity of disease and its severity can be deduced simultaneously from the properties measured and compare to those properties previously identified as markers of severity of the given neurodegenerative disease including one or more of protein deposit numbers, total area of the retina covered by protein deposits, volume or thickness of protein deposits, strength of signal(s) coming from any interaction of proteins or protein deposits with light, morphology of deposits known to change with severity, particular locations of protein deposits in the retina and deduce the severity of the disease in the retinal and by inference its severity in the brain.

The present disclosure provides a method for detecting, imaging, differentiating and classifying proteins or protein deposits in the retina of the eye for detecting neurodegenerative diseases of the retina and/or of the brain or their prodromal stages, comprising the steps of:

a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;

b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and c) differentiating and classifying the markers detected at each position in the retina by using the properties of the protein(s) or protein deposit(s) of the morphology, including size, shape, and fractal properties of the protein(s) or protein deposit(s) or characterizing a strength of a marker(s) of protein(s) or protein deposit(s) or strength of any measured signal(s) coming from any interaction with light so as to determine if the proteins or protein deposits belong to a class known as amyloid or thioflavin positive deposits which would stain with thioflavin and fluoresce or are proteins or protein deposits which would not stain with thioflavin called and would not fluoresce known as thioflavin negative deposits, where said classification compares with results previously obtained in ex vivo tissue where the combination of properties corresponding to a thioflavin positive deposit, known as markers, has been determined using thioflavin staining as a gold standard.

A further understanding of the functional and advantageous aspects of the invention can be realized by reference to the following detailed description and accompanying drawings.

BRIEF DESCRIPTION OF THE DRAWINGS

Embodiments of the present system and method will now be described, by way of example only, with reference to the drawings, in which.

Drusen (11), associated with the retinal pigment epithelium (10) and containing amyloid deposits, are found in association with age related macular degeneration, a neurodegenerative retinal disease. In this disease, amyloid deposits are found in the posterior retinal layers 10-11, and also in association with the photoreceptors (9). In addition, there are several en face layers of blood vessels near the anterior surface of the retina and deeper in the retina. Amyloid deposits have been found within these blood vessels by the inventors and others. Subtypes of the deposits found by us within these vessels correlate with the severity of cerebral amyloid angiopathy in the blood vessels of the brain.

Figure 22:
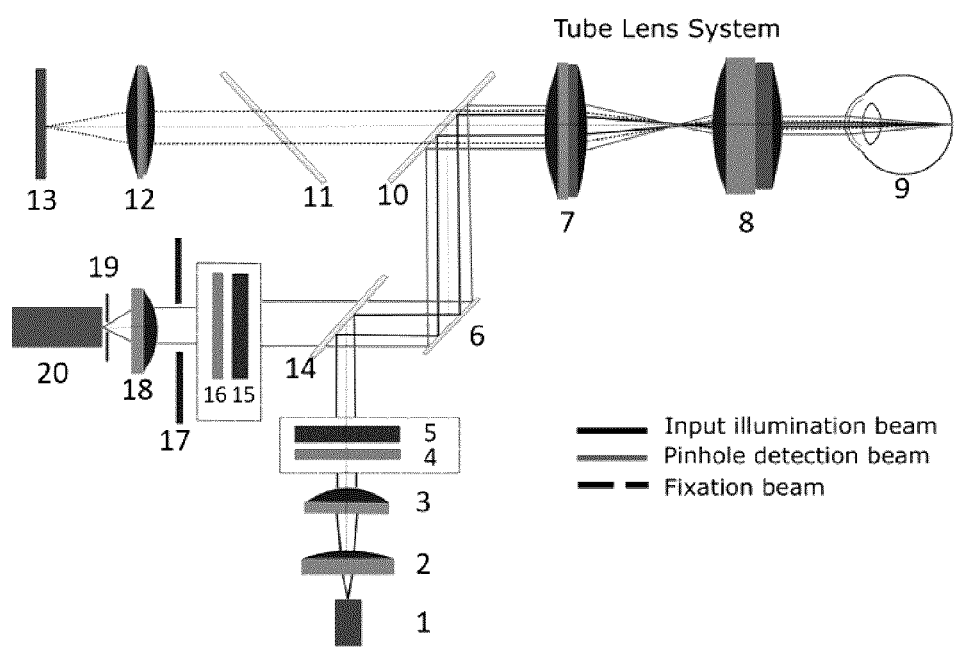

FIG. 22 is a schematic representation of a preferred implementation of a polarimetry system for imaging the retina to detect neurodegenerative disease(s) of the retina and brain, such as but not limited to Alzheimer's disease.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the phrase "differentiating and classifying the markers" means determining the specific morphological properties, interactions with light, prevalence and locations that each protein(s) and or protein deposit(s) possess. From these initially measured properties, the measured protein(s) and protein deposit(s) can placed (classified) into some or all of the following classes: 1) whether they contain or do not proteins or protein deposits called amyloids; 2) which type(s) of amyloid or other proteins or protein deposits they contain; 3) whether the form and/or properties of the deposit are associated with a class of diseases or with one or another specific condition(s) (or disease(s)); and whether or not this is a disease or class of disease is associated with the retina or more generally with the nervous system, including the brain or 4) classified as associated with one or another level of severity of condition(s) (or disease(s)). Other properties of the deposits singly or in combination can be used to classify and differentiate the overall severity of the condition(s) or disease(s) present. When this is complete, proteins and or protein deposits that fall into different classes have been differentiated one from the other. Machine learning and/or artificial intelligence algorithms can be used to assist in these classifications.

As used herein, the term "exemplary" means "serving as an example, instance, or illustration," and should not be construed as preferred or advantageous over other configurations disclosed herein.

As used herein, the word "retina" refers to the retina of the eye of mammals and all its known tissue layers or structures, including associated vessels.

As used herein the word "proteins" refers to one or more type of protein detected in the retina that are not in the form of a protein deposit, and as used herein the phrase "protein deposits" refers to one or more proteins and/or protein(s) mixed with components of cells in the form of a deposit or a precursor to a deposit.

As used herein, the phrase "en face" refers to the view of the retina if you are looking towards it from the direction of the crystalline lens, that is looking in the same direction as the incoming light. An observer would see the two-dimensional anterior surface and if images are taken below that, other 2D layers of retinal cells.

As used herein, an object that needs to be described by "fractal properties" is one that is too irregular to be easily described by traditional, simple geometric shapes. A fractal description has a Hausdorff dimension, a measure of roughness, or of complexity of texture. In the multifractal spectrum, the Hausdorff dimension is plotted against the Holder exponent. This exponent describes different amounts and types of regularity, present in the image, each with a different Holder exponent. Images with similar multifractal spectra have similar appearances in terms of the texture and the regularity of their surfaces. Thus, multifractal spectra are a measure of morphology of the image st multiple scales.

As used herein, the phrase "wide field imaging" means imaging a field normally imaged in traditional clinical en face imaging of the back of the eye, in this usage at least 10 degrees by 10 degrees en face image or a larger en face image or a three-dimensional image where the en face dimension is at least 10 degrees by 10 degrees. In the inventors' preferred implementation, classifying severity accurately would normally require a larger field than this minimum.

As used herein, the phrase "marker" is intended to indicate a subset of biomarkers. In the official National Institutes of Health definition, a biomarker is: "a characteristic that is objectively measured and evaluated as an indicator of normal biologic processes," or "pathogenic processes." The pathogenic process(s) that is evaluated here is the presence of neurodegenerative disease(s) of the eye or brain or of prodromal changes associated with said neurodegenerative disease(s), including the severity or stage of such changes or disease(s). The biomarker(s) identified as associated with or indicators of neurodegenerative disease(s), prodromal changes and severity are protein(s) and or protein deposit(s) and their specific morphological properties, interactions with light, prevalence and location and alterations of images taken in specific illumination and detection configurations.

As used herein, the term morphology describes the size, shape, structure and form of the protein(s) and protein deposit(s), including their fractal properties. The term refers to the general aspects of form and arrangement of the parts.

As used herein, the phrase "performing an A scan" is understood to mean that during OCT of the retina, an A-scan is an axial scan, representing reflected optical amplitude along the axis of light propagation, through the layers of the retina.

As used herein, the phrase "performing a B scan" is understood to mean that during OCT of the retina, a B-scan refers to a cross-sectional image where one axis of the image is an A scan and the amplitudes of reflections are represented in a gray scale or a false-color scale.

As used herein, the phrase "performing a C scan" is understood to mean that during OCT of the retina, a C-scan refers to a section across structures at an equal optical delay which in the retina corresponds to the coronal section, which is often modified to produce a C scan from a dataset which is a cross section parallel to the retina vitreal surface.

As used herein, the phrase "thioflavin positive deposit(s)" means proteins or protein deposit(s) which belong to a class of proteins known as amyloids which when stained with thioflavin and excited in shorter wavelengths emit fluorescent light at a longer wavelength, becoming visible against the surrounding tissue. As used herein "thioflavin negative deposit(s)" are proteins or protein deposits which would not fluoresce when stained with thioflavin.

As used herein, the phrases "Using adaptive optics" or "applying adaptive optics correction to light focused" refers to the correction of the wavefront of light ingoing incident on the retina and the further correction of the wavefront reflected outgoing from the retina. The ingoing correction produces an image of a point on the retina which is much smaller laterally and in depth than before the wavefront correction. The lateral resolution is then improved so that objects closer together (and perpendicular to the direction of light) can be resolved. The depth resolution is also improved in some imaging methods by the correction of the ingoing wavefront or by the correction of the outgoing wavefronts in others or by the correction of both. Improved depth resolution means that two objects at a smaller separation along the direction of light propagation can be resolved.

As used herein, the phrase "small point spread function on the retina" relates to approaching the smallest point spread function on the retina which is produced by diffraction of light from a point source by the pupil. When adaptive optics correction is perfect, the smallest is approached.

As used herein, reference to "fractal properties" refers to objects in which their dimensional properties are too irregular to be easily described by traditional, simple geometric shapes. It has a Hausdorff dimension, a measure of roughness, which is a fractal dimension which is a ratio providing a measure of complexity of texture. In the multifractal spectrum, the Hausdorff dimension is plotted against the Hölder exponent, which describes different types of regularity, present in the image, each with a different Hölder exponent. Images with similar multifractal spectra have similar appearances in terms of the texture and the regularity of their surfaces. Thus, multifractal spetra are a measure of morphology of the image.

The following examples are presented to enable those skilled in the art to understand and to practice embodiments of the present disclosure. They should not be considered as a limitation on the scope of the present embodiments, but merely as being illustrative and representative thereof.

The specific embodiments described below have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The present inventors and others have previously found amyloid deposits (presumed to be amyloid beta) in the retina in association with Alzheimer's disease. the inventors, polarimetry patent (United States Patent No. S914,9184, which is incorporated herein by reference in its entirety) concentrated on using optical imaging of and the properties of images of amyloid deposits in the retina of the eye to indicate the presence of amyloid deposits in the brain and the severity of those deposits. It included methods for imaging, apparatus and methods for determining the severity of amyloid deposits in the retina so as to predict the severity of amyloid in the brain, particularly related to Alzheimer's disease (AD). One important outcome was the specifying the presence of amyloid protein, assumed to be amyloid beta, whose presence is a minimum pre-condition to the diagnosis of Alzheimer's disease both early or prodromal disease and later severity stages. Also in the prior patents, it was stated that the methods described could be applied to imaging deposits in the posterior retina for the diagnosis of age-related macular degeneration (AMD). It was also described that such methods could be extended to other proteins and neurodegenerative diseases.

One of the inventors (Campbell) had previously shown and patented that the severity of amyloid deposits in the brain in association with Alzheimer's disease or the severity of Alzheimer's disease, a condition of the brain, overall could be predicted by the numbers and/or properties of amyloid deposits in the retina. The present inventors suggest that this will also be true of the strength, numbers or other properties of protein deposits in retinal tissue, including but not limited to amyloid deposits assumed to contain amyloid beta in Alzheimer's disease, signals of proteins in tissue or in retinal structures in relation to other neurodegenerative diseases of the brain.

To date the inventors have used thioflavin S as a gold standard marker of amyloid deposits in the post-mortem retina. Thioflavin (s or t), used in the past as a marker of amyloid beta, produces diffuse fluorescence throughout the retina and a particular stronger signature due to thioflavin combining with amyloid. However, it is invasive and not normally used in living tissue. Curcumin, another fluorescent marker of amyloid protein, can be used in the living organism (including humans) but requires ingestion over a prolonged period of time, with side effects and Campbell's group has found that it is persistent in the tissue for a prolonged period when used in animals. Thus, imaging with polarized light or other non-invasive imaging as described herein is preferable to using available fluorescent dyes.

In the following the inventors describe the use of machine learning methods to differentiate and classify protein(s) and protein deposit(s) known as non-parametric discriminant analysis in SAS, including linear discriminant analysis, Random forrest, referred to as "bagged trees" in Matlab and Convolutional Neural Networks using Resnet 101. Convolutional neural networks have the advantage of allowing optical images taken of the retina to be used directly in the programs. However, any other appropriate machine learning or artificial intelligence method could be used by one skilled in the art. Methods which belong to a field of methods known as machine learning which in turn is a sub field of artificial intelligence are in particular used to classify and differentiate the polarimetry properties defined across the visible candidate deposits in the retina which allow them to be differentiated and classified: Other artificial intelligence methods could also be used by one skilled in the art.

Figure 1:
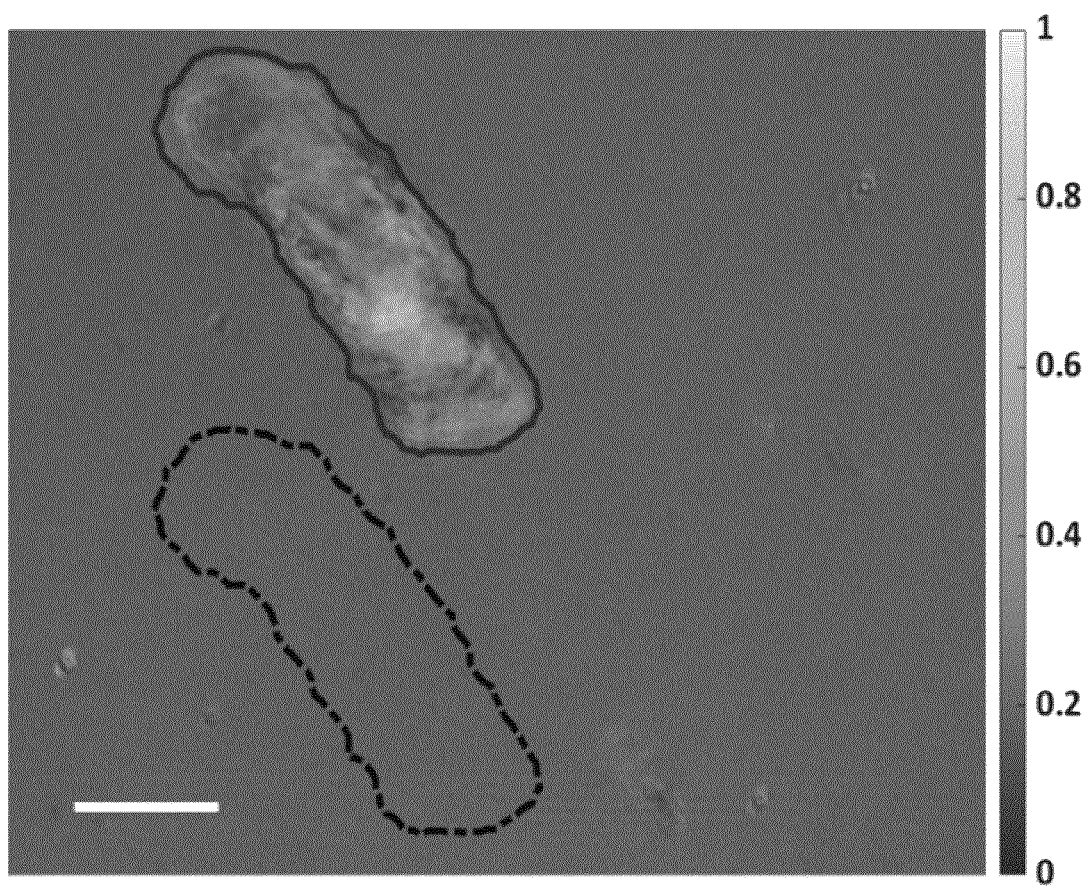
FIG. 1 shows an example of the retinal oversampling method disclosed herein. In the linear anisotropy image of a polarimetric positive deposit, a region with the same shape (dashed line) as the deposit (solid line) with no fluorescence signal. The area inside the dashed line is used as a fluorescence negative sample. Scale bar (white line is 20μ (microns)).
Figure 2A:
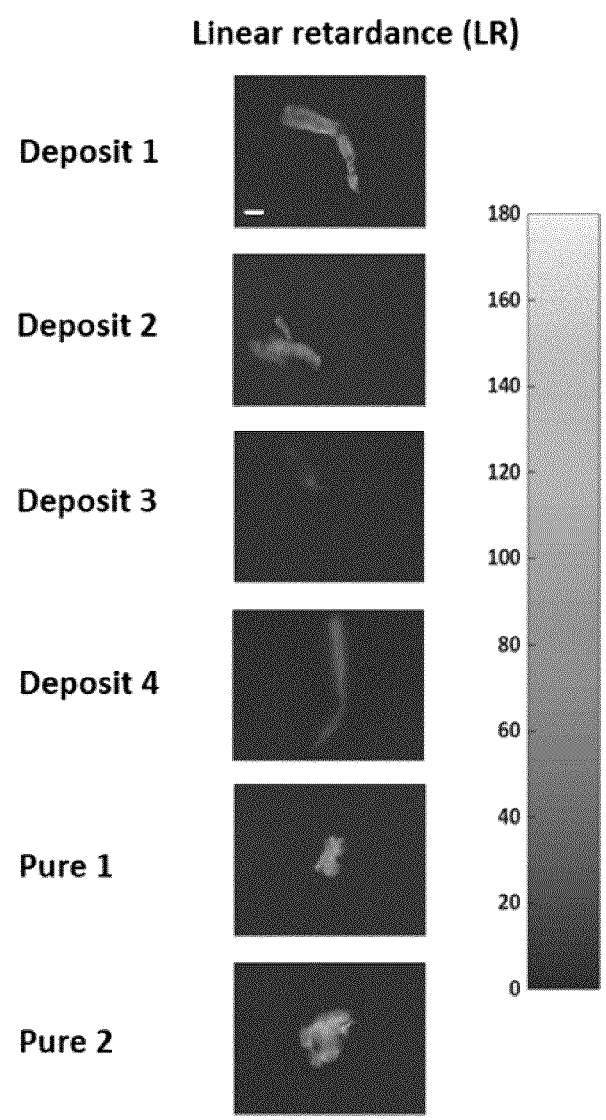
FIG. 2A shows linear retardance (LR) images of four retinal deposits, labelled 1 to 4, and two (2) of pure Aβ-42 protein deposits. The range of LR: is from 0° to 180°. The scale bar in the top image is 20μ and also applies to FIGS. 2B and 2C.
Figure 2B:
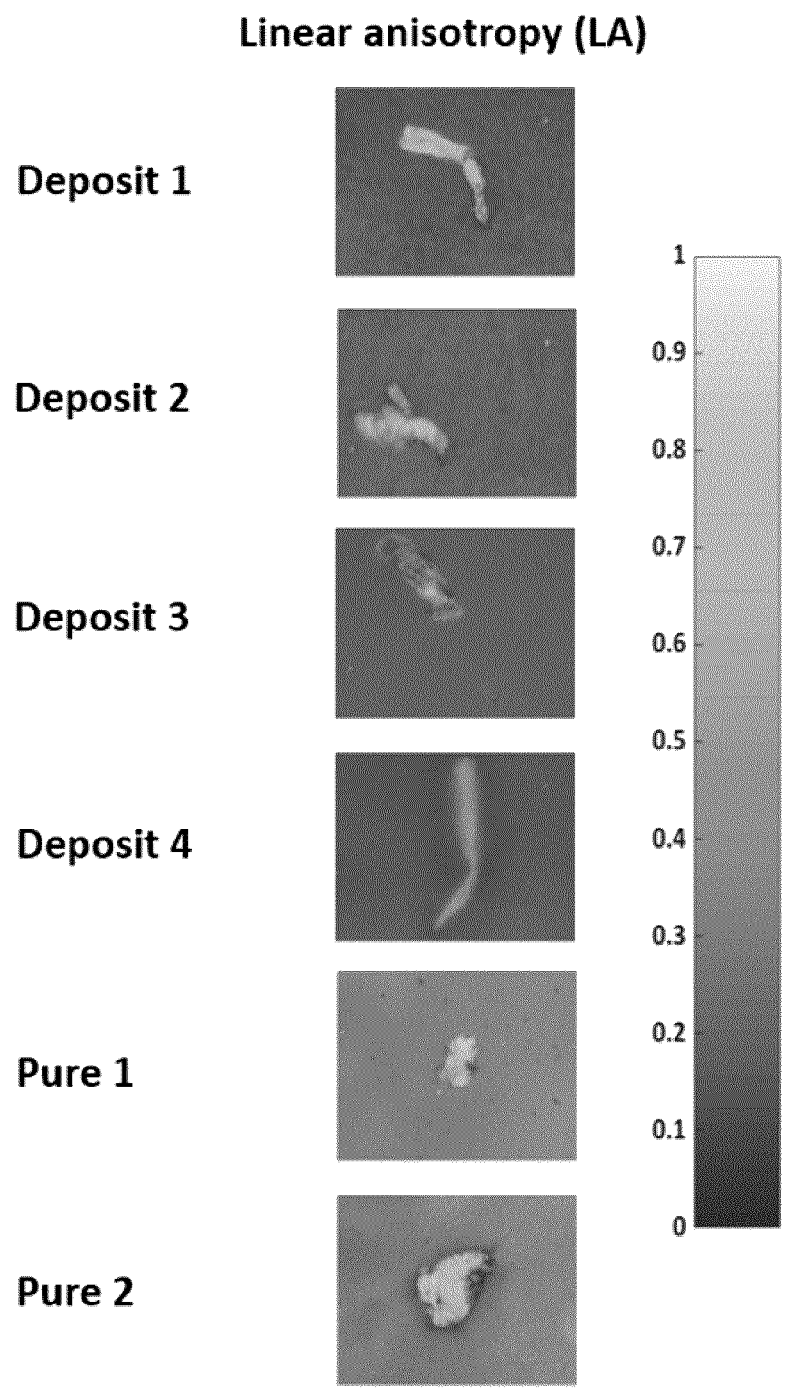
FIG. 2B shows linear anisotropy (LA) images of four retinal deposits, labelled 1 to 4 and two of pure Aβ-42 protein deposits. The range of LA is from 0 to 1.
Figure 2C:
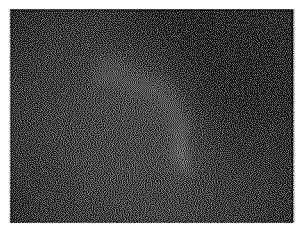
FIG. 2C shows fluorescence images of four retinal deposits, labelled 1 to 4 (images 1 and 2 have fluorescence signals while images 3 and 4 do not) and two of pure Aβ-42 protein deposits which have fluorescence signals.
Figure 2C:
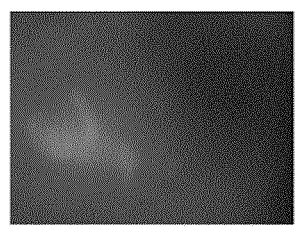
Figure 2C:
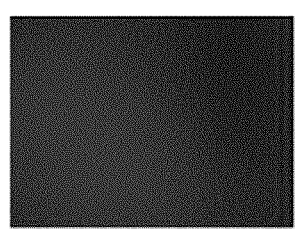
Figure 2C:
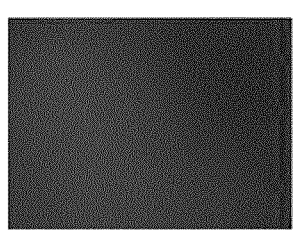
Figure 2C:
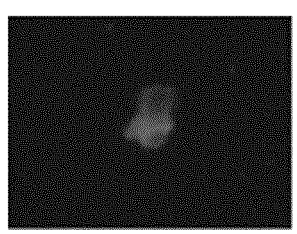
Figure 2C:
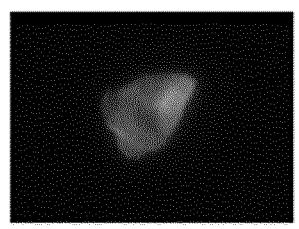
Figure 3A:
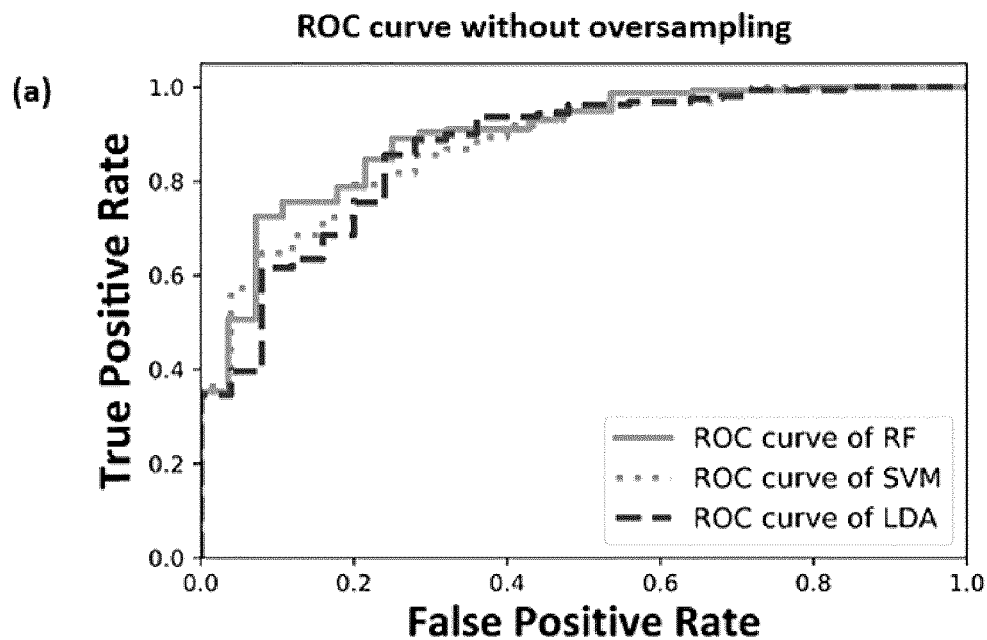
FIG. 3A shows Receiver Operating Characteristic (ROC) curves for fluorescence signal prediction by the three machine learning algorithms using a sampling strategy without oversampling. True positive rate is sensitivity and false positive rate is 1-specificity. Machine learning algorithms used for signal prediction are random Forrest (RF), Supporting vector machine (SVM) and linear discriminant analysis (LDA).
Figure 3B:
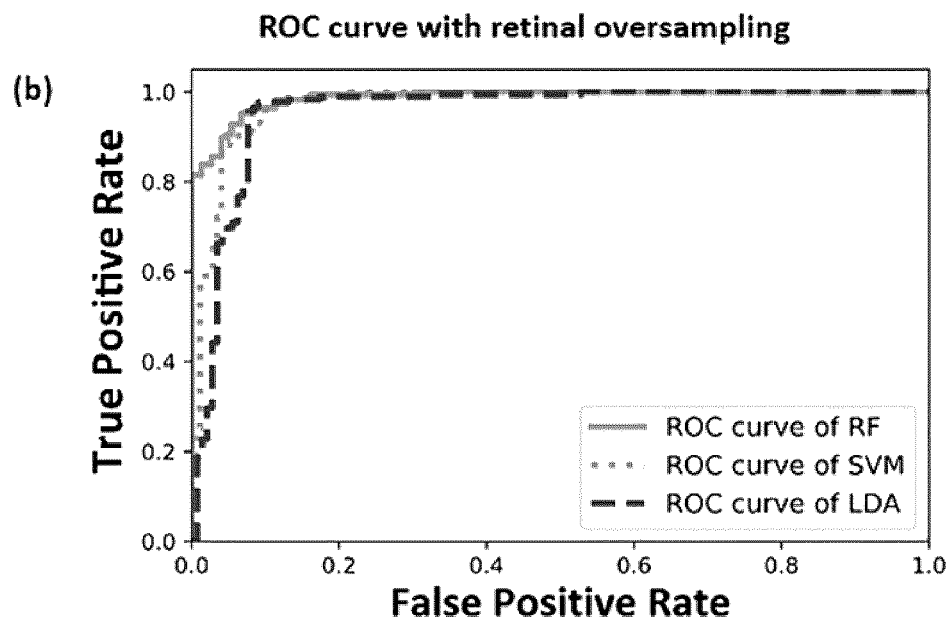
FIG. 3B shows Receiver Operating Characteristic (ROC) curves for fluorescence signal prediction by the three machine learning algorithms using a sampling strategy with retinal oversampling. True positive rate is sensitivity and false positive rate is 1-specificity. Machine learning algorithms are random Forrest (RF), Supporting vector machine (SVM) and linear discriminant analysis (LDA).
Figure 3C:
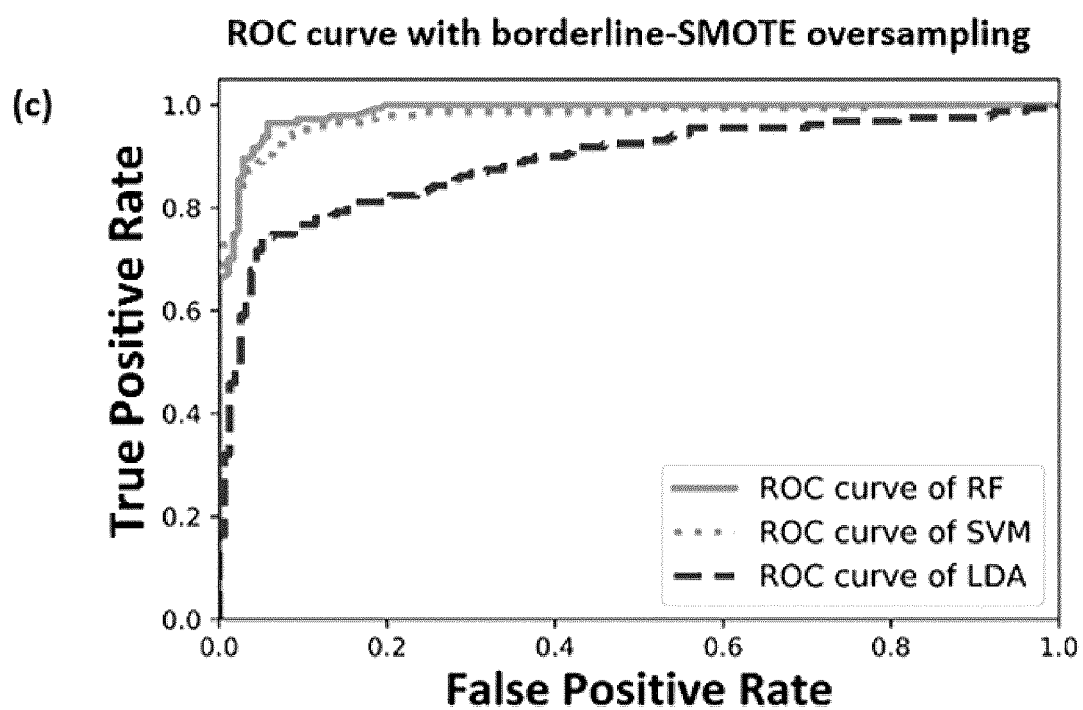
FIG. 3C shows Receiver operating characteristic (ROC) curves for fluorescence signal prediction by the three machine learning algorithms using a borderline SMOTE (Synthetic Minority Over-sampling Technique) for oversampling, a commonly used algorithm in machine learning to generate synthetic samples in the dataset with fewest samples. True positive rate is sensitivity and false positive rate is 1-specificity. Machine learning algorithms are random Forrest (RF), Supporting vector machine (SVM) and linear discriminant analysis (LDA).

Inventor the inventors had previously shown that, in the inventors' hands, imaging with polarized light and the consideration of the interactions of the polarized light with the retinal tissue (known as polarimetry) differentiated amyloid protein deposits from the surrounding retina with high accuracy (see FIG. 1). Herein the present inventors use classification methods which belong to a field of methods known as machine learning which in turn is a sub field of artificial intelligence to classify and differentiate the polarimetry properties defined across the visible candidate deposits in the retina which predict those that are thioflavin positive with high accuracy. Thioflavin is a gold standard for identifying amyloid proteins but, because of toxicity is not used in living tissue.

Thus, the inventors' differentiation of thioflavin positive deposits without the use of a dye is an important step to identifying, classifying and differentiating the proteins and protein deposits present in the retina (FIGS. 1 to 6). The contrast of a thioflavin positive deposit against the background retina can be seen in polarimetric images without a dye (FIG. 1). The present inventors used polarimetric properties which can be measured, to differentiate or distinguish between those that had thioflavin signals and were polarization positive and a small percentage of deposits that were thioflavin negative but polarization positive. Examples of two deposits which were thioflavin positive and two that were not are given in FIG. 2C. FIGS. 2A and 2B demonstrate the presence of fluorescence signals in both groups, albeit weaker in the thioflavin negative deposits than in the thioflavin positive deposits. In the classification of the thioflavin positive deposits compared to the thioflavin negative deposits, three different machine learning algorithms were used: random Forrest (RF), Supporting vector machine (SVM) and linear discriminant analysis (LDA) (FIGS. 3A, 3B, and 3C). Accuracy of classification improved to greater than 90% for all three methods with the inventors' retinal oversampling strategy (FIG. 3B). SMOTE a well-known approach (FIG. 3C) was also tested to account for the small number of thioflavin negative, polarization positive samples.

Figure 4:
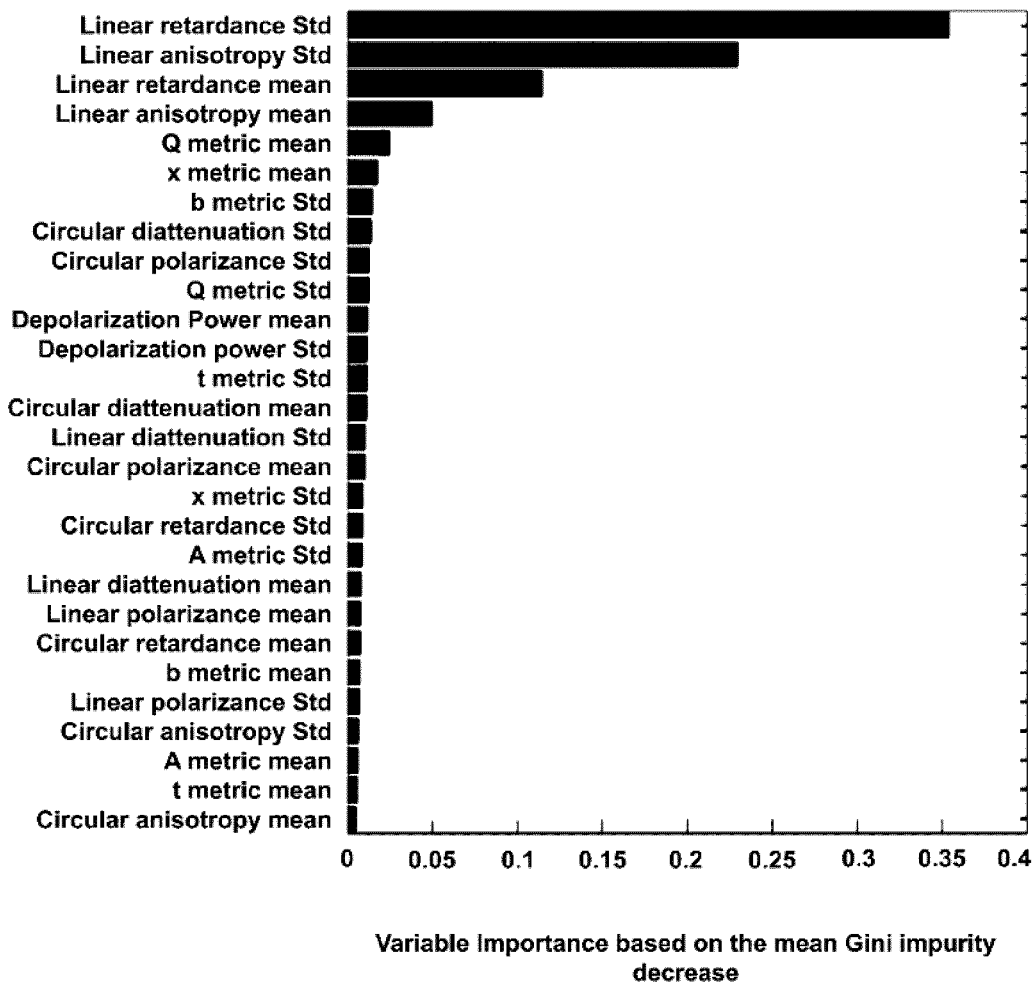
FIG. 4 shows the variable importance of 28 polarimetric properties listed on the left-hand vertical axis as feature inputs (mean and standard deviation of 14 polarimetric properties) from random Forrest analysis with retinal oversampling. The sum of the variable importance of all features is 1. Variable importance is based on the mean Gini impurity decrease.
Figure 5:
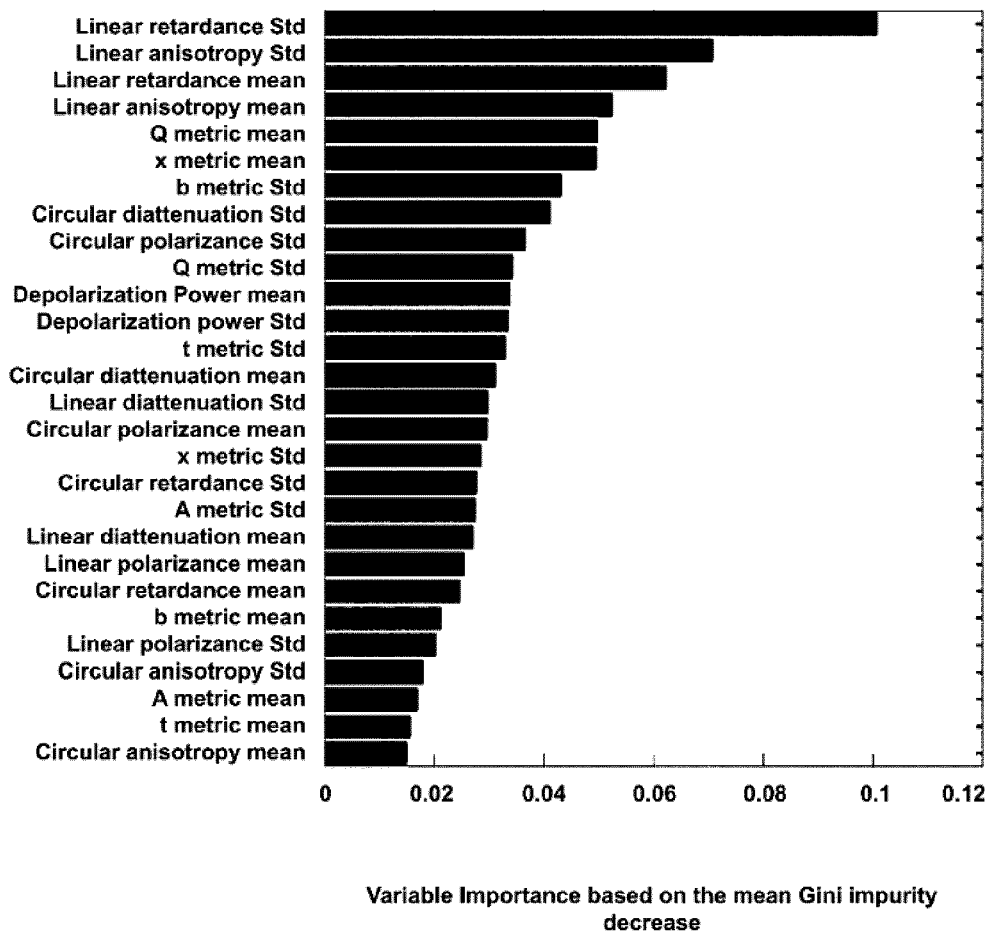
FIG. 5 shows the variable importance of 28 feature inputs (mean and standard deviation of 14 polarimetric properties) listed on the left-hand vertical axis for Random Forrest analysis with borderline-SMOTE oversampling. The sum of the variable importance of all features is 1. Variable importance is based on the mean Gini impurity decrease.
Figure 6A:
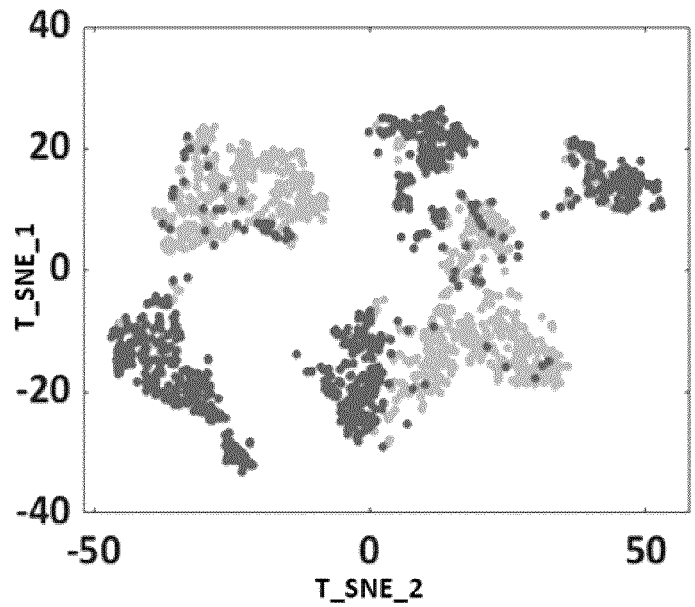
FIG. 6A shows two-dimensional t-distributed stochastic neighbor embedding (t-SNE) visualization of the polarization properties of the fluorescent positive and fluorescent negative datasets from the retinal oversampling method with a perplexity value of 30. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6B:
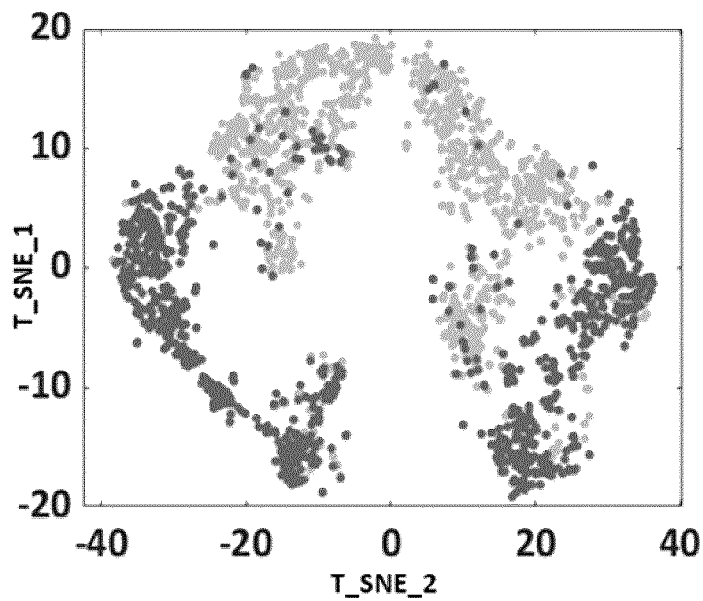
FIG. 6B shows two-dimensional t-distributed stochastic neighbor embedding (t-SNE) visualization of the polarization properties of the fluorescent positive and fluorescent negative datasets from the retinal oversampling method with a perplexity value of 50. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6C:
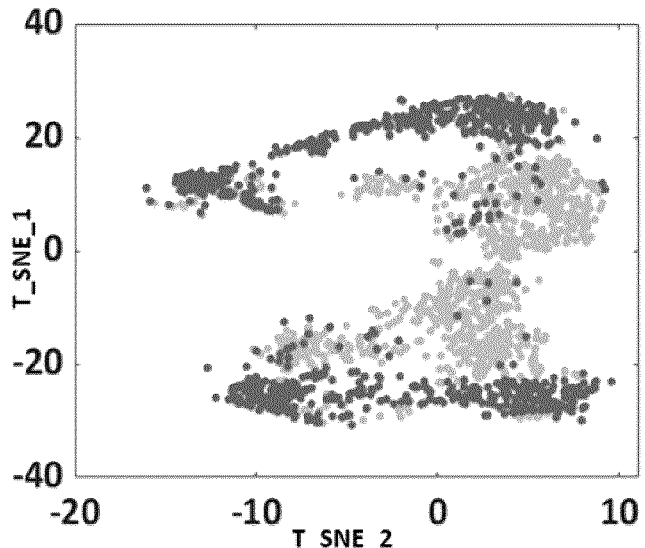
FIG. 6C shows two-dimensional t-distributed stochastic neighbor embedding (t-SNE) visualization of the polarization properties of the fluorescent positive and fluorescent negative datasets from the retinal oversampling method with a perplexity value of 80. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6D:
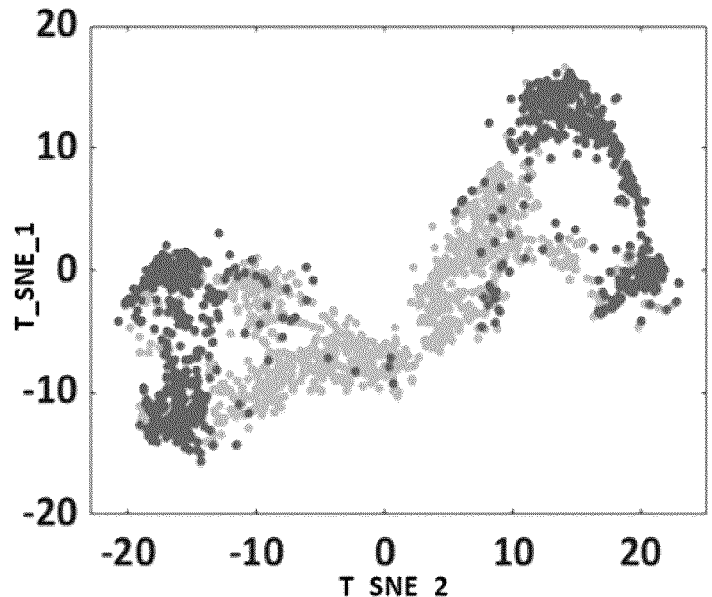
FIG. 6D shows two-dimensional t-distributed stochastic neighbor embedding (t-SNE) visualization of the polarization properties of the fluorescent positive and fluorescent negative datasets from the retinal oversampling method with a perplexity value of 100. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6E:
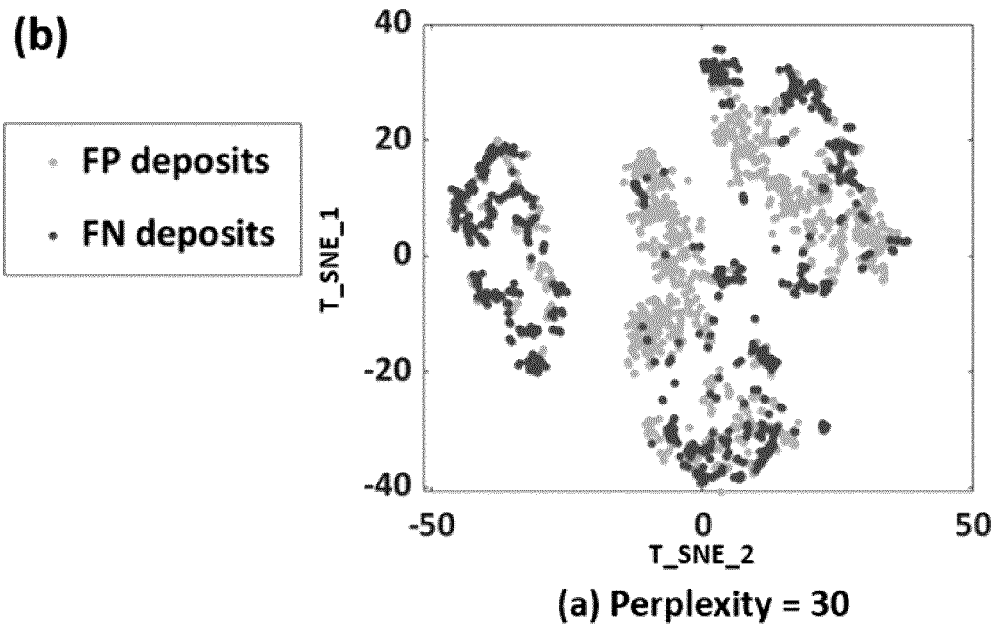
FIG. 6E shows two-dimensional t-distributed stochastic neighbor embedding (t-SNE) visualization of the polarization properties of the fluorescent positive and fluorescent negative datasets from the borderline-SMOTE oversampling method with a perplexity value of 30. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6F:
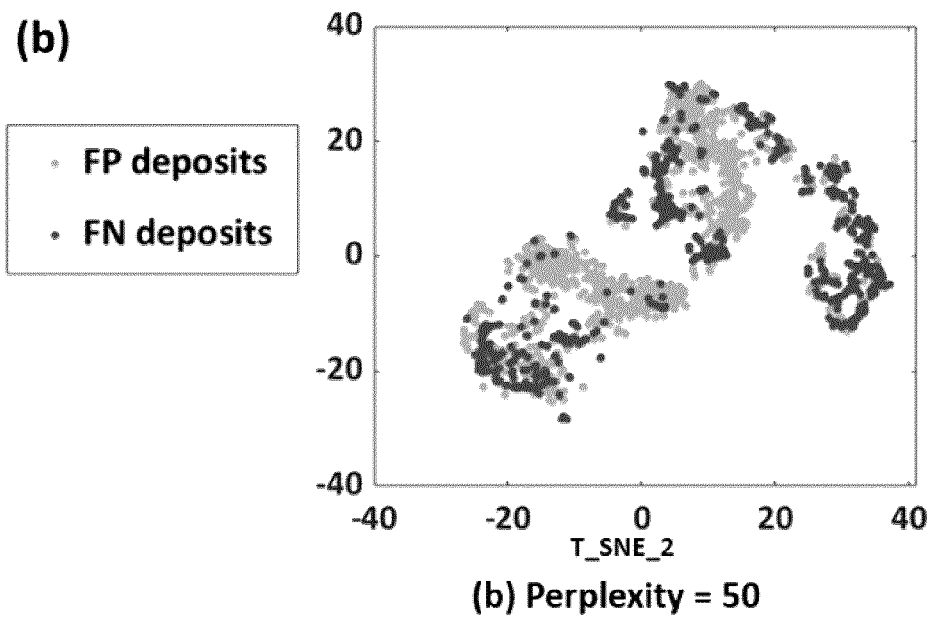
FIG. 6F shows two-dimensional t-distributed stochastic neighbor embedding (t-SNE) visualization of the polarization properties of the fluorescent positive and fluorescent negative datasets from the borderline-SMOTE oversampling method with a perplexity value of 50. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6G:
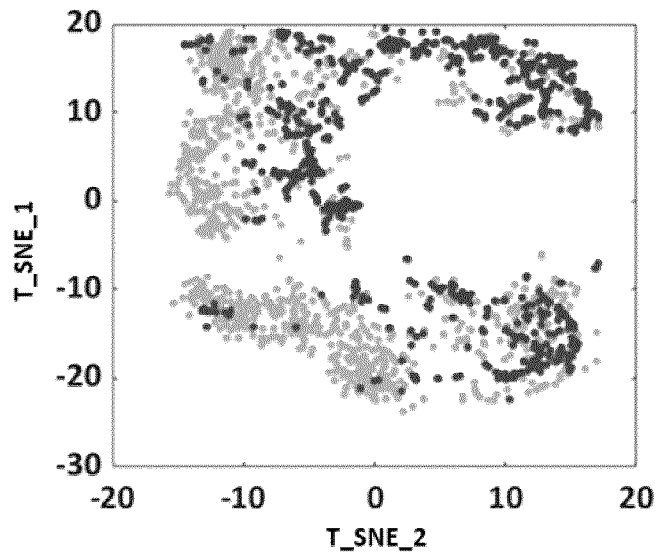
FIG. 6G shows two-dimensional t-distributed stochastic neighbor embedding (t-SNE) visualization of the polarization properties of the fluorescent positive and fluorescent negative datasets from the borderline-SMOTE oversampling method with a perplexity value of 80. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 6H:
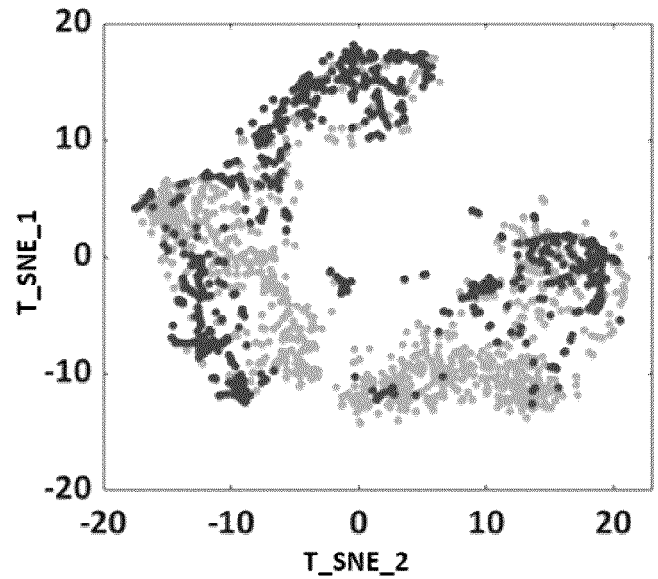
FIG. 6H shows two-dimensional t-distributed stochastic neighbor embedding (t-SNE) visualization of the polarization properties of the fluorescent positive and fluorescent negative datasets from the borderline-SMOTE oversampling method with a perplexity value of 100. The distribution focus moves from the local to the global as the perplexity increases. FP and FN are fluorescent positive and negative deposits, respectively. T_SNE_1 and T_SNE_2 are the axes of the two-dimensional space to which the t-distributed stochastic neighbor embedding mapped the higher dimensions.
Figure 7:
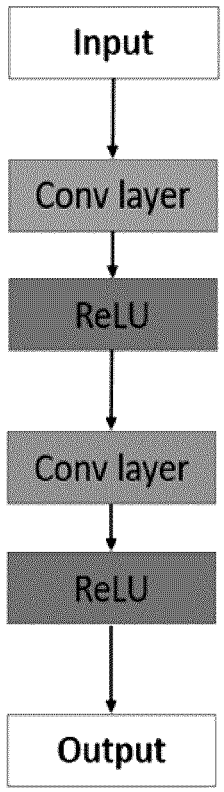
FIG. 7 shows the classification model for classifying protein deposits used to classify pure amyloid beta deposits from pure alpha synuclein deposits. It uses the pretrained Resnet 101, which is a type of convolutional neural network known as a residual network, which attempts to mimic neural connections. This FIG. 7 compares a regular network (on the left) to the residual network used (on the right). The residual network uses skip connections which are shortcuts which allow the network to jump over some layers to avoid degradation in accuracy as the depth of network increases. Conv layers are convolutional layers within which a filter is applied to an input. Batch norm is a type of normalization used to normalize the output of the previous layer. ReLU is the rectified linear unit which will output the input directly if it is positive, otherwise, it will output zero. Because of the identity mapping that occurs in Resnet, the function $H(x)=F(x)+x$ is used instead of $H(x)=F(x)$.
Figure 7:
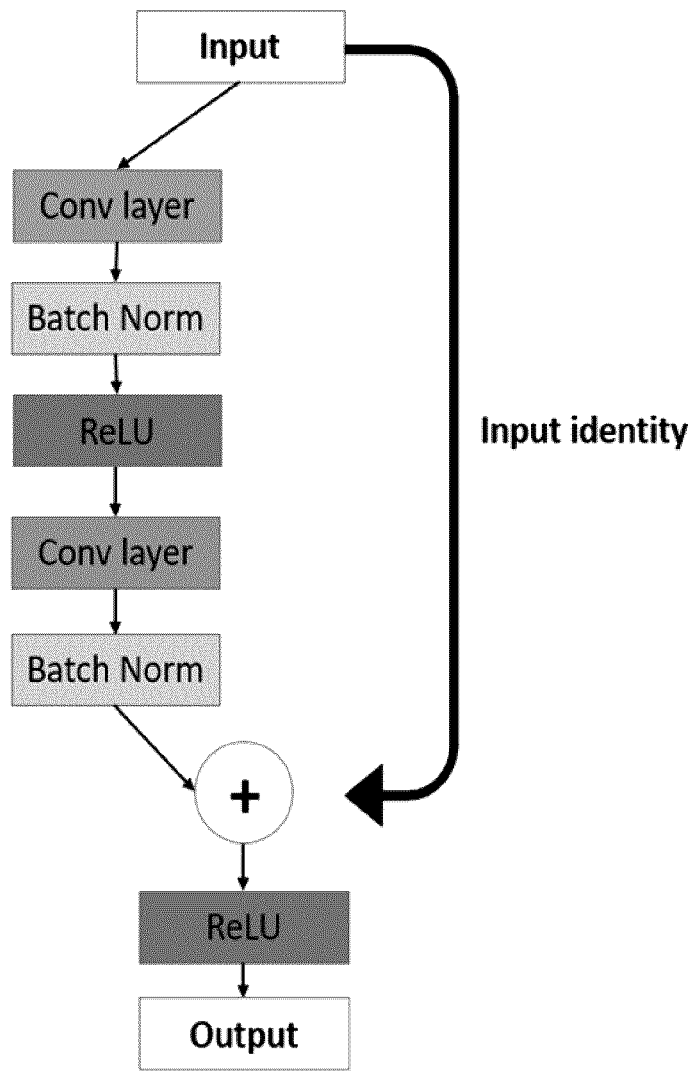
Figure 8A:
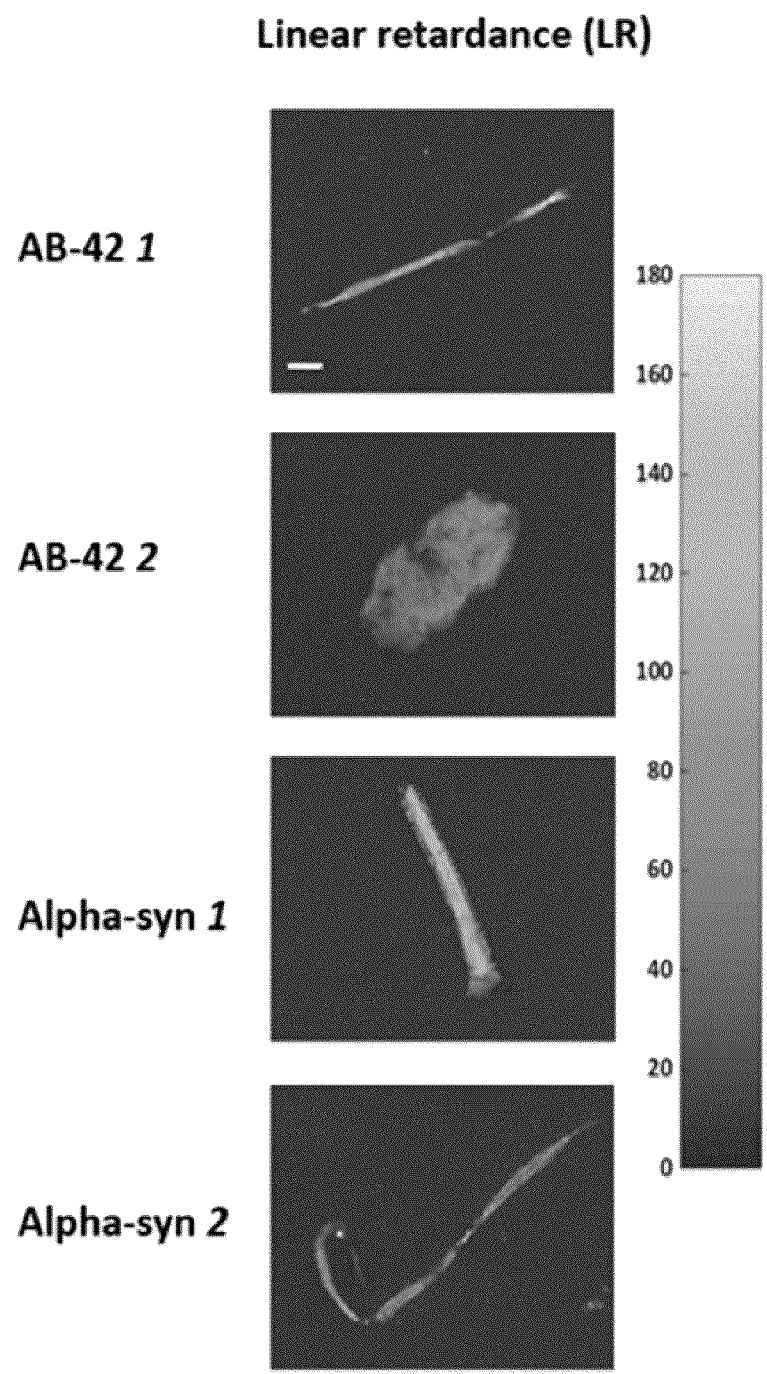
FIG. 8A are linear retardance (LR) maps which indicate specific interactions with polarized light of selected deposits of amyloid beta 42 (labelled AB-42) and alpha-synuclein (labelled Alpha-syn). These pure proteins were grown on glass. The shapes of the proteins vary not only within the protein type but also between the species of protein. These are maps of the measured linear retardance (LR) across each protein deposit. There are 2 deposits of amyloid beta 42, followed by 2 deposits of alpha-synuclein. Linear retardation varies between 0 and 180 degrees.
Figure 8B:
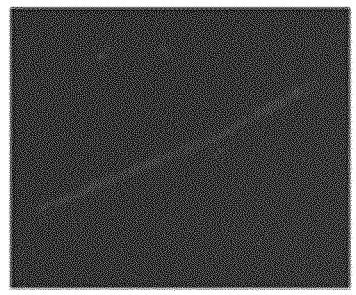
FIG. 8B are linear diattenuation (LD) maps which indicate specific interactions with polarized light of selected deposits of amyloid beta 42 (labelled AB-42) and alpha-synuclein (labelled Alpha-syn). These pure proteins were grown on glass. The shapes of the proteins vary not only within the protein type but also between the species of protein. These are maps of the measured linear diattenuation (LD) across each protein deposit. There are 2 deposits of amyloid beta 42, followed by 2 deposits of alpha-synuclein. Linear diattenuation varies between 0 and 1.
Figure 8B:
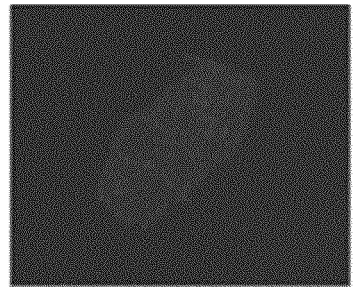
Figure 8B:
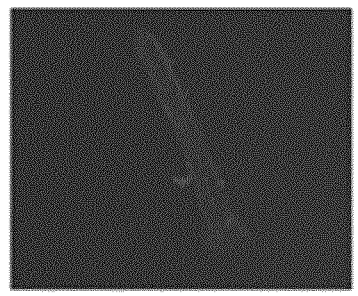
Figure 8B:
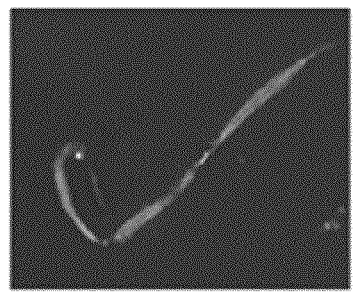
Figure 8B:
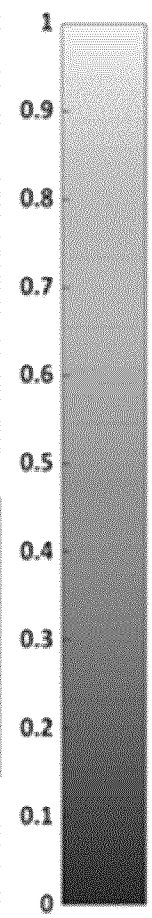
Figure 8C:
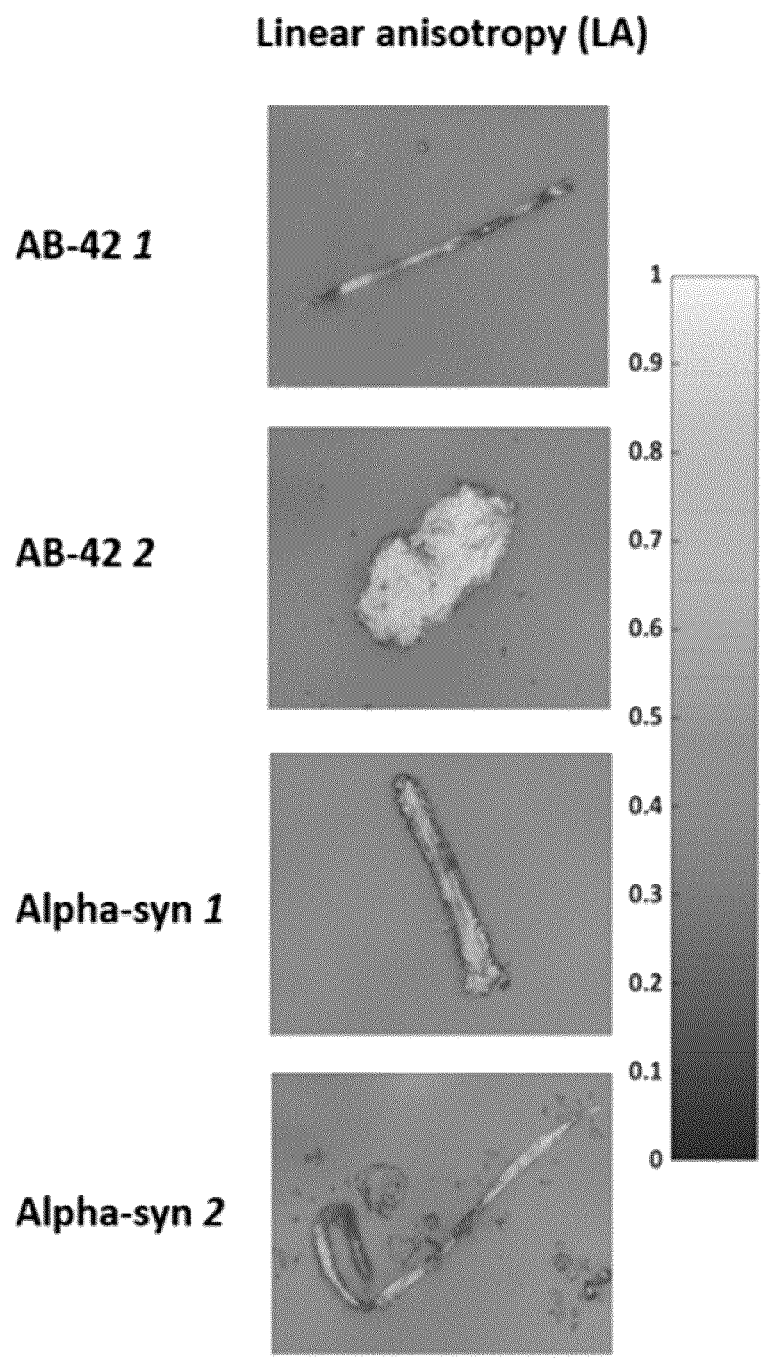
FIG. 8C shows linear anisotropy (LA) maps which indicate specific interactions with polarized light of selected deposits of amyloid beta 42 (labelled AB-42) and alpha-synuclein (labelled Alpha-syn). These pure proteins were grown on glass. The shapes of the proteins vary not only within the protein type but also between the species of protein. These are maps of the measured linear anisotropy (LA) across each protein deposit. There are 2 deposits of amyloid beta 42, followed by 2 deposits of alpha-synuclein. Linear anisotropy varies between 0 and 1.
Figure 8D:
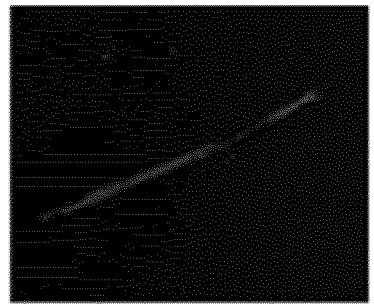
FIG. 8D shows combination images where the maps in FIG. 8A (measured LR), FIG. 8B (measured LD) and FIG. 8C (measured LA) were input as a red image, a green image, and a blue image respectively. For each deposit, the 3 images were then combined to give white light images shown in FIG. 8D. The resulting images indicate interactions with polarized light of selected deposits of amyloid beta 42 (labelled AB-42) and alpha-synuclein (labelled Alpha-syn). These pure proteins were grown on glass. The shapes of the proteins vary not only within the protein type but also between the species of protein. There are 2 deposits of amyloid beta 42, followed by 2 deposits of alpha-synuclein. The greyscale images do not reproduce the information contained in the full colour images.
Figure 8D:
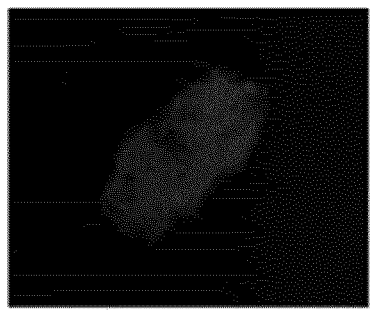
Figure 8D:
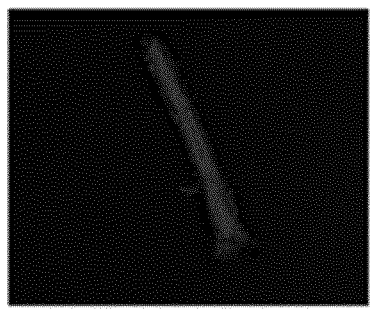
Figure 8D:
Figure 9A:
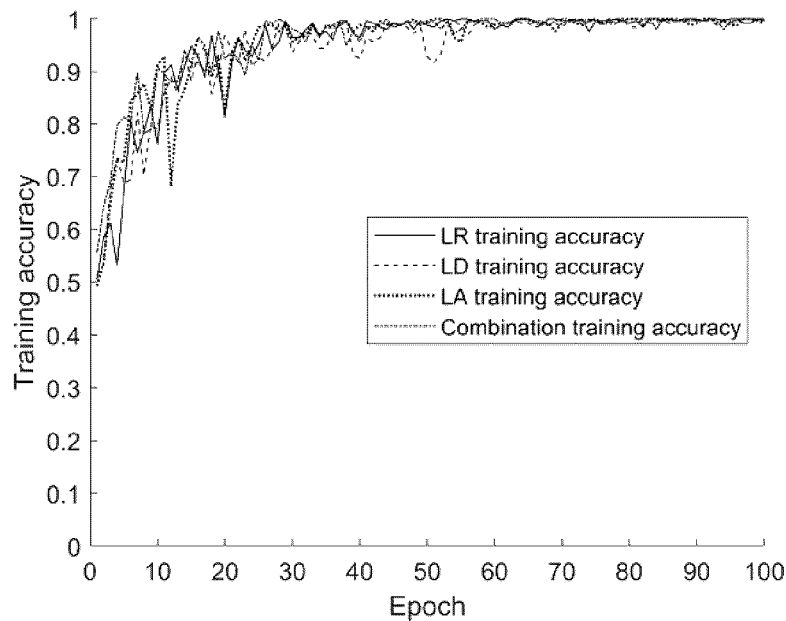
FIG. 9A shows learning curves of the convolutional neural network (CNN) trained by linear retardance (LR), linear diattenuation (LD), linear anisotropy (LA) and their combination images in 100 epochs for training accuracy. The training accuracies of the four CNNs all improved rapidly in the first 20 epochs and then slowly improved, finally stable at approximately 100%.
Figure 9B:
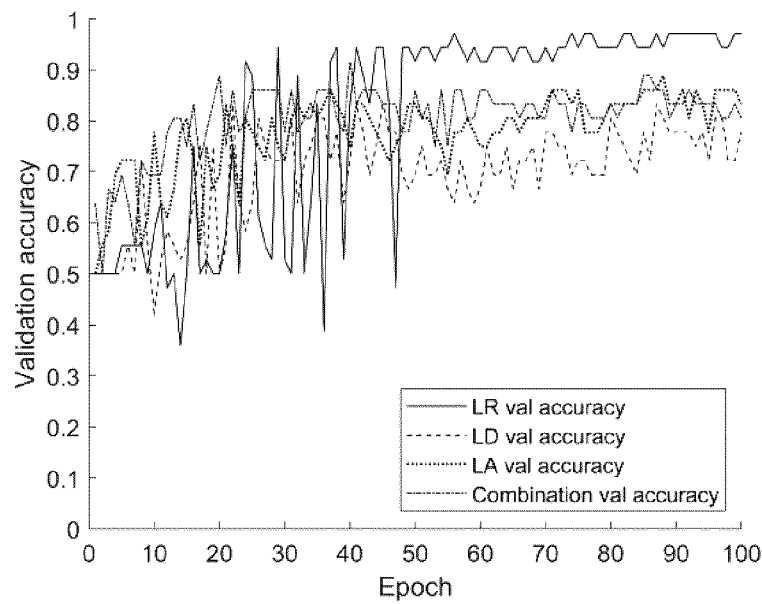
FIG. 9B shows the validation accuracy learning curves of the CNNs trained by LR, LD, LA, and their combination images in 100 epochs. The validation accuracy was tested on data not used for training. The validation learning curves fluctuated more than the training learning curves, the differences between the four convolutional neural networks (CNNs) were also more obvious than for the training curves in FIG. 9A. Val accuracy indicates validation accuracy. Validation accuracy for linear retardance (LR) images attained a higher value than for other properties. Combined images and linear anisotropy images (LA) performed similarly but not as well as LR images. Linear diattenuation (LD) images produced the lowest accuracy.
Figure 10A:
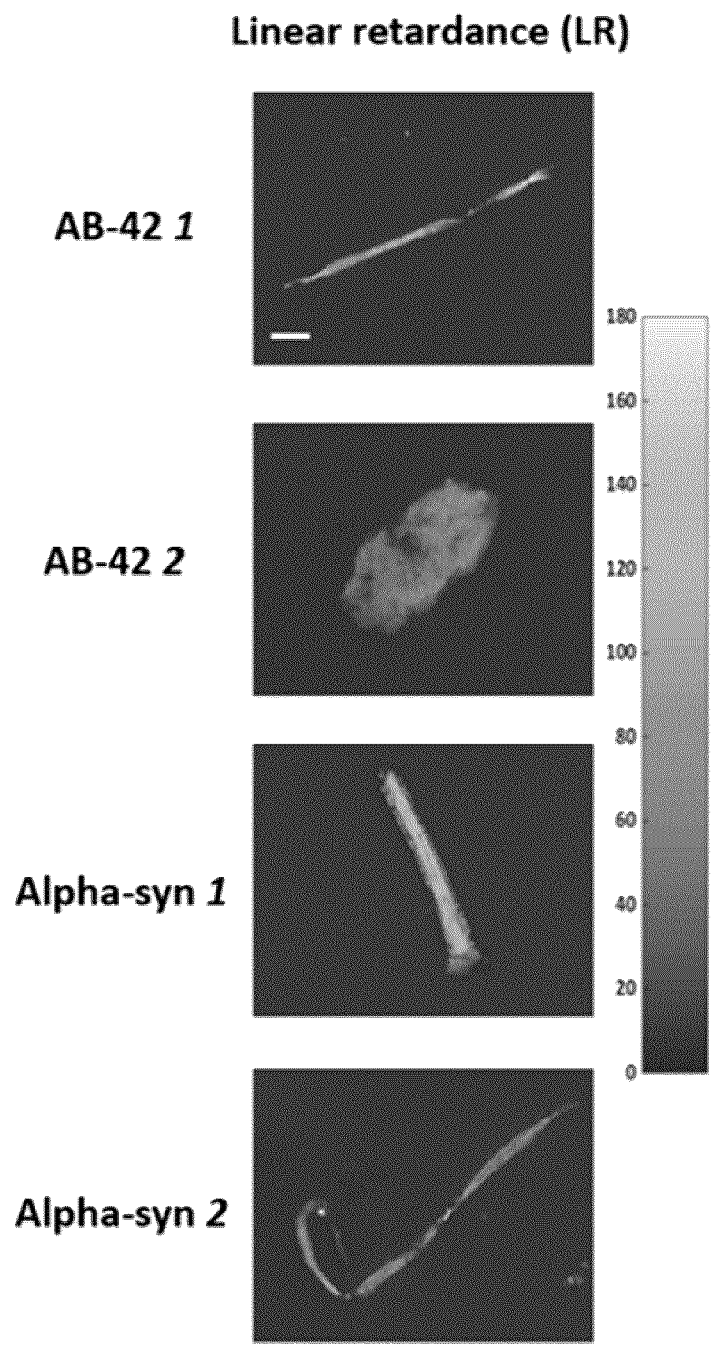
FIG. 10A shows linear retardance images of four pure protein deposits, 2 amyloid beta and 2 alpha synuclein. The saliency maps in FIGS. 10B, 10C and 10D indicate which parts of the image(s) are used in differentiating the protein types. As the shapes of the deposits are apparent in those saliency maps, the inventors' CNN models are making decisions based on a part of the image known to be related to the shape of the corresponding protein deposit, rather than randomly selected areas.
Figure 10B:
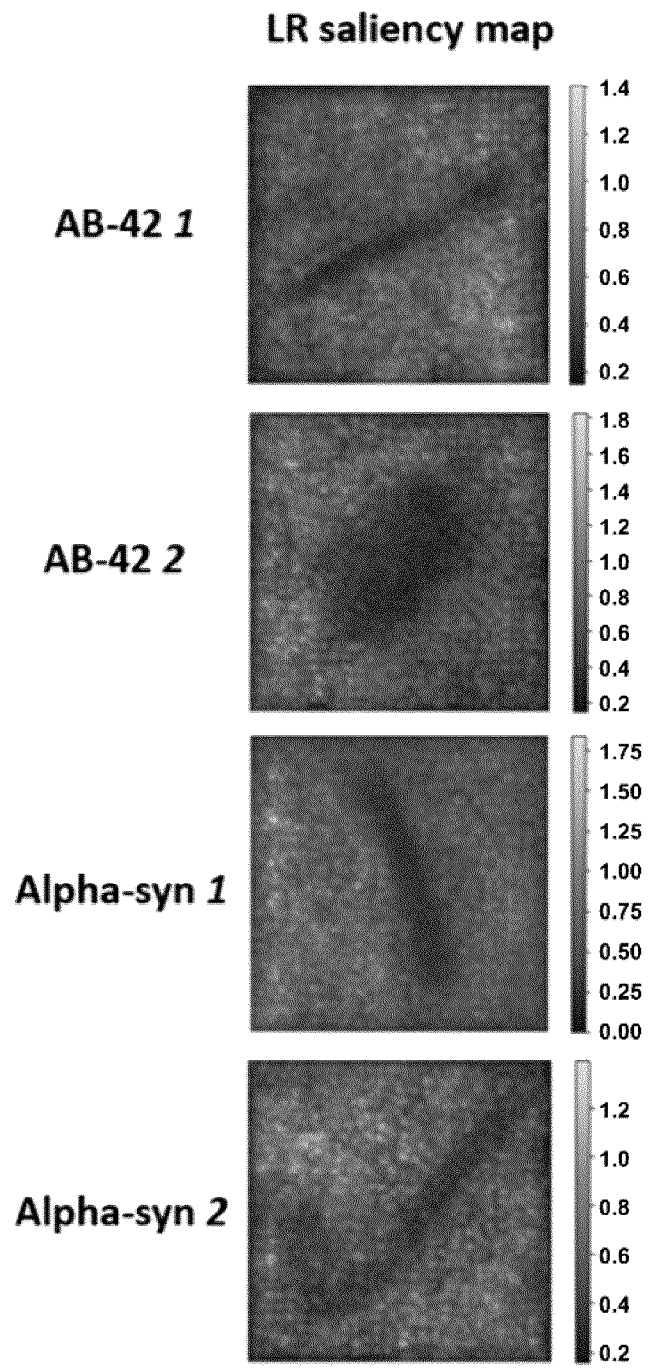
FIG. 10B is a saliency map of four pure protein deposits, 2 amyloid beta and 2 alpha synuclein, for CNNs based on their linear retardance (LR). The saliency map indicates which parts of the image(s) are used in differentiating the protein types. As the shapes of the deposits are apparent in the saliency maps, the inventors' CNN models are making decisions based on a part of the image known to be related to the shape of the corresponding protein deposit, rather than randomly selected areas.
Figure 10C:
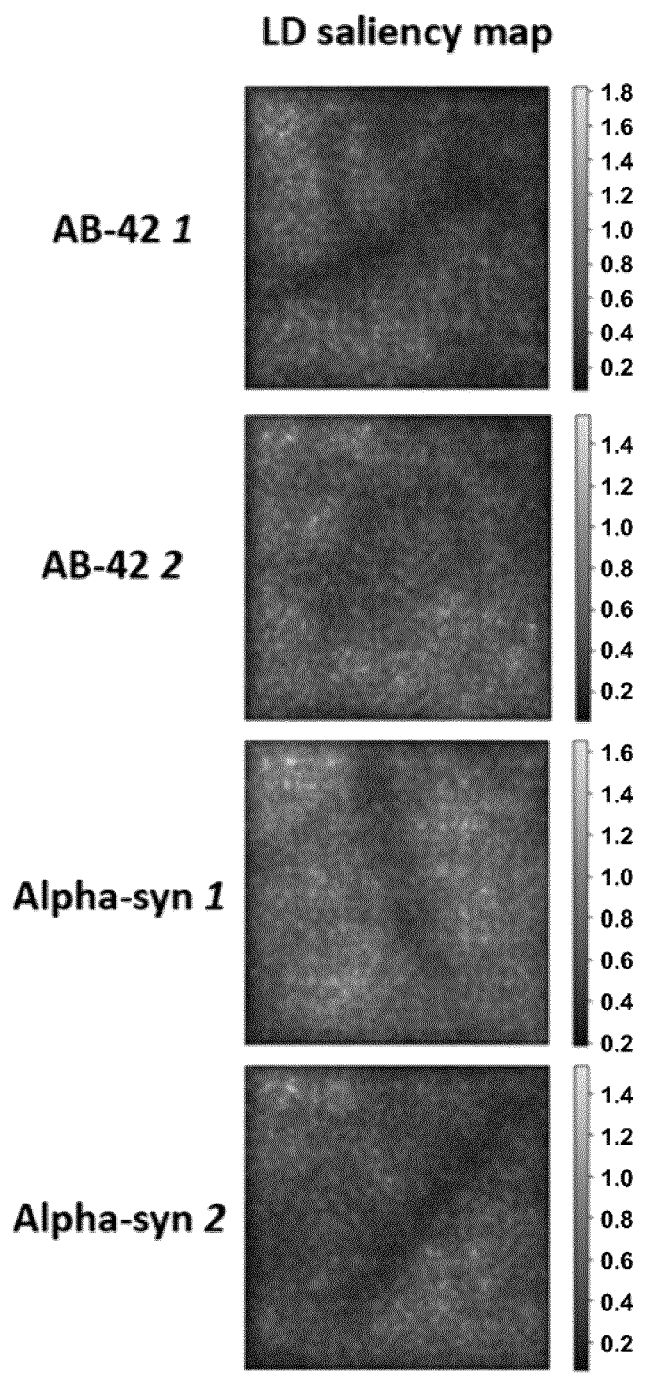
FIG. 10C is a saliency map of four pure protein deposits, 2 amyloid beta and 2 alpha synuclein, for CNNs based on their linear diattenuation (LD). The saliency map indicates which parts of the image(s) are used in differentiating the protein types. As the shapes of the deposits are apparent in the saliency maps, the inventors' CNN models are making decisions based on a part of the image known to be related to the shape of the corresponding protein deposit, rather than randomly selected areas.
Figure 10D:
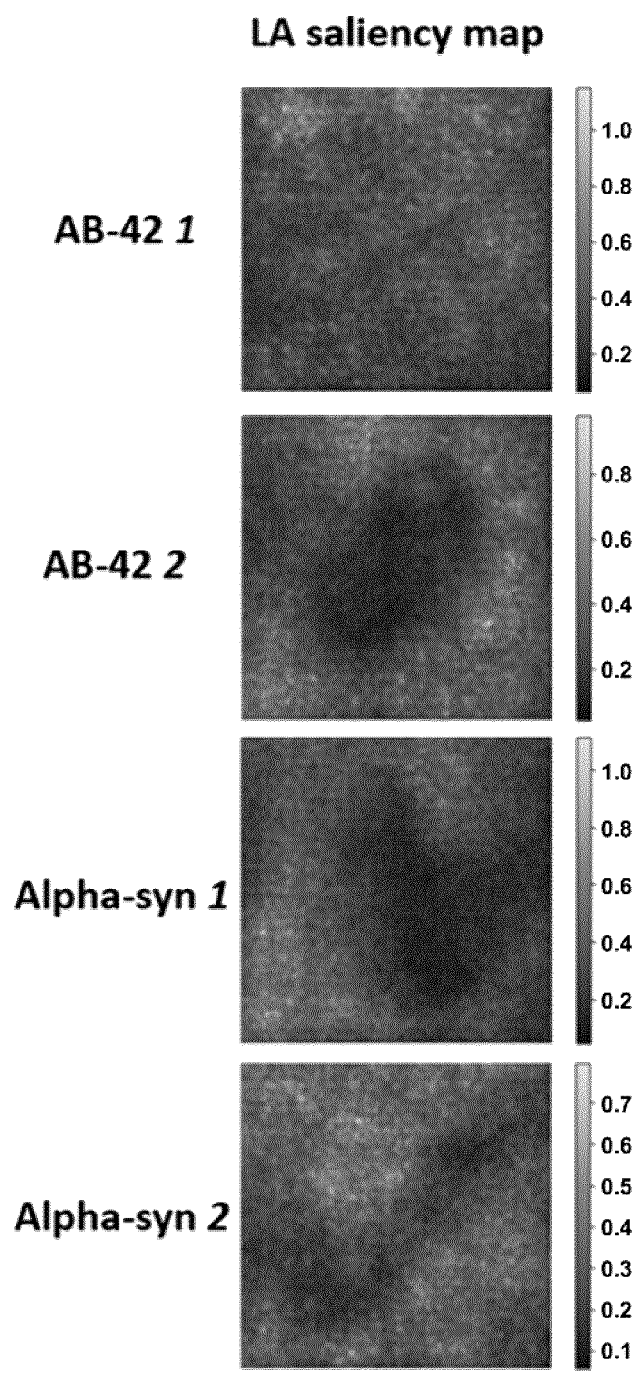
FIG. 10D is a saliency map of four pure protein deposits, two (2) amyloid beta and two (2) alpha synuclein, for CNNs based on their linear diattenuation (LD). The saliency map indicates which parts of the image(s) are used in differentiating the protein types. As the shapes of the deposits are apparent in the saliency maps, the inventors' CNN models are making decisions based on a part of the image known to be related to the shape of the corresponding protein deposit, rather than randomly selected areas.
Figure 10E:
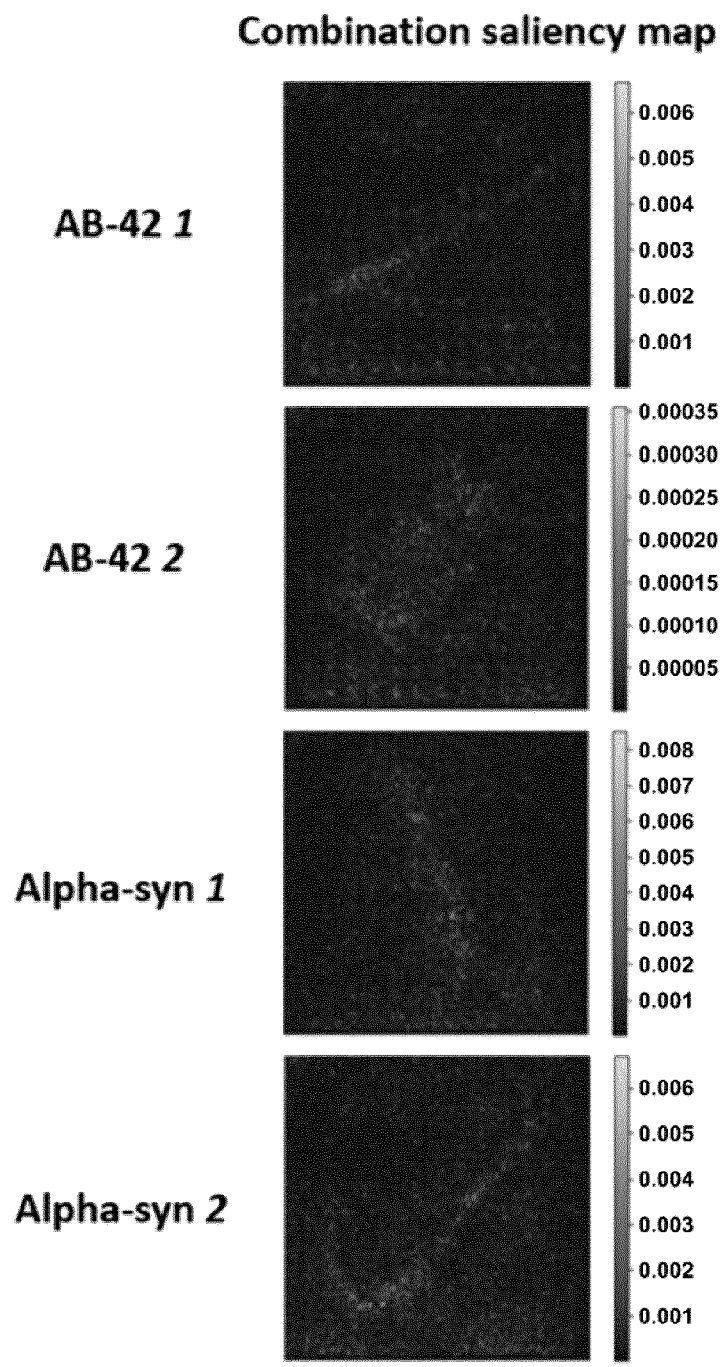
FIG. 10E is a saliency map of four pure protein deposits, two (2) amyloid beta and two (2) alpha synuclein, for CNNs based on their three properties, combined into white light (3 channel) combination images, including linear retardance (LR), linear diattenuation (LD) and linear anisotropy (LA). The saliency map indicates which parts of the image(s) are used in differentiating the protein types. As the shapes of the deposits are apparent in the saliency maps, the inventors' CNN models are making decisions based on a part of the image known to be related to the shape of the corresponding protein deposit, rather than randomly selected areas.
Figure 11A:
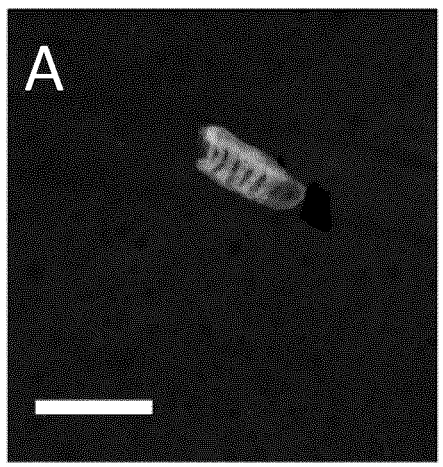
FIG. 11A is an example of a vessel-associated amyloid deposit (presumed amyloid beta), stained with thioflavin S, which is inside an outer vessel wall in a post-mortem retina. The scale bar in A is 50 µm. The deposit found in this subject (with mild brain CAA) lies within and at the top of a vessel, see FIG. 11B.
Figure 11C:
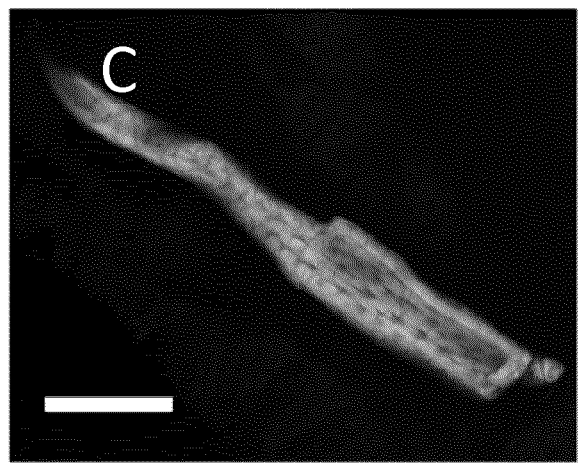
FIG. 11C is a deposit which was hollow in its broader region (see the gap in FIG. 11D in its cross-section perpendicular to the long axis of the vessel). Thus, at this location, the deposit is circumferential within the vessel. This deposit also demonstrates banding. The scale bar in C is 50 µm. Ticks are separated by 5 µm.
Figure 11B:
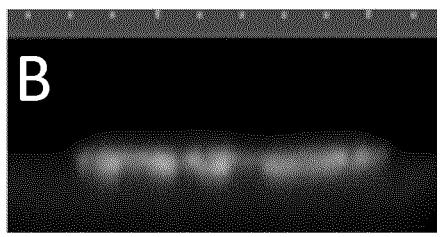
FIG. 11B is the deposit in FIG. 11A in cross section and it is slightly curved. The deposit is not circumferential within the vessel, indicating milder CAA pathology in the retina than would be indicated by circumferential deposits. Its banding resembles patterns reported in brain CAA where amyloid displaces smooth muscle cells in the basement membrane of the tunica media. Ticks are separated by 5 µm.
Figure 11D:
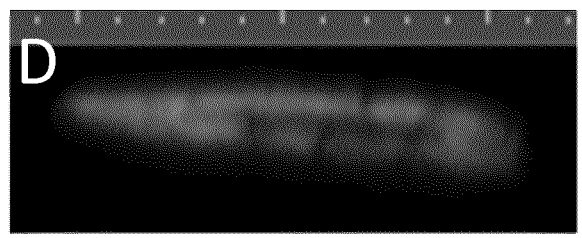
Figure 12A:
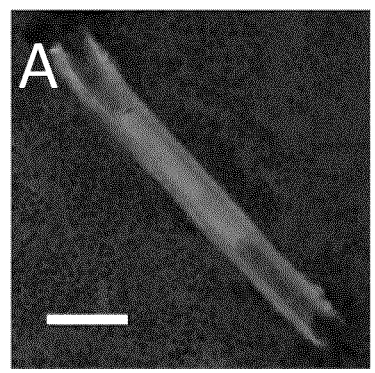
FIG. 12A is a deposit which is evident along part of the vessel. The scale bar in A is 50 µm.
Figure 12B:
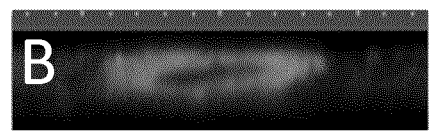
FIG. 12B is a cross-section from the deposit in FIG. 12A and shows a circumferential deposit, thicker than in FIG. 11A. Ticks are separated by 5 µm.

In the analyses, the means and standard deviations of 14 polarimetric properties were used in the analyses and their importance is given in FIGS. 4 and 5 for Random Forrest. With retinal oversampling, LR and LA were two dominant polarimetric properties (features) in predicting Thioflavin-S fluorescence. Their means and STDs together accounted for 74.8% of the total variable importance. When the analyses were rerun with only mean and STD of these 2 polarimetric properties as feature inputs. The accuracy of Random Forrest analysis remained above 90%. Thus, variable importance can be used to reduce the number of variables in the analyses and make them more efficient.

FIGS. 6A, 6B, 6C, 6D, 6E, 6F, 6G, and 6H demonstrate that the data points of fluorescent negative and fluorescent positive areas are somewhat more separated in the inventors' novel retinal oversampling method than in the borderline-SMOTE oversampling method. The methods described herein and in FIGS. 1 to 6 predict from the polarimetric properties of retinal deposits, with high accuracy, the existence of amyloid with thioflavin positive fluorescence signals. The present inventors have shown that, in combination with machine learning algorithms, imaging using Mueller matrix polarimetry can detect amyloid positive deposits in the ex vivo retina without using a dye with high accuracy (see Provisional Patent Application No. 63/038,256, Attachment 1).

More recently, the inventors' and others have found amyloid, presumed to be amyloid beta in the post-mortem retinas of humans (and/or animal models of diseases) in association with other conditions, including age related macular degeneration and glaucoma which are considered to be conditions which primarily affect the retina and are sight threatening.

The present inventors have demonstrated that the amyloid beta, found in deposits in the retina or in retinal tissue or in other retinal structures in association with Alzheimer's disease (AD) or age-related macular degeneration (AMD) can be classified as either associated with AD or associated with AMD using polarimetric properties and multifractal spectral properties and potentially other properties evident in a given optical imaging modality used to image the retina. The present inventors use the classification techniques described herein (see FIGS. 16, 17, 18, 19 and 20)

Figure 20:
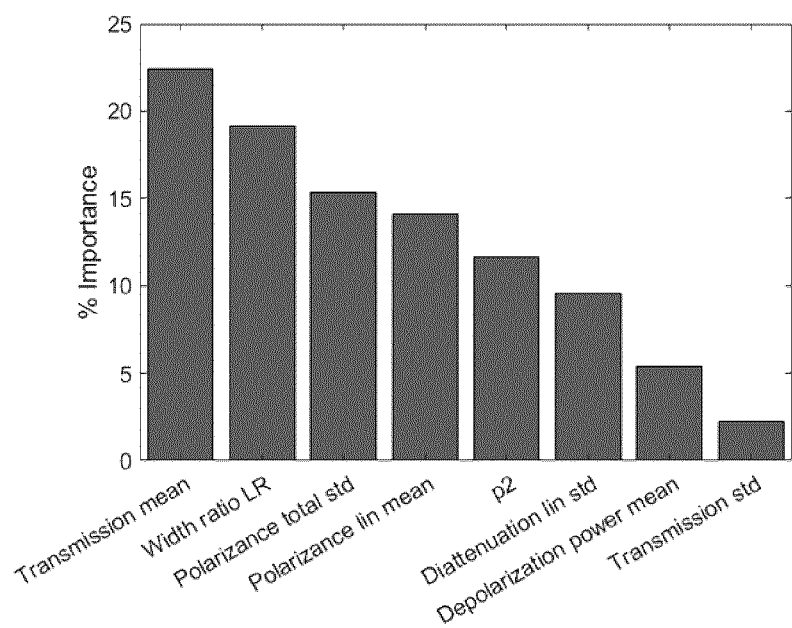
FIG. 20 is the importance of the 8 variables used in Random Forrest to achieve a resulting accuracy of 84% in differentiating deposits associated with AD and those associated with AMD. All variables have greater than 3% importance. 5 variables account for over 80% of the importance. The most important variables were transmission, a polarimetric measure and the width ratio, the ratio of the widths of the first two peaks in the multifractal spectra (MFS). P2 is the prominence of the second peak in the MFS while other variables were from polarimetric analysis. Std is standard deviation.

Herein as an example, in order to classify deposits associated with Alzheimer's disease as separate from those associated with age related macular degeneration (see Provisional Patent Application No. 63/038,256, Attachment 4, and FIGS. 16, 17, 18A, 18B, 19 and 20 of the present application). The present inventors extend their approach from polarimetry properties (see for example FIG. 17) as the inventors' optical signal to the use of properties of the multifractal spectra (example FIGS. 18A, 18B, and 19) and properties derived from data on dimensions the present inventors classify these two groups of deposits in post-mortem retinas without the use of their anterior or posterior location. The present inventors classify the properties of the deposits in the two deposit types using two machine learning methods: Fisher's non parametric discriminant analysis and Random Forrest, of which Random Forrest had a higher accuracy of classification of over 84%. Properties that contributed most to the accuracy were a mix of multi spectral and polarimetry variables (FIG. 20).

The inventors' and others have also found presumed amyloid beta in the retinas of those who have other conditions of the brain, including cerebral amyloid angiopathy (herein referred to as CAA), a condition identified in the brain which is difficult to diagnose and causes an increased risk of stroke.

Present inventor Campbell has previously taught that imaging with polarized light is a non-invasive way to make deposits of amyloid, presumed to be amyloid beta (Aβ), visible in the retina of the eye. Present inventor Campbell has shown and patented methods to locate the Aβ within the neural retina where it may have deleterious effects on visual function. In addition, the present inventors have previously shown and Campbell has previously taught that the type and density of amyloid protein deposits (presumed to contain Aβ) in the neural retina predicts the occurrence and severity of amyloid in the brain. Present inventor Campbell has previously described methods which image and locate Aβ in the neural retina which is advantageous to determining Alzheimer's disease, to tracking disease severity, to assessing the efficacy of treatments of Alzheimer's disease and potentially to treating the effects of amyloid (presumed Aβ) deposits in the retina. These advantages apply both to humans and to animals which develop conditions similar to Alzheimer's disease in which novel diagnostics and therapies are tested.

Figure 13:
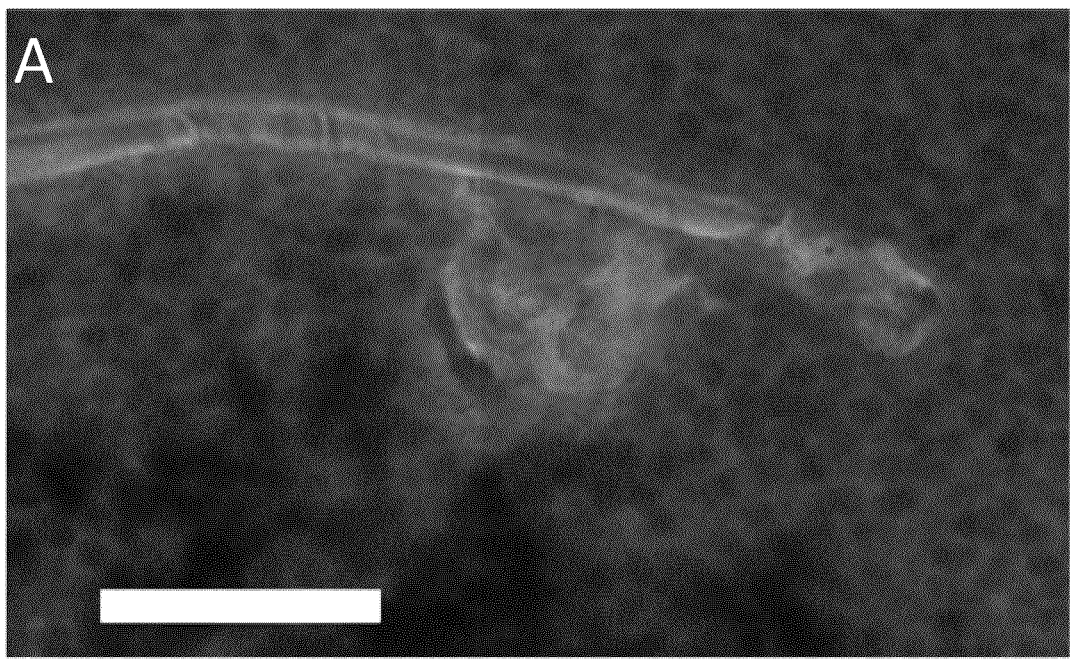
FIG. 13 is an example of retinal vessel changes analogous to dyshoric changes seen in the brain. Amyloid appears to be deposited within the walls of the long vessel. The feature adjacent to the vessel is analogous to the definition of a dyshoric amyloid deposit in the brain as it touches the vessel which itself contains amyloid. This suggests that amyloid breached the vessel wall and spread into the surrounding retinal tissue. The breach is not visible. The scale bar is 50 µm.

Referring to FIGS. 11A, 11B, 11C, 11D, 12A, 12B, 13, and 14 of the present application, the present inventors use images taken in fluorescence to classify the condition of cerebral amyloid angiopathy (CAA) in the retina due to the presence of amyloid in the blood vessels. The inventors' observations on post-mortem retinas and brains teach that the types of CAA retinal deposits present in FIGS. 11 and 12 are similar to and appear to predict the presence of analogous deposits in the blood vessels of the brain and thus the presence of brain CAA. From there, the present inventors precede to define a scale of severity of these deposits of retinal amyloid in CAA. In the inventors' direct observations, the presence of and severity of amyloid in the vessels of the retina is as visible in polarimetry measurements as it is in fluorescence imaging. FIG. 13 shows a more severe deposit, likely both inside and outside a vessel, a candidate dysphoric deposit which may have broken through the wall of the vessel. More samples of post-mortem retina and brain are needed but the present inventors teach that this type of deposit associated with retinal blood vessels is likely to predict dishoric deposits in the brain (and associated risk of stroke). Due to morphology and location, the present inventors are clearly able to classify the deposits in FIGS. 11, 12 and 13 as being associated with blood vessels in contrast to the deposit in FIG. 15 in retinal tissue, not associated with a vessel.

As well as fluorescent dyes, the present inventors have demonstrated that these vessel-associated deposits within and just outside blood vessels, have polarimetric signal, distinct in morphology from those of deposits within the retinal tissue. This means that the inventors' novel dye free method of imaging amyloid deposits can be extended to differentiate and classify the presence of and severity of protein deposits associated with vessels.

As well as in association with Alzheimer's disease, Aβ, other amyloid and other types of protein deposits are known to occur in the retina in association with other retinal conditions and other neurodegenerative diseases. It is the inventors' expectation that, in the future the types of protein deposits found in the retina in association with neurodegenerative diseases will increase, as will the number of different diseases that they are found in association with. However, prior to the provisional patent associated with this application, optical and classification methods of differentiating these protein deposits in the retina and particularly in the living retina to determine the type of protein and/or the particular condition(s) and/or the severity of said condition(s) with which the deposits of protein(s) were associated had not been outlined for non-invasive imaging methods.

Thus, the present inventors have also extended their consideration to the differentiation and classification of different pure protein types (see FIGS. 7, 8, 9, 10), as well as to the use of additional optical properties of protein deposits in the retina and to the use of images as a whole or in part for this classification of protein type in particular of pure amyloid beta 42 versus pure alpha synuclein with an accuracy over 90% (see FIGS. 7, 8, 9, 10). In this case the calculated and plotted pixel by pixel interaction of individual deposits with polarized light produced high contrast "images" for both protein deposit types (linear retardance, LR-FIG. 8A, Linear diattenuation, LD-FIG. 8B and Linear anisotropy, LA-(FIG. 8C). As a novel approach, the present inventors combined these three images (FIG. 8D) to give an artificial white light image, containing information on LR, LD and LA simultaneously. Resnet, a convolutional neural network whose chosen configuration is summarized in FIG. 7, was used with each of these image types from each deposit in a separate analysis (LR, LD, LA or combined images). From training and validation accuracies (FIGS. 9A and 9B), it can be seen that linear retardance (LR) images gave best performance with an accuracy above 90%. Saliency maps for each of the LR, LD, LA and combined analysis (FIGS. 10B, 10C, 10D, and 10E) compared to LR maps demonstrate that data from the deposits in comparison with data from the surrounding retina is preferentially used to categorize the deposits.

Following the intellectual property of the provisional patent, this application is for an improvement patent that shows methods by which the present inventors can assess properties of retinal amyloid deposits or retinal protein deposits more generally and use differences in their properties between two groups of deposits (defined for example by location or by properties of their images). or differences between individuals with different conditions who are expected to have different types of protein deposits to either classify the deposits as belonging to one of the two groups of deposits and/or classify the individuals as belonging to one or more of the groups of individuals. These individuals for example would have a particular condition corresponding to a particular location of a type of protein deposit and/or corresponding to the presence of one or more particular type(s) of protein deposit(s). The properties used are the properties of protein deposits in the living retina: their properties in optical images including but not limited to their polarimetric properties, that is their interactions with polarized light; their properties from multifractal spectra or other fractal properties, properties derived from data on dimensions, morphology and location on the retina and/or other interactions with light that are measured for the purposes of said classification.

The inventors disclose herein the use of classification methods analogous to those mentioned above to classify protein deposits in the retina as being associated with two or more different proteins (alpha synuclein versus amyloid beta in the example above), AD versus CAA (see FIGS. 11, 12, 13, and 14 of the present application) for obvious differences in deposit morphology in the two conditions), and/or with AD versus other neurodegenerative diseases, and/or classifying two or more neurodegenerative diseases or simultaneously classifying more than two of the conditions which are known or may in the future be shown to be associated with the expression of proteins in retinal tissue, in retinal structures or in deposits. The present inventors also teach that the methods for the differentiation of severity of a marker, or of the disorder associated with said biomarker that have been described herein for the severity of CAA and previously patented for the severity of AD by Campbell can be extended to differentiate and classify the severities of other biomarkers, and/or conditions associated with them.

Each of the above samples of differentiation of deposit types and classification into classes can be performed by any other technique related to machine learning, artificial intelligence or any closely related classification technique or any others. It has been the inventors' preferred approach to use several techniques for each differentiation and to vary the input parameters so as to determine which technique is giving the best accuracy of classification in each situation.

The present inventors' work and studies disclosed herein has for the first time identified properties and characterised said properties of the protein deposits within the retina to allow differentiation of the condition(s) present and the severity of said condition(s).

As stated in the summary of invention, the methods and apparatus described are aimed at imaging and analysing images of presumed protein deposits in the retina, retinal tissue or retinal structures and discloses methods further differentiating or classifying said deposits and other optical signals from retinal structures into 1) whether they contain or do not contain classes, of proteins or protein deposits called amyloids OR other proteins and/or protein deposits related to neurodegenerative eye and brain disease(s); 2) which type(s) of amyloid or other protein the deposits they contain, as well as 3) whether the form of the deposit is associated with a class of diseases or with one or another specific condition(s) (or disease(s)); whether or not this is a disease or class of disease associated with the retina or more generally with the nervous system, including the brain or 4) classified as associated with one or another level of severity of condition(s) (or disease(s)), or other properties of the deposits singly or in combination can be used to classify and differentiate the condition(s) or disease(s) present.

The first classification described is whether particular deposits in the retina or the retinal tissue or retinal structures contain a class of proteins called amyloids, found in conjunction with a large number of neurodegenerative diseases in the brain and in the retina. In ex vivo tissue, these deposits would fluoresce when stained with thioflavin (or other dyes which specifically mark amyloid proteins).

The present inventors have found that the classification of whether a deposit will stain with thioflavin or not, can be made without staining it on the basis of other properties of the deposit, which can be determined either from images of the retina or from the properties of light returning from the retina (see Provisional Patent Application No. 63/038,256, Attachment 1, and FIGS. 1, 2, 3, 4, 5, and 6 of the present application). In particular, the present inventors have used polarimetric properties which can be measured without a dye, to differentiate or distinguish between those that are thioflavin positive and those that are thioflavin negative. This will improve the accuracy of the identification of deposits which contain amyloid proteins versus those that contain little of no amyloid protein as defined by the in vitro standard of thioflavin staining. This is for primary use in live eye imaging as thioflavin is toxic in the living eye. This makes this classification into thioflavin positive and thioflavin negative practical to use. The classification also improves the accuracy of the identification of deposits which contain amyloid proteins versus those that contain little of no amyloid protein as defined by the in vitro standard of thioflavin staining. The present inventors describe in detail some methods that can be used in this classification in Provisional Patent Application No. 63/038,256, Attachment 1.

Other methods described later in this document are also possible in the classification. Once the properties of the retinal deposits that make them thioflavin positive are known from these ex vivo experiments, the inventors' knowledge of live eye imaging allows us to use analogous properties in live eye images to classify deposits as thioflavin positive (amyloid) or thioflavin negative (non amyloid).

Other methods described later in this document are also possible inputs into the classification. Once the properties of the retinal deposits that make them thioflavin positive are known from these ex vivo experiments, the inventors' knowledge of live eye imaging allows us to use analogous properties in live eye images to classify deposits as thioflavin positive (amyloid) or thioflavin negative (non amyloid).

The second classification into the type of protein contained by a deposit can be made either once these deposit(s) or signals from retinal tissue or structures have been classified as amyloid or not amyloid or without that initial classification. One classification method for classifying deposits as containing one or another protein is demonstrated in Provisional Patent Application No. 63/038,256, Attachment 2, where pure deposits can be classified as amyloid beta 42 or alpha synuclein with high accuracy. These results can then be translated to imaging the deposits, tissues and structures in the living eye given the inventors' knowledge of live eye imaging, leading to the classification of whether one or more proteins are present in the retina. In turn, each identified protein deposit type will be a biomarker of one or more neurodegenerative conditions or diseases. In turn, a particular condition may be identified with confidence if a minimum number of biomarkers of said condition in particular locations and/or morphologies are identified and said subset of biomarkers in said locations of the retina and in said morphologies occur only in one condition with high likelihood. There are many other proteins and protein deposits likely to occur in the retina as biomarkers of many other neurodegenerative brain diseases and other diseases and the methods outline herein for differentiating amongst them are applicable to all of them.

In the third classification application, the deposits can be classified as of a particular form, presenting with a particular morphology or position in the retina and/or having a particular interaction with light. One or more of these properties may allow the deposits to be classified as associated with a class of diseases or with one or another specific condition(s) (or disease(s)); and by inference whether or not this is a disease or class of disease associated with the retina or more generally with the nervous system, including the brain which may contain a particular subset of condition(s) or disease(s) for which the retinal deposits are biomarkers. The deposits can first be classified as a protein or combination of proteins (see second classification), or they can be directly classified as a particular protein is known to be associated with a particular subset of condition(s) or disease(s). For example, amyloid beta is associated with many neurodegenerative conditions, including but not limited to glaucoma and age-related macular degeneration in the retina and Alzheimer's disease and cerebral amyloid angiopathy in the brain, which have been shown by the inventors' group and others to have corresponding amyloid protein deposits in the retina (assumed to be amyloid beta). In issued patents by one of us it was specified that amyloid beta is found in association with AD and/or AMD and that these deposits are separated in depth in the retina.

Herein the inventors extend the classification of deposits associated with the two conditions using polarimetric properties and other optical properties, the multifractal spectra and/or other fractal properties of deposits and properties derived from data on dimensions and location on the retina. In addition, other optical properties of protein deposits in the retina, protein in retinal tissue and within other structures in the retina can be used. The present inventors propose the use of these classification methods described below to classify protein deposits in the retina as being associated with AD, CAA, and/or with AMD with possible extensions to other neurodegenerative retina and brain diseases, and/or classifying two or more neurodegenerative diseases.

In addition, the structure or other properties of the deposits of a given protein or other expressions of a particular protein in deposits, retinal tissue and/or retinal structures are likely to differ among different neurodegenerative conditions associated with that particular protein in the retina and/or the brain. This could in turn lead to differences in the images, differences in optical signals from said protein deposits and/or protein deposits in different neurodegenerative conditions will potentially contain two or more proteins or types of protein deposit(s). This intellectual property then discloses that the properties of this class of deposits, tissue signals and or signals from structures in retina can in turn be classified as indicative of a class of diseases or conditions involving this particular protein or combination of proteins in retinal deposits. In turn this can identify said condition in the retina and/or in the nervous system or brain more generally.

The fourth classification of severity of a given condition can be made either once the deposit(s) or signals from retinal tissue or structures have been classified as amyloid or not amyloid OR once deposits have been classified as containing one or more protein(s) OR prior to either of these classifications if the presentation is indicative of a particular condition or class of conditions of the retina or brain. further properties of the deposits, tissues and structures containing a specific protein or combinations of proteins, other properties such as their number, morphology and/or position in the retina, signal intensity (or any combination thereof) can be used to specify the severity of the condition or disease. The present inventors had previously taught a method for this in previous patents for classifying the severity of Alzheimer's disease. Here the present inventors extend this to other conditions. Herein the present inventors also teach that the severity of cerebral amyloid angiopathy within the blood vessels of the retina can be categorized from images of amyloid protein within the blood vessels of the retina.

General Comments on Classifications

Much of the analysis above discusses classification into one of two classes and many of the examples are of this type. But as more pairwise classifications are made, if the properties used differ in average values or distributions between 3 or more different classes, then classifications can be made into multiple categories from a single set of measured properties (a complete or subset of those outlined above or incorporating more properties measured from retinal images or subsets of images). This would potentially use a branching tree and, as a starting point, properties that are known to classify a single condition or severity from another conditions and severities described. In this case, a classification method like Random Forrest or any other method of classification (statistical, machine learning or Artificial Intelligence) which specifies the importance of specific properties to the classification will be useful in generalizing from a classification of two classes to multiple classes or in completing a sub-classification within a branching tree.

For example, in the Random Forrest classification of thioflavin positive vs thioflavin negative deposits, described below, representing deposits containing amyloid proteins from the small number of deposits that did not contain amyloid, a relatively small number of properties (8) were important to this 2 way classification, leaving many measured polarimetry and multifractal spectral or other fractal properties unused and available for further classifications of the thioflavin positive deposits (assumed to be amyloid) into subclasses.

Similarly, the classification of two classes of deposits: those that are more anterior in the retina (and more likely to be associated with Alzheimer's disease) and those that are more posterior in the retina (and more likely to be associated with age related macular degeneration) using Random Forrest used only 8 properties: leaving many more properties for classification into other categories, including severity of the condition.

The classification into subcategories of any of the four major classifications outlined above can proceed by a number of approaches outlined under Details of Classification Approaches below. The methods used in each classification are similarly chosen from the alternatives outlined.

Details of Classification Approaches

The first classification summarized above, involves identification of which amyloid deposits would be positive if stained with Thioflavin (and presumed to be amyloid beta) and their differentiation from other deposits is important to many neurodegenerative conditions both of the retina (for example glaucoma and age-related macular degeneration) and of the brain (for example Alzheimer's disease). This identification of thioflavin positive deposits will improve the accuracy of the identification of deposits which contain amyloid proteins versus those that contain little of no amyloid protein as defined by the in vitro standard of thioflavin staining. This identification without a dye means no dyes are not used and the method is non-invasive and low risk. Thus, it will be more useful in live eye imaging.

Here the present inventors show in post-mortem tissue that this can be done by analysing images of the retina which have been taken with polarized light and which show evidence of candidate deposits but other optical methods are likely to also produce signals that can be differentiated. In ex vivo tissue, these deposits would fluoresce when stained with thioflavin (or any other dyes which specifically mark amyloid proteins). The present inventors have shown that the classification of whether a deposit will stain with thioflavin or not can be made with high accuracy without staining it on the basis of other properties of the deposit, which can be determined either from images of the retina or from the properties of light returning from the retina (see Provisional Patent Application No. 63/038,256, Attachment 1). This makes it practical to use in dye free live eye imaging, where thioflavin use is not possible because of its toxicity. The present inventors describe in detail some methods that can be used in this classification in attachment 1. Other methods described later in this document are also possible in the classification. Once the properties of the retinal deposits that make them thioflavin positive are known from these ex vivo experiments, the present inventors' knowledge of live eye imaging allows them to use analogous properties in live eye images to classify deposits as thioflavin positive (amyloid) or thioflavin negative (non amyloid).

The second classification, into the type of protein contained in a retinal deposit(s) into a specific protein type is important as a step towards identifying the underlying disease or condition. For example, the list of neurodegenerative conditions and/or diseases associated with amyloid beta differ from the list associated with alpha-synuclein, although in some diseases, both may occur. Thus, the identification of either amyloid beta and/or alpha-synuclein signals from the retina would lead to the presumption of a (retinal or) brain condition know to be associated with the one or both proteins identified and the exact subset of the conditions may be classified from the exact form of the deposit of a particular protein associated with that disease. Multiple conditions could be identified if multiple proteins are identified or if one protein is identified whose structure differs in different conditions or diseases.

Because the present inventors have found that the interactions of retinal deposits found in association with Alzheimer's disease in post-mortem retinas with polarized light are very similar to the interactions of deposits of similar thickness of pure amyloid beta, the present inventors assume that the retinal deposits that the present inventors have found in Alzheimer's disease consist primarily of amyloid beta. Thus, to gain insight into probable differences in the polarimetric properties of retinal deposits of amyloid beta and alpha synuclein, the present inventors have grown pure deposits of both amyloid beta and alpha synuclein. In turn, the present inventors have shown the two types of pure protein deposits have differing interactions with polarized light (polarimetric properties). Furthermore, the present inventors have shown that the images taken with polarized light can allow the deposits to be classified and differentiated as either amyloid beta deposits or alpha synuclein deposits (see Provisional Patent Application No. 63/038,256, Attachment 2). The best differentiation comes from combining these properties in a Random Forrest or Convolutional Neural Network classification scheme. Each of which had high accuracy. These two types of protein deposits have previously been identified in retinas. The inventors expect that it will be possible to identify and separate amyloid beta deposits in retinas from alpha synuclein deposits when one or both types are present in the retina. And here the present inventors teach that one could then infer the neurodegenerative disease process in the brain (if deposits are in anterior retinal layers) or the combination of neurodegenerative retinal and brain diseases present. The inventors expect that once deposits are identified as alpha synuclein deposits a diagnosis of one of several diseases in the brain in which these deposits occur will be enabled. The best differentiation comes from combining these properties in a Random Forrest or Convolutional Neural Network classification.

The present inventors extend some of the classification methods described above to the use of additional optical properties of protein deposits in the retina and to the use of images as a whole for these classifications, for example of pure amyloid beta 42 versus pure alpha synuclein with an accuracy over 90% (see Provisional Patent Application No. 63/038,256, Attachment 2). The inventors contemplate that the methodology described herein and used to differentiate pure deposits of the protein amyloid beta and pure deposits of the protein alpha synuclein can also be used to differentiate deposits in which one of the two proteins predominate from deposits in which the other of the proteins predominates. The present inventors also contemplate that the deposits within the retina in which one of the proteins predominates will be differentiated from deposits in which the other protein predominates using a similar methodology. The inventors expect that, in turn, this differentiation will enable the identification of neurodegenerative diseases of the brain associated with amyloid beta as distinct from those associated with alpha synuclein.

The inventors also contemplate that the methods described herein will allow the differentiation of deposits, primarily consisting of additional proteins known to be associated with additional neurodegenerative diseases of the brain, which in turn are associated with additional proteins, likely to mirror in the retina the deposits of proteins in the brain in the presence of neurodegenerative disease(s).

That is the structure or other properties of the deposits of a given protein are likely to differ in different conditions or will potentially contain two or more proteins. This intellectual property then disclosures that the properties of this class of deposits, tissue signals and or signals from structures in retina can in turn be classified as indicative of a class of diseases or conditions involving this particular protein or combination of proteins in the nervous system or brain more generally. In addition, deposits or other expressions of a particular protein in deposits, retinal tissue and/or retinal structures may differ in the different neuro-degenerative conditions (diseases) associated with that particular protein in the retina and/or the brain. The present inventors contemplate that alpha synuclein has different interactions with polarized light and that in turn these interactions may differ with the neurodegenerative disease (associated for example with Parkinson's disease, dementia of Lewy bodies and their precursors or prodromal conditions) have different interactions with polarized light which can be documented in polarimetric images. Other dimensional and multifractal properties are also likely to have averages and distributions that differ significantly with protein type and with disease but distributions may overlap. In that case the statistical and machine learning methods outlined above can be applied. See discussion of the third classification below. Either of the two cases would lead to differences in the images or of signals from structures taken of the retina.

The third classification is the classification of retinal deposits, tissues and/or structures containing a given protein into two different groups, which in turn are associated two or more different conditions or diseases. that they are expected to be associated with. This third classification can be made either once the deposit(s) or signals from retinal tissue or structures have been classified as amyloid or not amyloid OR once deposits have been classified as containing one or another protein OR prior to either of these classifications as indicative of a particular condition or class of conditions of the retina or brain.

The deposits can first be classified as an amyloid protein (see first classification) or a combination of amyloid or non-amyloid proteins (see second classification), but now these particular protein(s) are known to be associated with a particular subset of condition(s) or disease(s). The present inventors and others have previously shown that retinal deposits of amyloid beta occur in Alzheimer's disease in anterior layers of the retina (FIG. 21) and retinal amyloid beta deposits are expected in age related macular degeneration in the posterior retinal layers. In addition, the method can be applied to differentiating amyloid beta associated with retinal vessels as a marker of cerebral amyloid angiography (CAA) from amyloid beta in retina tissue as a biomarker of other diseases. Thus, there are three specific examples of this third classification.

A first example of this classification would be the use of an identification of deposits, or properties of structures and/or tissues that contain a particular protein (e.g., alpha synuclein) via methods similar to those outlined in Provisional Patent Application No. 63/038,256, Attachment 2, could lead to a classification into an indication of the presence of one or more neurodegenerative conditions known to be associated with alpha synuclein. That is the structure or other properties of the deposits of a given protein are likely to differ in different conditions or will potentially contain two or more proteins. This intellectual property then disclosures that the properties of this class of deposits, tissue signals and or signals from structures in retina can in turn be classified as indicative of one or of a class of diseases or conditions involving this particular protein or combination of proteins in the nervous system or brain more generally. In addition, deposits or other expressions of a particular protein in deposits, retinal tissue and/or retinal structures may differ in the different neuro-degenerative conditions (diseases) associated with that particular protein in the retina and/or the brain. Either of the two cases would lead to differences in the images or of signals from structures taken of the retina.

The second example is the classification of those amyloid protein deposits (assumed to be amyloid beta because the properties observed are similar to those of pure amyloid beta deposits) in the anterior retina, assumed to be associated with Alzheimer's disease (AD) and those in the posterior retina, assumed to be associated with age related macular degeneration (AMD). In order to differentiate deposits of amyloid beta associated with Alzheimer's disease in which deposits occur in the anterior retina from the deposits of the same protein which occur in the posterior retina in age related macular degeneration), either 1) the imaging method must have sufficient depth resolution to determine whether the deposits are being seen in anterior or posterior layers of the retina or 2) other properties of the deposits must allow them to be differentiated as is taught in the current application.

Thus, if an imaging (or detection) method does not have the depth resolution to determine if deposits are located close to the anterior retina or in the posterior retina, the methods outlined allow the association with AD or AMD to be determined directly from the properties of the deposits.

The present inventors have shown in post-mortem tissue that the properties of amyloid deposits associated with the anterior retinal layers (including neural layers) which appear to be associated with Alzheimer's disease, and deposits in the posterior retinal layers (which are likely to be associated with age related macular degeneration) differ significantly in both some properties derived from their multifractal spectra (MFS) and their interactions with polarized light, and properties derived from data on dimensions and location on the retina, all demonstrated in images taken in polarimetry. This produces pixel by pixel displays of the interaction with polarized light of the two types of deposits. The present inventors have further shown that, using these properties, the deposits can be classified into two classes, those that are more anterior in the retina (and more likely to be associated with Alzheimer's disease) and those that are more posterior in the retina (and more likely to be associated with age related macular degeneration (see Provisional Patent Application No. 63/038,256, Attachment 4). This is important to live eye imaging because in many imaging methods, the depth resolution does not allow the depth position of deposits, features and signals to be known accurately.

In addition, because the inventors have shown that the properties of retinal protein deposits (presumed to be amyloid beta) differ when they are found in the anterior retina (expected location in Alzheimer's disease) compared to when they are found in the posterior retina (expected location in age related macular degeneration), the present inventors also demonstrated that the interactions with polarized light of retinal deposits can be used to differentiate between the properties of retinal deposits (both containing amyloid beta) formed in association with Alzheimer's disease and in association with age related macular degeneration (see Provisional Patent Application No. 63/038,256, Attachment 4). More precisely, presumed amyloid deposits imaged in post-mortem retinas in the anterior retinal layers form images in polarized light and have differing interactions with polarized light than presumed amyloid deposits imaged in post-mortem retinas in the posterior retina. Furthermore, using machine learning algorithms, the inventors have been able to accurately differentiate the anterior deposits (presumed to be associated with Alzheimer's disease) from the posterior deposits (presumed to be associated with age related macular degeneration) without knowledge of where they were physically located. This important as not all methods of optically imaging the retina can resolve the position in depth of an imaged deposit.

More generally in this third classification, the present inventors teach that it is possible to differentiate a condition in which a specific protein forms deposits which occur in the anterior retina (e.g., amyloid beta in either Alzheimer's disease or glaucoma) from the deposits of the same protein which occur in the posterior retina in another condition (amyloid beta in age related macular degeneration). By extension, the present inventors expect deposits in the anterior retina in association with glaucoma to differ from those in the anterior retina associated with Alzheimer's disease.

A third example of this third classification involves the classification of retinal deposits or signals from retinal structures and/or tissue as associated with amyloid beta which in turn is either associated with Alzheimer's disease pathology in the retina and/or the brain or as associated with cerebral amyloid angiopathy (CAA) in the retina/and or the brain. Deposits with polarization properties consistent with amyloid beta interactions with polarized light located in close proximity to or within blood vessels in the retina are presumed to be potentially associated with Cerebral amyloid angiopathy (CAA), a condition in the brain, a hallmark of which is the deposit of amyloid beta in the blood vessels of the brain.

The present inventors and others have found deposits in blood vessels with increased contrast in polarimetric imaging and also positive in thioflavin S staining of post-mortem retinas of those who have received a diagnosis of cerebral angiopathy (CAA) in the post-mortem brain and also when there is no CAA brain pathology. CAA and AD often but not always occur together. Importantly CAA comes with an independent risk of stroke, in addition to any other risk factors. This makes it important to predict its presence in the brain separately from AD.

The present inventors' work on post-mortem tissue has clearly shown that there are two morphologies of amyloid (likely amyloid beta) deposits in the retina which can be distinguished-those in tissue presumably associated with Alzheimer's disease and those in or associated with vessels associated with cerebral amyloid angiopathy (see FIGS. 11A, 11B, 11C, 11D, 12A, 12B, 13, and 14 of the present application). There are differences found in their morphology, including their shape and also in their lack of association with vessels (in deposits that appear to be associated with the type of pathology expected in Alzheimer's disease) and that expected in CAA, which are expected to be associated with vessels. It is also likely that other properties of the image of a given deposit or the image a part of the retina in which a deposit occurs will differ in its properties. Examples of differences in morphology of deposits in amyloid deposits in retinal tissue and amyloid deposits associated with vessels are given in FIGS. 11A, 11B, 11C, 11D, 12A, 12B, 13, and 14, of the present application. This disclosure then teaches that they could be classified into these two groups using combinations of these properties.

In the case where amyloid is evident in the blood vessel of a living eye in the presence of a blood column, the classification of CAA from other diseases involving amyloid is simplified.

When amyloid fills capillaries or breaches a vessel wall, diagnosis in the retina of CAA may be more difficult. Thus, classification of amyloid deposits (assumed to be amyloid beta) deposits based on their properties as associated with cerebral amyloid angiopathy (CAA) or associated with AD is especially needed when the deposits have impeded blood flow or damaged vessels to the extent that their location within the wall or lumen of a vessel is not immediately apparent but properties of the deposit will allow its classification as associated with either CAA or AD type pathology. A third examples would be deposits of alpha-synuclein, expected in a number of different neurodegenerative diseases which are also likely to have differing properties as a function of the specific disease. Similarly in other cases, multiple neurodegenerative diseases are associated with a given one or more proteins which are likely to have differing properties in each disease.

The fourth classification is the classification of the severity of a condition or disease. In the fourth classification, once the condition or disease has been classified or potentially simultaneously with one or more of the previous classifications, further properties of the deposits, tissues and structures containing a specific protein or combinations of proteins, other properties such as their number and position in the retina, signal intensity (or any combination thereof) can be used to specify the severity of the condition or disease. The fourth classification can be made following any combination of the previous three classifications or it can be made directly.

Th present inventors also extend the methods disclosed herein to predicting the severity in the brain of each of the conditions mentioned above. In the fourth application of the classification methods outlined, they can be used to separate amyloid deposits in the retina for a lower severity of disease from amyloid deposits associated with a higher severity of disease. This is shown in an example applied to the severity of AD, described in the inventors' previous patent. Herein the present inventors teach that this can be generalized to more retinal and brain conditions, including but not limited to age related macular degeneration as an example of a neurodegenerative retinal condition, and to neuro-degenerative diseases of the brain (which may also have retinal and visual impacts) including but not limited to Alzheimer's disease and cerebral amyloid angiopathy, a disease of the brain which we and others have also show occurs in the retina (see FIGS. 11A, 11B, 11C, 11D, 12A, 12B, 13, and 14 of the present application).

In first example of the application of the fourth type of classification, previously, we had taught a method for this in previous patents for classifying the severity of Alzheimer's disease. The inventors' had shown in their analysis of amyloid protein deposits in association with Alzheimer's disease in post-mortem retinas, that the number and density of such deposits in the retina are a marker of and correlate with the severity of amyloid in the brain and of the overall severity of Alzheimer's disease pathology in the brain. In an analogous fashion, the number, density, size or some measure of severity of amyloid beta protein deposits found in the retina in association with other conditions (as previously stated, including but not limited to: glaucoma and age-related macular degeneration) are expected to predict the severity of disease in the retina. More generally, the number, density, size or some measure of severity of other protein deposits found in the retina in association with other neurodegenerative conditions is likely to predict the severity of those conditions in the brain.

Here, in a second example of the fourth classification, we also teach that the severity of cerebral amyloid angiopathy (CAA) within the blood vessels of the retina can also be categorized from images of amyloid protein within the blood vessels of the retina (see FIGS. 11A, 11B, 11C, 11D, 12A, 12B and 13 of the present application) and that this classification can predict severity in the brain. The inventors' initial images in post-mortem retina were taken using thioflavin dye but the inventors have also discovered that deposits in the blood vessels have visible polarimetric signals. Thus, in the living eye, these images could be taken using the inventors' polarimetry methods described in previous patents as well as using amyloid protein specific dyes such as curcumin, and other optical methods that are known to result in a signal from amyloid proteins in general or amyloid beta in particular. The inventors' polarimetry method has the added advantage of making the vessel wall more visible, simultaneously with any protein deposits inside or outside the vessel. This will be most important in live eye imaging when the protein deposit has blocked or damaged the vessel wall in such a way that the vessel no longer contains a blood column.

Therefore, the presence of an amyloid deposit within a blood vessel, indicative of CAA, can be differentiated by its proximity to a blood vessel wall and between two walls, visible in optical images, including in polarimetry images due to the known polarimetric signal from amyloid in the vessel wall.

As the present inventors first showed in Alzheimer's disease, CAA is also an example where the disease in the retina appears to mirror and have the potential to predict the presence and severity of the disease (CAA) in the brain. The work of the inventors has shown that several subtypes of amyloid deposits in the vessels or in close proximity to the vessels do predict the presence of and severity of CAA in the brain for the patients investigated to date using post-mortem tissue. Other types of deposits seen in or associated with retinal vessels may also predict severity of CAA in the brain. More generally, it is likely that the presence of protein deposits in the retina closely associated with vessels and one or more of their properties (including but not limited to strength of one of more polarimetric signals, or other optical interaction with light), size, shape, morphology of the deposits number of vessels affected or the deposits interaction with adjacent tissue, can predict the severity of the disease in the brain (see severity scales below).

The present inventors present a method for categorizing the severity of amyloid (presumed amyloid beta deposits) in retinal vessels. The number, density, size or some measure of severity of amyloid beta protein deposits found in the retina (in association with a few or many retinal vessels), is expected to well categorise severity in the retina and to predict the severity of said disease (CAA) in the brain; as a biomarker of cerebral amyloid angiopathy (CAA) in the brain. This severity scale, potentially in combination with the number or area or length of vessels demonstrating this severity in the various regions of or in the complete retina, potentially with other properties of the deposits, will predict the severity of cerebral amyloid angiopathy (CAA) or related pathologies (e.g., strokes caused by CAA) in the brain. This classification of disease severity in the retina and from these results, the likely prediction of in the brain could be made into three classes-none, mild and more severe or categorized into up to 6 (or potentially more) categories of severity in the brain.

The present inventors present a specific example for categorizing the severity of amyloid (presumed amyloid beta deposits) in retinal vessels as a biomarker of cerebral amyloid angiopathy (CAA) in the brain and its severity. The present inventors teach that a severity scale within a vessel or vessels, described herein, potentially in combination with the number or area or length of vessels demonstrating this severity in the various regions of or in the complete retina, potentially with other properties of the deposits, will predict the severity of cerebral amyloid angiopathy (CAA) or related pathologies (e.g., strokes caused by CAA) in the brain. This prediction of classification of disease severity in the brain could be made into three classes-none, mild and more severe or categorized into up to 6 (or potentially more) categories of severity in the brain.

The present inventors propose a severity score be assigned to the severity of CAA type changes in vessels in the retina as the following or any modification of this numeric scale: an example of a severity score of vessel amyloid pathology assigned to them according to the following classification: 0) no evidence of CAA pathology in the vessel; 1) amyloid within a vessel but nowhere appearing to be circumferential around the vessel 2) those where amyloid in cross section is circumferential around the vessel and 3) amyloid both within a vessel and outside and touching the vessel which appears to fulfil the definition of a dysphoric amyloid deposit as found in the brain.

In the case of CAA in the retina, the present inventors disclosed herein a severity scale based on the morphology of the amyloid deposits in the retina that we have observed, listed above. This scale may or may not in turn be weighted by the number of blood vessels across the entire retina in which a given score occurs, the number of vessels in any sampled subsection of the retina in which a given score occurs, the length of the vessel along which a given score occurs, the maximum severity seen in a given vessel or region of the retina or any combination of the above to give an overall score of severity within a given retina. In turn the scores from the left and right retinas could be combined in any weighted sum, including just considering one retina. It is then expected that one or more of the severity scores calculated as described will predict the severity of CAA in the brain and potentially the risk of stroke associated with said severity of CAA score. Any analogous scale of scores of the severity of amyloid presence in the retinal vessels could also used in this way, combined with or without a classification algorithm.

Here we also teach that the severity of cerebral amyloid angiopathy within the blood vessels of the retina can also be categorized from images of amyloid protein within the blood vessels of the retina (see FIGS. 11A, 11B, 11C, 11D, 12A, 12B and 13 of the present application). These are images of post-mortem retina, taken using thioflavin dye. The present inventors propose that, in the living eye, these images could be taken using the inventors' polarimetry methods described in previous patents as well as using amyloid protein specific dyes such as curcumin, and other optical methods that we have, in previous patents taught would result in a signal from amyloid proteins in general or amyloid beta in particular. The inventors' polarimetry method has the added advantage of making the vessel wall more visible, simultaneously with any protein deposits inside or outside the vessel. This will be most important in live eye imaging when the protein deposit has blocked or damaged the vessel wall in such a way that the vessel no longer contains a blood column.

Deposits which are within the blood vessel, earlier in CAA should be apparent in live eye imaging because they occur between the blood column and the outer vessel wall which will both be apparent in almost any method of optically imaging the retina with sufficient resolution. The inventors' have confirmed the previously reported positive polarimetric signals from the surfaces of the blood vessels in the retina, reported to originate from collagen and/or muscle in the walls of blood vessels, reported by others include collagen and muscle fibres. Thus, optical imaging methods, including polarimetry can be employed to make these deposits visible and to differentiate them both from the walls of the vessels and from other potential deposits in the vessels of the retina for example and plaques in cerebral vascular disease, also visible in polarimetry. The signals in the retinal vessels, which we categorised as related to CAA in the retina, from individuals with brain CAA, were thioflavin positive as well as positive for some polarimetric properties. This indicates that the polarimetric signals were coming from amyloid protein deposits, associated with the vessels analogous to the hallmark that occurs in brain CAA. The present inventors have shown that polarimetric properties of the vessel wall and the amyloid protein deposit within differ. These signals and their apparent position with respect to the signals originating from amyloid protein deposits within the vessels, allow an accurate visualization of the deposits as inside of outside a vessel. Because the deposits can be sparse, following imaging, segmentation of the blood vessels and increased magnification of candidate areas of the vessels should be undertaken.

The significance of the amyloid deposits that the present inventors found n the retina which appear to fill a vessel like structure in predicting the severity of CAA in the brain remains to be determined. There are no reports of analogous structures in the brain, except when amyloid protein fills capillaries.

In CAA in the brain, amyloid deposits which are most severe are the ones which initially form in between the inner and outer blood vessel walls and then breach the outer wall of the vessel (referred to as dysphoric deposits). These deposits in turn increase the probability of a major bleed in the brain, the most severe complication of CAA in the brain. These deposits in category 3 are inferred in the retina when a deposit is in the retinal tissue, appears to be touching the vessel wall and there is also evidence of a deposit in the vessel. The present inventors have observed such deposits (FIG. 13) in the retina and they are likely to infer a high severity of CAA in the brain.

Later stage deposits that either fill a capillary (as occurs in CAA in the brain) or are dysphoric may be more difficult to differentiate from retinal deposits containing amyloid beta which are close to but completely outside the vessel in the adjacent tissue. Here, we teach that methods analogous to those above applied to differentiate retinal amyloid retinal deposits and their characteristics in Alzheimer's disease from those seen in age related macular degeneration can be applied to differentiate deposits found in the anterior retina in CAA that fill capillaries or are dysphoric (inside and outside) the vessel from those deposits in the anterior retina not in association with blood vessels but in association with Alzheimer's disease.

The steps in applying the methodology to confirm the presence of CAA type deposits or to categorize the severity of said deposits consists of images of the vessels and analysis of any optical signals, including polarimetry, which are consistent with the presence of amyloid beta within the walls of the vessel. Higher magnification or an additional imaging method is then used if needed to determine the extent of the amyloid within the vessel and whether the amyloid is circumferential within the vessel. The steps in analysis of potential CAA deposits filling capillaries or dysphoric or candidate dysphoric deposits located immediately adjacent to a vessel. would use the same steps as in the differentiation of deposits in Alzheimer's disease from those in AMD. The classification of amyloid (assumed to be amyloid beta) deposits based on their properties as associated with cerebral amyloid angiopathy (CAA) or associated with AD. is especially needed when the deposits have impeded blood flow or damaged vessels to the extent that their location within the wall or lumen of a vessel is not immediately apparent but properties of the deposit, including but not limited to morphology and polarimetric signals, will allow its classification as associated with either CAA or AD type pathology.

Properties of the deposits used for all of the classifications described in the previous paragraphs on CAA include one or more of: polarimetric properties (indicative of interactions with polarized light), texture properties derived from the properties of multifractal spectra or other fractal analysis and properties related to dimensions and location in the retina or in substructures or specific locations in the retina tissue and/or a vessel. Other properties derived from polarimetric and other optical imaging modalities applied to the retina to give images of the deposits or to sense the properties of the light returning from the retinal (including tissue and vessels) and/or other structures in the retina or images themselves taken in different imaging modalities could also be used in a similar manner.

The present inventors and others have found that amyloid deposits are often sparsely distributed within blood vessels. For the purpose of identifying the severity and differentiating whether the deposit is circumferential around the vessel, an optical method which spatially resolves an optical signal from the vessel is important. Also important is the ability to refocus in depth through the vessel.

The present inventors have a large database of the characteristics of amyloid deposits in the anterior retinal tissue, found in association with Alzheimer's disease in post-mortem retinal tissue. Once there is a large enough number of samples of the morphology and optical signals associated with CAA deposits which are in turn as discussed previously associated with vessels, this number of deposits and their characteristics, including interaction with polarized light, for deposits in post-mortem tissue where they can be microscopically confirmed to be CAA dysphoric or capillary CAA deposits, we teach that the methodology already described to distinguish and classify whether individual deposits are associated with CAA or with AD. The present inventors teach that the methods of machine learning and AI, used to distinguish deposits due to AD from those due to AMD (FIG. 16) will also distinguish deposits associated with AD from those associated with CAA. The present inventors expect these methods to have high accuracy. The present inventors teach that the use of polarimetric and fractal properties, potentially supplemented by shape parameters is likely to result in a successful differentiation. Images (FIGS. 11A, 1B, 11C, 11D, 12A, and 12B, as compared to FIG. 13) show distinct differences in morphology.

Here we teach that that the methods described above for categorizing the severity of disease in the retina from the number of deposits, their severity as defined by size, morphology, fractal properties, interaction with light to give polarimetric properties, images taken in polarized light and any other measured or imaged interaction with light of protein deposits expressed in said disease, can be generalized to give severity of the disease in the retina for additional retinal and brain conditions, including but not limited to age related macular degeneration, and glaucoma, which are diseases of the retina. In addition, the severity of expression in the retina of any other neuro-degenerative disease of the brain (which may also have retinal and visual impacts) can also be categorized using analogous methods. The present inventors have already taught that the polarimetric signals from alpha-synuclein are different from those associated with amyloid beta. Following the steps described for the categorization of alpha-synuclein deposits, previously described could be followed by the categorization of the severity of an associated disease by studying and classifying the changes in properties with disease severity. In addition, the severity of expression of said diseases in the brain can be predicted from the severity of the disease or expression of protein deposits in the retina or from a subset of said severity classification.

Examples of each of the categorizations are found in retinal vessels were given in FIGS. 11A, 11B, 11C, 11D, 12A, 12B and 13 of the present application. As more examples are imaged, these categories could be further subdivided, expanded or amalgamated giving slightly different scale ranges. It is not clear as yet whether or not amyloid appears to completely fill the lumen of a vessel at some point along its length. If confirmed, it could be added to the severity scale. However, capillaries filled with amyloid could be expected to mirror this pathology in capillaries in the brain.

From the study of some retinas, for which the brain severity of CAA was known, we have shown that certain types of morphologies of amyloid deposits in the retinal vessels appear to correlate with the diagnosis of CAA in the brain. These include deposits that appear to occur between the vessel walls in small amounts, forming lines inside the vessels which can be either circumferential or non circumferential (see grades previously listed). As a result of the inventors' work comparing the brain diagnosis and severity of CAA as found post-mortem in the brain with the severities assigned to the CAA type morphology found in the retinas of the same individuals, categories 0,1, and 2, defined above in the retina appear to predict similar severities of pathology in the brain. Once more examples have been analysed, the strength of the prediction of the brain CAA pathology for the retinal pathology is expected to improve and severity 4 in the retina may correlate with severity in the brain.

Figure 14:
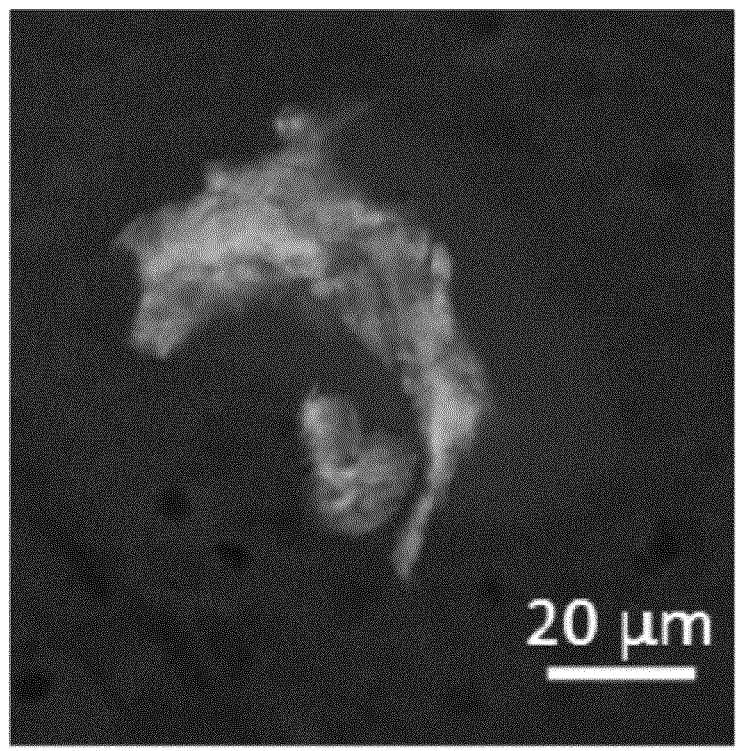
FIG. 14 is an amyloid deposit in retina stained with thioflavin S and not associated with a blood vessel. The shapes of these deposits differ from those within or closely associated with blood vessels. The scale bar is 20 µm.
Figure 15:
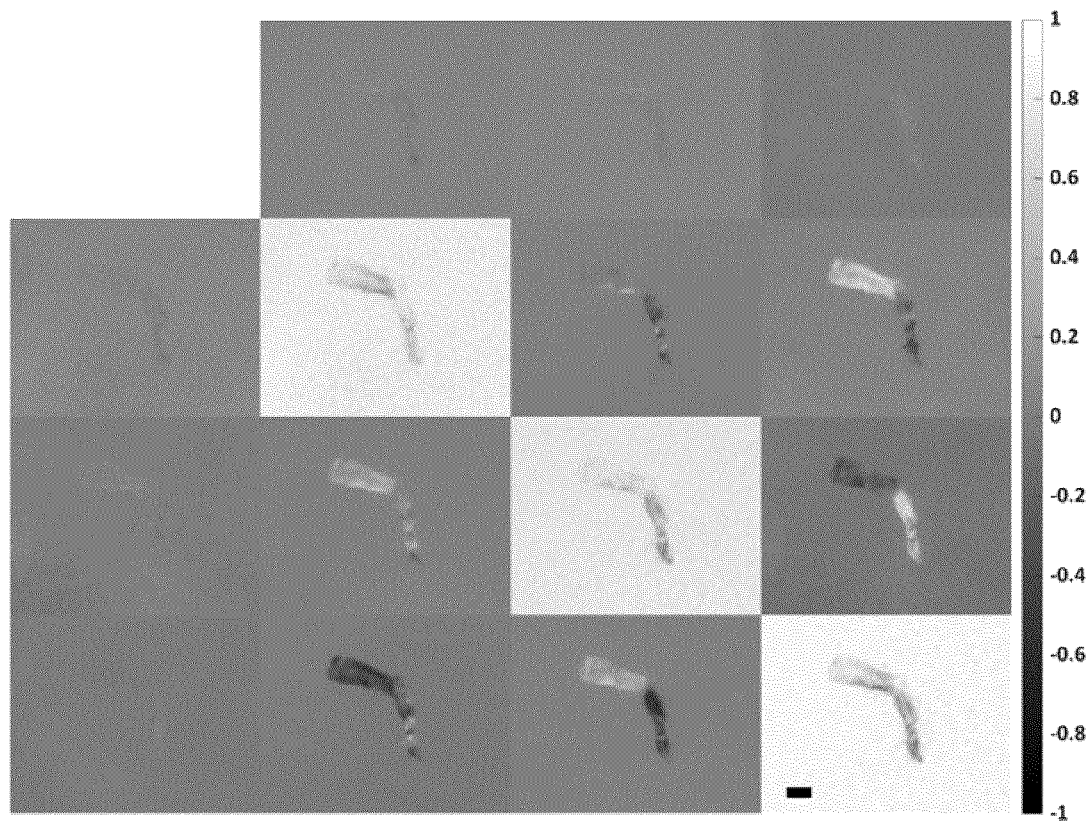
FIG. 15 is a spatially resolved Mueller matrix (MM) of a polarimetric and fluorescence positive deposit. Elements are coded by row and column number, going from left to right and then down row by row and each pixel position has 16 elements associated with it. The matrix elements are normalized by the first element in the upper left which is then has a value of 1 at all pixels. From this spatially resolved matrix, we can calculate the interactions of the material at every pixel with polarized light. A retinal protein deposit that interacts with polarized light differently than the surrounding retina is evident in the FIG. Pixel values are between -1 and 1.
Figure 16:
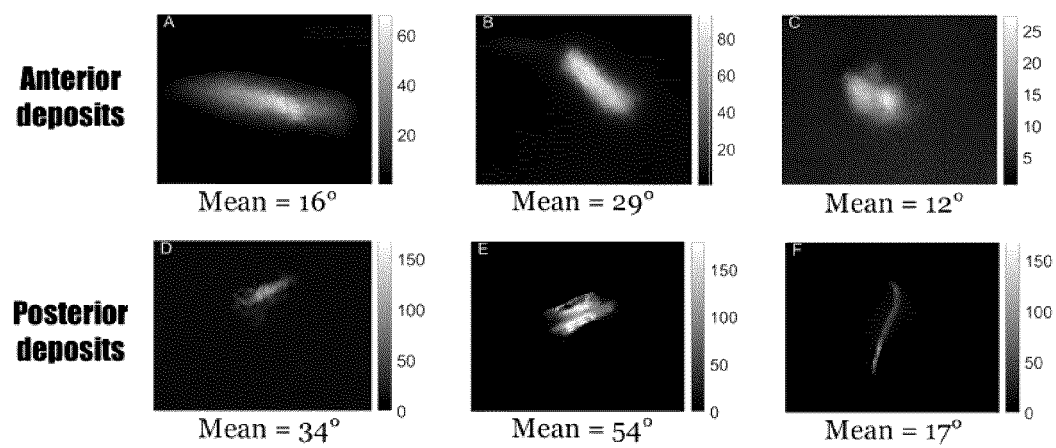
FIG. 16 is the Linear retardance, an interaction with polarized light across six sample deposits three found respectively in the anterior retina (top half of the FIG.) and in the posterior retina (bottom half of the FIG. Note that the means across anterior and posterior deposits overlap and were not significantly different but that the textures appear to differ. Multifractal spectra were also derived from these images (See FIGS. 18A and 18B).
Figures 17, 18A:
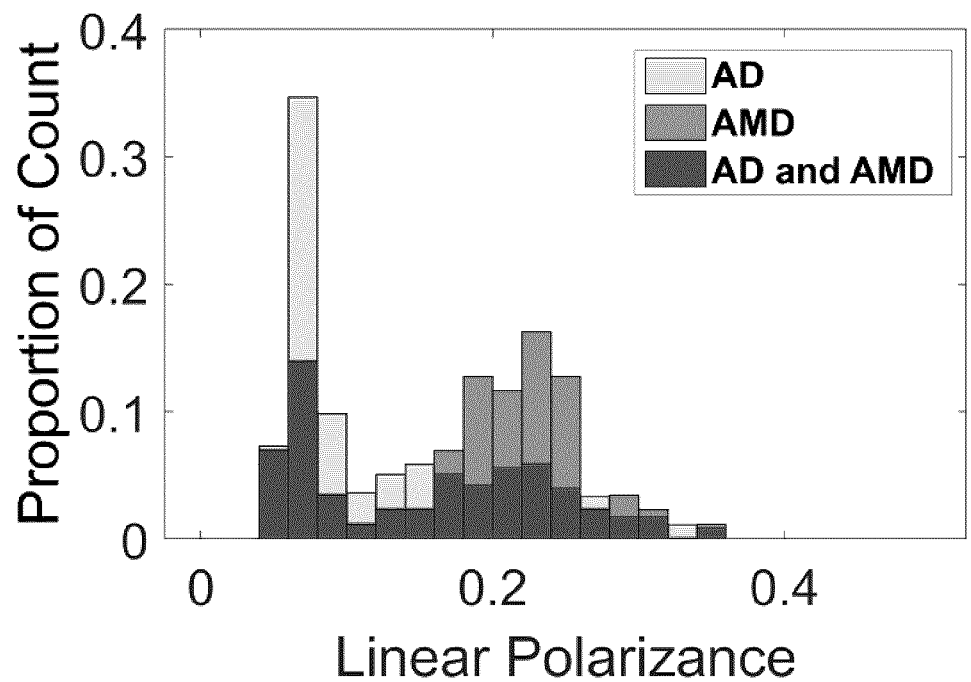
FIG. 17 is of histograms of linear polarizance, one of 16 polarimetric properties considered for the linear discriminant analysis performed between anterior and posterior deposits. Either the means or distributions were significantly different in 3 properties. The histograms, shown here are in pale grey for anterior deposits (presumed to be associated with AD) and in mid-grey for posterior deposits (presumed to be associated with AMD). Dark grey indicates an overlap of the histograms. Means and differences in polarizance between anterior and posterior deposits were borderline for a difference after Bonferroni correction for multiple testing.
FIG. 18A is of multifractal spectra for texture analysis, shown for 3 amyloid deposits in the anterior retina with their spectra labelled A, B, C, corresponding to deposits previously shown in the top row of FIG. 16, running from left to right.
Figure 18B:
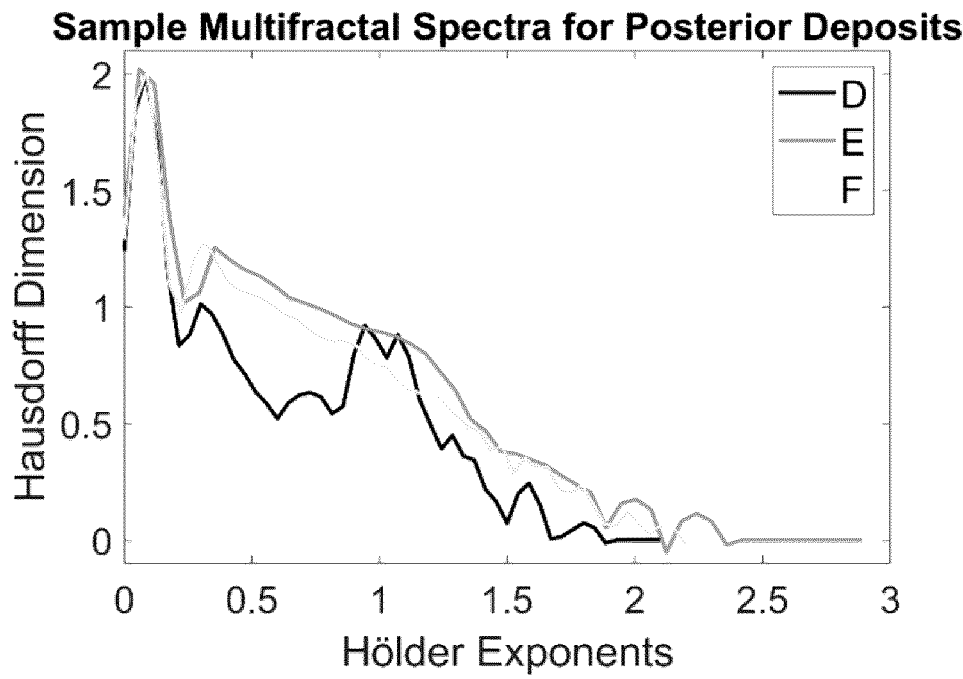
FIG. 18B is of multifractal spectra for texture analysis, shown for 3 amyloid deposits in the posterior retina with their spectra labelled D, E and F, corresponding to deposits previously shown in the bottom row of FIG. 16, running from left to right.
Figure 19:
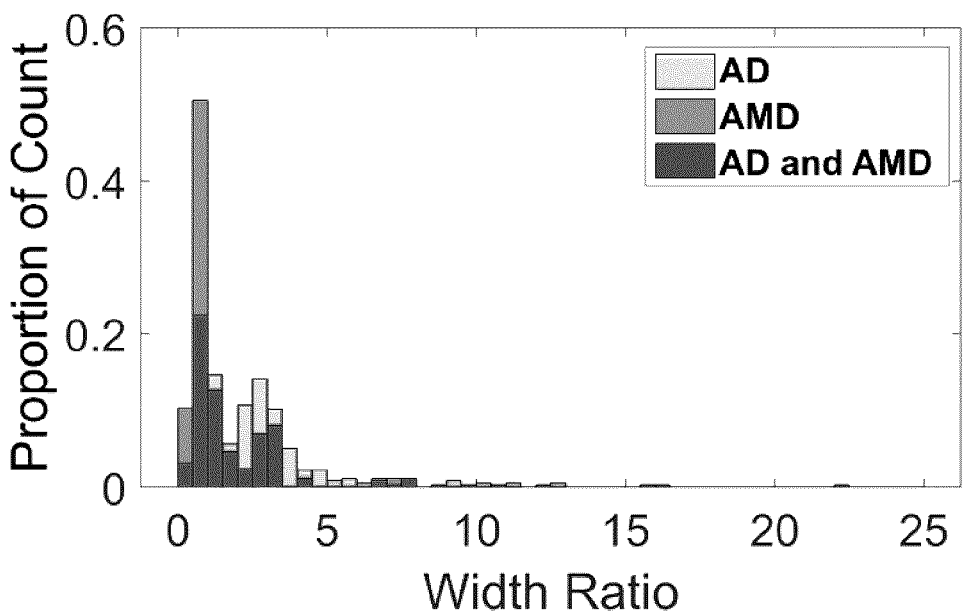
FIG. 19 is a histogram of the mean of the width ratio of the two most prominent peaks of the multispectral spectra, in light grey for anterior deposits (presumed to be associated with AD) and mid grey for posterior deposits, (presumed to be associated with AMD). Dark grey indicates an overlap of the histograms. The means and distributions for the width ratio of the two most prominent peaks differed significantly between presumed AD (anterior) and AMD (posterior) deposits. In total, 7 spectral properties considered for discriminant analysis (DA) had means or distributions that differed significantly. Deposit area also differed significantly between the two groups.

These predictions of severity of brain disease in CAA from the protein deposits in the retina is analogous to prediction of the amyloid (primarily amyloid beta deposits) found in the brain, related to AD from the amyloid deposits in the tissue of the retina (see FIG. 14). These protein deposits also display positive polarimetric signatures. The retinal protein deposits associated with AD do not fit the definitions above which distinguish deposits associated with CAA. Thus, any deposits in the anterior retina with the morphologies previously observed in individuals with Alzheimer's disease (AD) would be classified as associated with AD. Thus, the inventors' classification methods, allow us to classify protein deposits in the retina as being associated with AD versus CAA (see FIGS. 11A, 11B, 11C, 11D, 12A, 12B, 13, and 14 of the present application). for obvious differences in deposit morphology in the two conditions.

Extension of Methods of Caterization Described

These novel methods are particularly important in imaging of the living eye with the intent to detect or diagnose or predict the occurrence of any condition for which amyloid or other protein deposits are biomarkers. As well as AD, AMD, CAA, and neurodegenerative diseases associated with alpha-synuclein mentioned explicitly above, there are many other neurodegenerative diseases that are associated with protein deposits in the brain where in turn, the associated pathological condition could be identified by the presence of protein deposits in the retina. Imaging in polarimetry is likely to show different signatures for each of these proteins as well as for amyloid protein deposits in association with different conditions. Thus, the methods outlined above are applicable to differentiating the images of amyloid proteins associated with different diseases as well as nonamyloid proteins. The present inventors have demonstrated that the polarimetric signatures of the pure protein amyloid beta 42 (associated with Alzheimer's disease and its precursors) and alpha synuclein (associated for example with Parkinson's disease, dementia of Lewy bodies and their precursors or prodromal conditions) have different interactions with polarized light which can be documented in polarimetric images.

Other dimensional and multifractal properties are also likely to have averages that differ significantly but distributions which overlap. In that case the statistical and machine learning methods outlined above can be applied. Here we also disclose how to combine the values of polarimetric, dimensional and multifractal spectral and fractal properties to differentiate those that indicate more severe disease compared to less severe disease (either as result of the properties possessed by the deposits or their numbers or distribution in each of the two or more cases of severity). This could in turn be extended to any other disease for which there are amyloid deposits in the retina, including but not limited to CAA and other neurodegenerative diseases (NDDs). It also discloses how to classify a class of deposits associated with one disease (AD) from another (AMD), that is as described above.

By extension, we expect that the same techniques and approaches as derived here will allow us to differentiate additional proteins in the retina expected to be associated with many additional neurodegenerative diseases of the brain. With an extension of these methods, we also deduce that other degenerative diseases of the retina with which protein deposits have been associated (in the retina) for example glaucoma in which deposits containing amyloid beta have been found, will also be able to be differentiated according to the properties of the interactions of said deposits with polarised light.

More Detailed Methods

As the intent is to either identify a known protein in a particular location, or to differentiate between two or more proteins, the signals resulting from each of the imaging modalities enumerated above are mapped across the retina as an image to identify areas with differing signals (and potential deposits) of differing types. The signals are then compared with the known signals from the proteins of interest; particularly signals which are known to differ among proteins of interest. Or the signals can be compared with signals previously obtained from post-mortem tissue using a gold standard marker (for example fluorescence) with good depth and lateral resolution, and analogous optical imaging techniques are used, and where the deposits can be confirmed as associated with a particular condition. This differentiation of signals as from deposits in a particular position and by inference, associated with a particular disease or condition uses properties of the deposits described above and can be assisted by a machine learning or other type of artificial intelligence algorithm as described in the authors' intellectual property and herein.

The second step (if needed) is to zoom into areas which show the presence of one or more signals, consistent with one or more proteins from the expected area (and or depth) with higher magnification and then assess the shape and size characteristics as well as strength and spatial distribution of the optical signals from within the previously identified areas and compare these signals with the known signals of a particular type of protein, found in conjunction with a particular condition or disease. An adaptive optics correction if needed is used to achieve the needed lateral resolution. Again, in this step, this differentiation of signals as from deposits in a particular position and by inference, associated with a particular disease or condition uses properties of the deposits described above and can be assisted by a machine learning or other type of artificial intelligence algorithm as described in the authors' intellectual property and herein.

As a specific example of the classification of the deposits both expected to contain predominantly amyloid beta in the anterior retina (presumed to be associated with Alzheimer's disease) from the deposits in the posterior retina (presumed to be associated with age related macular degeneration), deposits with optical properties consistent with being composed of amyloid beta in each of the two locations were imaged in post-mortem retinas, using optical methods which concentrated on polarimetry images.

The use of a difference in polarimetric properties, polarization images, deposit location and dimensional (including fractal properties) properties associated with shape and size to determine the severity of AD and/or AMD has been disclosed in United States Patent No. S,914,9184, which is incorporated herein by reference in its entirety. What is new in the present application is the specific methods used to classify the different conditions, the use of machine learning and other classification methods and the use of additional properties including multifractal spectral and/or fractal properties. The present inventors have shown that deposit multifractal properties also differ with the severity of AD in addition to specific polarimetry and dimensional properties. Analogously changes in these properties could be used to assess the severity of AMD. The conditions differentiated now explicitly include AD, AMD, classes of diseases associated with alpha-synuclein and CAA and each can also be classified by severity. The present inventors have also taught that any other neurodegenerative disease that expresses protein deposits in the retina could be differentiated from other conditions using the methods outlined and could also be classified by severity.by severity. As above, the inventors' methods can be extended to use other well-known statistical methods, machine learning or artificial intelligence approaches can be taken to separate deposits to give a prediction of the severity of disease.

The methods described could in turn be extended to any other disease for which there are amyloid or other protein deposits in the retina, including but not limited to other neurodegenerative diseases (NDDs). It also discloses how to classify a class of deposits associated.

Properties and Machine Learning Methods Used

Figure 21:
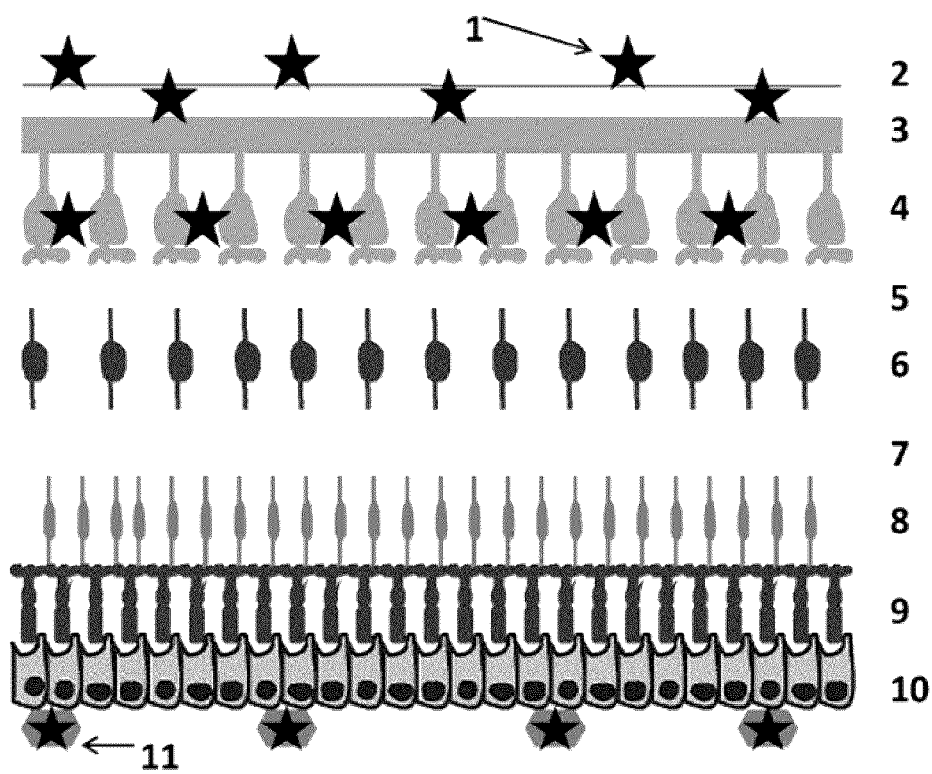
FIG. 21 is a schematic of the cell layers of the retina (numbered 2-10) that shows the positions in which deposits of amyloid beta, schematically shown as stars, (1) have been found in the inventors' study of postmortem retinas and studies by others of animal postmortem retinas. These amyloid deposits, some of which have been shown to contain amyloid beta associated with Alzheimer's disease, occur close to the top surface of the retina (inner limiting membrane, 2), or below 2 in the anterior retinal layers, associated with the neural cell layer of ganglion cells (4) and their nerve fibres (optic nerve fibre layer, (3)). There are also Mueller cell feet that form 2 and with which some of the amyloid deposits may be associated. In animal models, sparse deposits have been found in other layers (5, 6, 7), in association with Alzheimer's disease and its prodromal stages. The inventors have shown that the number of amyloid deposits in the anterior retina (layers 1 to 6) predicts the severity of amyloid in PET scans and the overall severity of brain pathology associated with Alzheimer's disease.

Deposits in the anterior retinal tissue with characteristics of amyloid beta interactions with polarized light are presumed to be associated with Alzheimer's disease and its prodromal stage and its precursors. Deposits in the posterior retina with characteristics of amyloid beta interactions with polarized light but are presumed to be associated with age related macular degeneration or its precursors (FIG. 21). The present inventors have shown that the interactions of these two groups of deposits with polarized light and their fractal properties differ. We further deduce that the interactions with polarized light of retinal deposits can be used to differentiate between the properties of retinal deposits, with similar composition but associated with two different conditions.

The present inventors then used a machine learning method known as convolutional neural networks to classify the deposits into two classes on the basis of their differing properties, including properties derived from their interaction with polarized light and the fractal properties of these polarization properties when represented as an image. The present inventors showed that the deposits which occurred in the anterior retinal layers and were presumed to be seen in association with Alzheimer's disease could be classified and separated from those deposits which occurred in the posterior retina and were assumed to be associated with age related macular degeneration using the polarimetric properties (interaction with polarised light) and multifractal spectral properties of images of the deposits derived from images taken in polarized light. Potentially other properties evident in a given optical imaging modality (including size, shape and other interactions with light) used to image the retina using the classification techniques described herein or any other known classification techniques. Herein the inventors' extend their previous approach from polarimetry and other optical signals and properties derived from data on dimensions and location on the retina to include the use of properties of the multifractal spectra or other fractal properties of deposits (see Provisional Patent Application No. 63/038,256, Attachment 4), as well as to the use of additional optical properties of protein deposits in the retina, including but mot limited to interactions with light enumerated herein.

From these images of protein deposits taken in polarized light as described the properties of interaction of the deposits with light can be defined, including as way of example, the preferential absorption of a particular state of polarized light (diattenuation) or the differential change in velocity of light of a particular state of polarized light (retardation or retardance), In turn these properties can be plotted across the deposit and the surrounding retina. The resulting "images" or the polarimetric properties of the deposits visible in the images can be used to differentiate the type of protein deposit and/or the disease or condition associated with it.

The classification techniques were described in the materials submitted with the provisional patent and herein in the preferred implementation but are not limited to said techniques. Any currently known or future improvement of a machine learning or artificial intelligence method of classification or closely related technique could be used to improve the classification of deposits.

Moreover, the principles of this work can be extended to other interactions of the protein deposits with light in other ways during imaging of the retina with light. For example, in defining the polarimetric properties, the inventors have used the raw images taken when different light polarizations are incident onto the deposits and the captured light is filtered by additional optical elements that interact with polarized light. In the classification successfully completed, the images used were of a few traditional polarimetric properties: linear retardance, linear diattenuation and linear anisotropy, defined pixel by pixel across the image which were very successful at the classification. Any other individual or combination of polarimetric properties defined pixel by pixel could also be used, as well as the raw images taken, the Mueller matrix calculated from the raw images or any equivalent combination of these. See FIG. 15 for a Mueller matrix mapped pixel by pixel calculated across an image of a protein deposit after aligning the individual images taken. The deposit is visible against the background retinal tissue in many of the 16 elements of the Mueller matrix.

Techniques Common to the Classifications and Differentiation Described and Imaging For each of the methodologies to differentiate protein deposits, optical techniques need to be chosen to obtain the images that are then used to complete the analysis described above. Methodologies introduced by Campbell in previous intellectual property can also be combined with the new methods described herein and the imaging methods disclosed can be used on the living human and animal retina in order to find, characterize and possibly treat protein deposits associated with a number of different conditions and or diseases. As previously described by Campbell, it is a good idea to target areas of the retina in which protein deposits associated with a particular disease and or condition are more likely to be found in order to find what may be sparse deposits without an unreasonably long imaging session. For instance, if amyloid beta in age related macular degeneration is to be imaged, the posterior half of the retina plus retinal pigment epithelium (RPE) should be imaged whereas if amyloid beta deposits in Alzheimer's disease or glaucoma or those containing alpha synuclein are to be imaged, images close to the surface of the retina with sufficient depth resolution to differentiate the anterior layers of the retina (including the retinal nerve fibre layer (NFL) and the ganglion cell layer (GCL) from underlying neurons from the more posterior layers should be taken (FIG. 21). As previously disclosed, ideally, imaging of protein deposits in the retina involves en face scanning of a relatively large area of the retina, reasonably rapidly which preferably in humans in a preferred implementation should extend at least 100 degrees along the horizontal, ±50 degrees nasal and temporal to the optic nerve head along the horizontal, with imaging at least ±20 degrees to the horizontal. In earlier disease, deposits are likely to be scarce and the imaged field of view may need to be larger. The work of Campbell's group in imaging post-mortem retinas of those with Alzheimer's disease has shown an almost uniform distribution of amyloid deposits per unit area of retina. If protein deposits in other retinal and/or neurodegenerative disease of the brain are not distributed as uniformly, imaging fields may need to be chosen dependent on the disease and type of protein deposit suspected. With increased experience in this imaging, the areas of the retina could be adjusted to those in which a particular type of protein deposit is first found during the course of the disease of interest or to those to which the disease is most likely to appear first or to those to which the disease is most likely to progress over time. What is key in this first imaging step is that the imaging beam covers a large percentage of the full area so that no small sparse deposits are missed. Secondly the signal measured must be that coming from the layers appropriate to the protein deposit being imaged (FIG. 21).

In the optical imaging performed above using any of the methods as described below, the beam of light returning from the eye is analysed for a candidate marker of the protein(s) for which one is imaging. Candidate markers include spectroscopic signals, hyperspectral signatures, polarization signals indicating interaction with polarized light, optical path differences and/or scattered light, shape, size thickness and fractal properties. Spectroscopic signals include but are not limited to Raman spectroscopy, absorption spectroscopy, fluorescence correlation spectroscopy, NMR spectroscopy, quasi-elastic light-scattering spectroscopy, circular dichroism spectroscopy and Fourier transform spectroscopy and broadband spectroscopic (also known as hyperspectral imaging). These methods can be applied to detect protein deposits measured in the differing layers of the retina and/or in blood vessels. The beam used for the spectroscopy could be but is not limited to the same beam as used to image in CSLO or UHROCT. The spectroscopic signal interrogated must be one that is not absorbed either by the water in the eye or by pigments in the elderly crystalline lens and should be returning from the retina, Spectroscopy as described in the foregoing can also be used to specify the structure and shape of the protein deposits imaged but also cross referenced with known spectroscopic signatures of pure proteins, of protein deposits found in post-mortem retinas or the signatures of proteins associated with different neurodegenerative diseases. Differentiation in different neurodegenerative diseases can be enhanced by machine learning or other artificial intelligence methods.

A third possible marker to differentiate different types of protein deposits or protein deposits present in different diseases or conditions is polarization imaging (Step 1b of FIG. 4) could be used with CSLO or UHROCT imaging or combined with any of the other marker techniques mentioned above and the fourth marker (light scattering) described below. The protein deposits would then be visible via differential absorption, scattering or reflection of polarized light (including potentially optical activity), or by polarization spectroscopy or by differential reflection of polarised light from the protein deposits in comparison with the retina without protein deposits. It is expected that the deposits themselves will interact with polarized light due to their fibrillar nature, and as oart of this intellectual property, the inventors have shown that this interaction differs for different types of pure protein deposit and also differs for deposits found in different parts of the retina, even when they are thought to be composed of the same protein. But they are presumed because of their location to be associated with different retinal diseases or conditions. In addition, an optically active dye that enhances the interaction of fibrillar deposits similar to but not restricted to Congo red, may be used. Identifying the interactions with polarized light of the amyloid deposits found in the different conditions, may include characterizing one or more of the Jones matrix or Mueller matrix components across the retina or performing a polarization imaging method known to enhance the contrast of structures with differing polarization properties (e.g., confocal scanning laser ophthalmoscopy improved using Mueller matrix polarimetry) or detecting structures because they have differing effects on a polarization property of the light. Depth resolved polarization OCT could also be used. Polarization imaging as described in the foregoing could also be used to characterize the deposits and to specify the structure and shape of the deposit, including its fractal nature or the multifractal spectra that results from the image (either directly taken or an interaction with polarized light.

A fourth possible marker s the light scattering characteristics and differing intrinsic properties of the protein deposits, including the following. The protein deposits may be visible as a deformation of the retinal surface which causes scattered light, visible in any of the techniques mentioned above or as an area of differing optical path length, made visible with techniques like optical coherence tomography or in confocal scanning laser ophthalmoscopy with the use of an indirect aperture, whose effect is to preferentially collect scattered light. In order for a CSLO to detect light scattered from the retinal vitreal surface, an indirect confocal aperture could be used while focusing the instrument anterior to the retinal vitreal interface.

In techniques such as OCT which measure optical path difference, it is important to resolve an optical path difference that is small, potentially one to several microns (often less than 10 microns). This is because protein deposits in the retina generally have their smallest dimension (thickness) perpendicular to the retinal surface. Thus, the depth resolution required for any of the imaging modalities mentioned above has to be excellent if path optical differences intrinsic protein deposits and potentially differing between them, are to be imaged as markers, either measuring intrinsic fluorescence or optical path differences in the protein deposits compared with the surrounding retina. And ultra high-resolution optical coherence tomography (UHR OCT) scan could include the retinal vitreal interface in order to assess the presence of deformation or optical path differences due to protein deposits close to the surface. The scan of the OCT would need to be denser in order to specify the structure and shape of the deposits.

Similar caveats apply as in the preceding paragraph if an optical technique is being used to locate protein deposits in the retinal vessels. For example, techniques such as OCT which measure optical path difference, it is important to resolve an optical path difference that is small, potentially one to several microns (often less than 10 microns). This is because protein deposits in the retinal vessels in anything before severe stages of cerebral amyloid angiopathy are most often confined to between the vessel walls and thus have small dimension (thickness) perpendicular to the retinal surface.

Other optical techniques may be used to assess whether the surface of the inner limiting membrane has been deformed by a protein deposit. Some of these assess the specular nature of the reflection from the inner limiting membrane and may be used to assess changes in normal age matched subjects and those with protein deposits at or near the retinal surface (inner limiting membrane) in association to neurodegenerative diseases. Other methods which measure the size of particles between approximately one and a few microns via scattered light may also be used as the presence of each deposit or cluster of deposits should create differential scattered light. These methods include the polarization methods described above. Any of the light scattering characteristics or differing intrinsic optical properties of a protein deposit or assessment of the deformation of the inner limiting membrane described in the foregoing could be used in order to specify the structure and shape of a protein deposit.

It is also advantageous to choose and modify the imaging modality to give the needed resolution and coverage of the retina. In addition, it would be reasonable, when initially identifying some conditions, to initially image a marker of a given protein in lower resolution imaging conditions in which the protein can be detected but not resolved into individual deposits.

More particularly, methods of imaging for the first step in imaging a larger area of the retina at the correct depth and include, but are not limited to, flood illumination of the retina incorporating optical methods to limit the depth of field (that is the thickness and/or the location of the retina imaged) possibly but not limited to a stereoscopic method. Confocal scanning laser ophthalmoscopy with or without depth resolution improved through a confocal pinhole and/or adaptive optics correction can provide up to 20 microns of resolution. If just a confocal pinhole or a detector without pinhole were used, without adaptive optics, then an imaging plane just anterior to the surface of the inner limiting membrane should be chosen so that the poorer depth resolution would still allow the separation of imaging signals from proteins, including amyloid beta in the anterior layers from those in posterior layers. Both flood illumination and confocal scanning laser ophthalmoscopy (CSLO) have the advantage of full coverage of the retina en face, with the proviso that the scanners for CSLO should ideally have a continuous movement or the steps should be no larger than the calculated size of the point spread function on the retina, so that light signals from sparse deposits will still be seen and enough deposits will be seen to categorize the severity of the disease associated with said proteins.

Optical coherence tomography can also be used to construct an en face image of the retina. In an adaptive optics corrected SLO or CSLO (AOSLO), given a realistic scanner resolution or when producing en face OCT images, the need for full surface coverage implies imaging fields which are 5 degrees by 5 degrees (25 degrees square) which in AOSLO by way of example could be scanned over the area of interest in increments of 25 square degrees, giving up to 400 fields to image a total of 1 up to 10,000 square degrees. The choice of imaging area would be modified as more data is collected on the prevalence of given protein deposits in different conditions and as a function of condition severity. Experience gained by Campbell's group in imaging retinal deposits of amyloid in Alzheimer's disease and cerebral amyloid angiopathy, particularly early in the conditions has shown that these deposits are sparse and widely separated. Thus, methods for retinal imaging of protein deposits in the retina in neurodegenerative conditions of the retina and brain used should produce full coverage over a large retinal area so as not to miss sparse deposits.

If the CSLO were not adaptive optics corrected, moderate field sizes with full coverage, of by example, 40 degrees by 40 degrees would allow complete coverage of small, sparse deposits (100 square degrees), allowing a much more rapid scanning of the up to 100,000 square degree area of interest in ~6 fields stitched together. Smaller fields of view could be used as for adaptive optics corrected imaging in the same manner as described above.

Ultra high-resolution optical coherence tomography (UHROCT) with a light source with sufficient bandwidth to give the needed retinal depth resolution is also a candidate for the initial field imaging and would be focused on the anterior layers of the retina. Again, it is important that full en face coverage of the retina be achieved. Continuous scanners give full coverage. In choosing the spacing of adjacent line scans in the usual B scan configuration, the line spacing should be about 10 microns so as approximately match the point spread on the retina. The depth of the scan needed is only about 50 microns from the retinal surface so the A scan depth should be limited to give faster scanning. Again, given usual digital resolutions, if the UHROCT is not AO corrected for the initial wide field imaging, the scan should be a minimum of 5×5 degrees and up to 10 degrees by 10 degrees. However, this OCT scan will take much longer than the time for the CSLO scan above given the need for an initial A (or depth) scan in the more frequently used OCT instruments.

From the above description, it can be seen that a newer OCT scanning protocol that scans either a line in depth or an initial en face image in-depth would be advantageous in speed in imaging the needed volumes of the retina with the needed full coverage and resolution discussed above, so as to image sparse protein deposits.

A combination in the first step of the faster non adaptive optics corrected CSLO scan to identify a marker of $A\beta$ followed by the use of adaptive optics corrected SLO, an offset SLO scan, a stereoscopic imaging technique or an OCT scan, any of which give improved depth resolution for the areas in which the marker in an initial image is evident but with less depth resolution, is also advantageous. The restricted areas and depth of subsequent imaging will save time but the better depth resolution will confirm that the marker of the protein is coming from a retinal layer or a retinal feature associated with a particular disease or condition.

Two photon fluorescence imaging of a marker of $A\beta$ would have the required depth resolution of the anterior retinal layers. Imaging of an intrinsic fluorescent marker would require too many frames and time to get resolution and sufficient signal over a large area. If an extrinsic fluorescent marker with a large cross section and brightness and without toxicity were available for $A\beta$, this imaging would be feasible. The preference would be for a marker excited in the infrared. Then the delivery light could potentially be the same in the CSLO wide field imaging channel and the two-photon excitation channel, simplifying instrument design.

The required depth resolution is likely less than 50 microns. Other imaging techniques such as ultra high-resolution ultrasound, photo-acoustics or PET would also be possible if the needed depth resolution of the living retina could be demonstrated.

The method of imaging the larger area of the retina may be combined with a marker of the presence of amyloid protein deposits. In this case, the retina can be imaged at lower resolutions, which may be used to speed up the coverage of the complete retina. A first possible marker includes fluorescent molecules which are non toxic to humans which include, but are not limited to curcumin. Following initial location of amyloid deposits at low magnification, the system can zoom to a larger magnification to characterize the deposits.

Preferred Implementation

Numerous optical imaging methods could be used from which key properties could be derived. These properties include, but are not limited to, polarimetric properties, multifractal spectral and or fractal properties, and dimensional properties. Other properties derived from other optical imaging modalities could also be used in the classifications described herein.

In demonstrating the feasibility of the methods above for separating AD from AMD and severity of AD, the inventors' preferred implementation uses a full polarimeter combined with a wide-angle scanning laser ophthalmoscope with relatively high lateral resolution (a maximum of 10-15 microns) (see FIG. 22). Referring to FIG. 22, The references numbers are defined as follows: 1 is a low coherence laser source, 2 and 3 are collimating lenses, 4 and 5 are a polarized light state generator, in this configuration shown as a linear polarizer (4) followed by a rotatable quarter wave plate (5), 14 is a beam splitter separating the input and output channels, 6 is a mirror, 7 and 8 are lenses forming a telescope, 9 is the eye being examined, 10 is a mirror which reflects the illumination wavelength and transmits the wavelength illuminating the fixation target, 11 is a mirror that reflects light from 13 while an image is being acquired and is moved out of the path to allow fixation, 12 collimates the light from 13 to give a fixation target, 14 is a beam splitter, transmitting the light returning from the eye, 15 and 16 are a polarized light state analyser where 15 is a rotatable quarter wave plate and 16 is a linear polarizer. 17 is an aperture stop, 18 is a focussing lens, 19 is an aperture, and 20 is a light detector.

From the resulting 16 raw images, the polarimetric properties were derived. The derived linear retardance map is used to calculate the fractal properties and dimensional properties. However, any established imaging method could be used to generate polarimetric properties, including but not limited to incomplete polarimetry, second or third harmonic generation polarimetry, polarimetric optical coherence tomography or any other known method. For the dimensional and fractal properties, any imaging method, optical or otherwise can be used. Once the properties likely to contribute most to the classification being considered are determined, an incomplete polarimeter could be combined with any other fundus imaging instrument. Fractal properties and dimensional properties could be derived from any of the raw images taken in the polarimetric measurement or any calculated polarimetric property.

The full description also describes how to refine the classification of retinal deposits into groups from imaging methods applied to the living eye where the sub-population of individuals being imaged are chosen because they are well characterized and likely contain a predominance of deposits due to one of the conditions or levels of severities above.

The classification methods referred to herein that resulted in high accuracies of classification are preferred. However, these also teach that attempting several classification approaches with several subsets of variables is the best approach as it is then possible to choose the combination that works best for the given classification.

Finally, the analysis above classifies into one of two classes. These classifications will be useful as background, but classifications can be made into multiple categories from a single set of measured properties (a complete or subset of those outlined above) using a branching tree and as a starting point, properties that are known to classify a single condition or severity from another condition(s) and severities described. In this case, a classification method like Random Forrest or any other method of classification (statistical, machine learning, convolutional neural network or AI) which specifies the importance of specific properties to the classification will be useful in generalizing from a classification of two classes to multiple classes.

The specific properties described in many of the examples sited above (polarimetric, multifractal spectral and dimensional), have been measured in the embodiment of the system of FIG. 22 described above for imaging the interaction of the tissue (including amyloid deposits) with polarized light via a spatially resolved Mueller matrix derived from initial imaging at multiple settings of a polarization state generator and polarization state analyser. Polarimetric properties representing interactions with polarized light are then calculated and from these matrices. In turn multifractal spectral analysis giving multifractal properties can be calculated on any deposits with sufficient contrast in any "image" where a deposit displays contrast because its interaction with polarised light differs from that of the surrounding tissue. The inventors' preferred implementation is to calculate the multifractal spectral properties on an image of linear retardance across the deposit and its immediate surround.

Therefore what is claimed is:

1. A method for detecting, imaging, differentiating and classifying proteins or protein deposits in the retina of the eye for detecting neurodegenerative diseases of the retina and/or of the brain or their prodromal stages, comprising the steps of:
   a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;
   b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and
   c) differentiating and classifying the markers detected at each position in the retina by using their measured morphology, including size, shape, fractal properties of the proteins or protein deposits, or characterizing a strength of a marker(s) of protein or protein deposits or strength of signal(s) coming from any interaction with light, separately for each protein(s) or protein deposit(s) so as to determine if the properties including position and morphology, markers and or interaction with light, of said protein(s) or protein deposit(s) are consistent with said protein(s) or protein deposit(s) found in a particular disease or condition which occurs in either the retina or the brain or both where properties of protein(s) and or protein deposit(s) consistent with a particular disease or condition have been determined from ex vivo tissue of those with said disease or condition, from animal models or from previous measurements of those with known conditions.

2. The method according to claim 1, wherein said steps of differentiating and classifying the markers is performed using a machine learning algorithm including entering into the algorithm one or more details of morphology, including size, shape, density, area, structure and form of the protein(s) and protein deposit(s), including their fractal properties; or a strength of a marker(s) of protein(s) or protein deposit(s) or strength of signal(s) coming from any interaction of the markers with the light illuminating the retina, including interactions of the protein deposit(s) with polarized light and outputs of the machine learning algorithm include the protein(s) or protein deposit(s) categorized into one of 2 or more categories, the individual properties most important to the categorization of the protein(s) or protein deposit(s), the accuracy with which the deposits have been correctly categorized if their true category is known and the input parameters with the most influence on the categorization.

3. The method according to claim 2, wherein said machine algorithm is any one of random Forrest (R.F), supporting vector machine (SVM) non-parametric discriminant analysis, including linear discriminant analysis (LDA) or Convolutional neural networks (CNN).

4. The method according to claim 1, including correlating the size, shape, morphology, numbers, density of or strength of any marker of protein(s) or protein deposit(s) or strength of signal(s) coming from any interaction with light, thereof to diagnose one or more neurodegenerative disease(s) or condition(s) of the brain or eye, a prodromal stage of said disease or condition or pathological changes associated with said disease(s) or condition(s).

5. The method according to claim 1, where at least one of said disease(s) or condition(s) are not normally considered to be neurodegenerative diseases or conditions.

6. The method according to claim 1, including using including correlating the size, shape, morphology, numbers, density of or strength of any marker of protein(s) or protein deposit(s) or strength of signal(s) coming from any interaction with light thereof to classify the severity or stage of said condition(s) or disease(s) of the eye or brain.

7. The method according to claim 6 where at least one of said disease(s) or condition(s) are not normally considered to be a neurodegenerative disease or condition.

8. The method according to claim 6 including correlating the size, shape, morphology, numbers, density of or strength of any marker of protein(s) or protein deposit(s) or strength of signal(s) coming from any interaction with light thereof to diagnose a least one or more sub type of one or more neurodegenerative disease(s) or condition(s) of the brain or eye, a prodromal stage of said disease(s) or condition(s) or pathological changes associated with a sub type or sub types of said disease(s) or condition(s).

9. The method according to claim 1, including using longitudinal change in any combination of the size, shape, morphology, numbers, density of or strength of any marker of protein(s) or protein deposit(s) or strength of signal(s) coming from any interaction with light to determine the progression of the disease process associated with one or more of the neurodegenerative diseases of the eye and brain between two or more time points.

10. The method according to claim 1, wherein said step a) of performing large field imaging includes obtaining one or more images from humans extending at least 140 degrees along a horizontal, which is +70 degrees nasal and temporal to the human's optic nerve head along the horizontal, with imaging of 70 degrees in the vertical which is +40 degrees to the horizontal.

11. The method according to claim 1, wherein said step a) of performing large field imaging includes flood illumination of the retina.

12. The method of claim 11 including limiting a depth of field of the retina being imaged.

13. The method according to claim 1, wherein said step a) of performing large field imaging includes obtaining the image of the location close to, or on, the anterior Surface using scanning laser ophthalmoscopy (SLO) with a detector of limited area such that the depth of field is limited by the detector area, comprising the steps of imaging the location close to, or on, the anterior Surface at a plane just anterior to the Surface of the inner limiting membrane Such that a depth resolution allows separation of imaging signals from the proteins or protein deposits in anterior layers from those in posterior layers of the retina; and Scanning continuously or in steps which are no larger than a calculated size of a point spread function on the retina such that there are no gaps in the enface area of the retina Scanned and imaged so that light from sparse deposits is observable.

14. A method for detecting, imaging, differentiating and classifying proteins or protein deposits in the retina of the eye for detecting neurodegenerative diseases of the retina and/or of the brain or their prodromal stages, comprising the steps of:
  a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;
  b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and
  c) differentiating and classifying the markers detected at each position in the retina by using the properties of the protein(s) or protein deposit(s) of the morphology, including size, shape, and fractal properties of the protein(s) or protein deposit(s) or characterizing a strength of a marker(s) of protein(s) or protein deposit(s) or strength of any measured signal(s) coming from any interaction with light so as to determine if the proteins or protein deposits belong to a class known as amyloid or thioflavin positive deposits which would stain with thioflavin and fluoresce or are proteins or protein deposits which would not stain with thioflavin and would not fluoresce known as thioflavin negative deposits, where said classification compares with results previously obtained in ex vivo tissue where the combination of properties, known as markers, corresponding to a thioflavin positive deposit; has been determined using thioflavin staining as a gold standard.

15. The method according to claim 14, further comprising the steps of:
  d) differentiating and classifying the markers detected at each position in the retina by using their measured morphology, including size, shape, fractal properties of the proteins or protein deposits, or characterizing a strength of a marker(s) of protein or protein deposits or strength of signal(s) coming from any interaction with light, separately for the subset of thioflavin positive deposits, known as amyloids and for the subset of thioflavin negative deposits, or for all deposit(s) together, so as to determine if the properties including position and morphology, markers and or interaction with light, of said protein(s) or protein deposit(s) are consistent with said protein(s) or protein deposit(s) found in a particular disease or condition which occurs in either the retina or the brain or both where properties of protein(s) and or protein deposit(s) consistent with a particular disease or condition have been determined from ex vivo tissue of those with said disease or condition, from animal models or from previous measurements of those with known conditions; and
  e) differentiating and classifying the markers detected at each position in the retina by using their measured morphology, including size, shape, fractal properties of the proteins or protein deposits, or characterizing a strength of a marker(s) of protein(s) or protein deposit(s) or strength of signal(s) coming from any interaction with light for each protein type associated with each identified neurodegenerative disease, and compare to those properties previously identified as markers of severity of the given neurodegenerative disease including one or more of protein deposit numbers, total area of the retina covered by protein deposits, volume or thickness of protein deposits, strength of signal(s) coming from any interaction of proteins or protein deposits with light, morphology of deposits known to change with severity, particular locations of protein deposits in the retina and deduce the severity of the disease in the retinal and by inference its severity in the brain.

16. The method according to claim 14, further comprising the steps of:
   d) differentiating and classifying the markers detected at each position in the retina by using their measured morphology, including size, shape, fractal properties of the proteins or protein deposits, or characterizing a strength of a marker(s) of protein(s) or protein deposit(s) or strength of signal(s) coming from any interaction with light separately for the subset of thioflavin positive deposits, known as amyloids and for the subset of thioflavin negative deposits, or for all deposit(s) together so as to determine if the areas detected contain a particular protein type, determined more precisely than the class determined in step c), where the properties measured are compared with the properties previously determined for pure proteins or pure protein deposits; and
   e) differentiating and classifying the markers detected at each position in the retina by using their measured morphology, including size, shape, fractal properties of the proteins or protein deposits, or characterizing a strength of a marker(s) of protein(s) or protein deposit(s) or strength of signal(s) coming from any interaction with light for each protein type and compare to those properties previously identified as markers of severity of a given neurodegenerative disease including one or more of protein deposit numbers, total area of the retina covered by protein deposits, volume or thickness of protein deposits, strength of signal(s) coming from any interaction of proteins or protein deposits with light, morphology of deposits known to change with severity, particular locations of protein deposits in the retina and deduce the severity of the disease in the retinal and by inference its severity in the brain.

17. The method according to claim 16,
   wherein said each protein type in the step e) is associated with each identified neurodegenerative disease, and prior to the step e), the method further comprises the step of:
   differentiating and classifying the markers detected at each position in the retina by using their measured morphology, including size, shape, fractal properties of the proteins or protein deposits, or characterizing a strength of a marker(s) of protein or protein deposits or strength of signal(s) coming from any interaction with light, separately for each protein(s) or protein deposit(s) that has been identified as being or containing a given protein(s), so as to determine if the properties including position and morphology, markers and/or interaction with light of said protein(s) or protein deposit(s) are consistent with said protein(s) or protein deposit(s) found in a particular disease or condition which occurs in either the retina or the brain or both where properties of protein(s) and or protein deposit(s) consistent with a particular disease or condition have been determined from ex vivo tissue of those with said disease or condition, from animal models or from previous measurements of those with known conditions.

18. The method according to claim 17, including magnifying one area and making the differentiation and classification in any order and including or excluding one or more of the steps.

19. A method for detecting, imaging, differentiating and classifying proteins or protein deposits in the retina of the eye for detecting neurodegenerative diseases of the retina and/or of the brain or their prodromal stages, comprising the steps of:
   a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;
   b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and
   c) differentiating and classifying the markers detected at each position in the retina by using their measured morphology, including size, shape, fractal properties of the proteins or protein deposits; or characterizing a strength of a marker(s) of protein(s) or protein deposit(s) or strength of signal(s) coming from any interaction with light so as to determine if the areas detected contain a particular protein type, where the properties measured are compared with the properties previously determined for pure proteins or pure protein deposits.

20. The method according to claim 19, further comprising the steps of:
   d) differentiating and classifying the markers detected at each position in the retina by using their measured morphology, including size, shape, fractal properties of the proteins or protein deposits, or characterizing a strength of a marker(s) of protein or protein deposits or strength of signal(s) coming from any interaction with light, separately for each protein(s) or protein deposit(s) that has been identified as being or containing a given protein(s), so as to determine if the properties including position and morphology, markers and or interaction with light, of said protein(s) or protein deposit(s) are consistent with said protein(s) or protein deposit(s) found in a particular disease or condition which occurs in either the retina or the brain or both where properties of protein(s) and or protein deposit(s) consistent with a particular disease or condition have been determined from ex vivo tissue of those with said disease or condition, from animal models or from previous measurements of those with known conditions; and
   e) differentiating and classifying the markers detected at each position in the retina by using their measured morphology, including size, shape, fractal properties of the proteins or protein deposits, or characterizing a strength of a marker(s) of protein(s) or protein deposit(s) or strength of signal(s) coming from any interaction with light for each protein type associated with each identified neurodegenerative disease, and compare to those properties previously identified as markers of severity of the given neurodegenerative disease including one or more of protein deposit numbers, total area of the retina covered by protein deposits, volume or thickness of protein deposits, strength of signal(s) coming from any interaction of proteins or protein deposits with light, morphology of deposits known to change with severity, particular locations of protein deposits in the retina and deduce the severity of the disease in the retinal and by inference its severity in the brain.

21. A method for detecting, imaging, differentiating and classifying proteins or protein deposits in the retina of the eye for detecting neurodegenerative diseases of the retina and/or of the brain or their prodromal stages, comprising the steps of:
   a) performing wide field imaging of the retina using light to illuminate the retina with sufficient field size, depth imaged and lateral resolution to give full coverage of the en face portion of the retina for detecting for one or more markers of protein(s) or protein deposit(s) associated with neurodegenerative diseases of the retina and/or brain as a function of position in the retina during the wide field imaging of the retina;
   b) if one or more areas presents markers of one or more proteins or protein deposits, then if needed, magnifying and increasing the resolution of the one or more areas and characterizing a morphology, including size, shape, fractal properties, of the one or more areas of protein or protein deposits, or characterizing a strength of a marker(s) of protein(s) or protein deposit(s) or strength of signal(s) coming from any interaction of the markers with the light illuminating the retina; and
   c) differentiating and classifying the markers detected at each position in the retina by using their measured morphology, including size, shape, fractal properties of the proteins or protein deposits; or characterizing a strength of a marker(s) of protein(s) or protein deposit(s) or strength of signal(s) coming from any interaction with light for each protein type associated with a neurodegenerative disease where said neurodegenerative disease diagnosis is already known, or the identity of disease and its severity can be deduced simultaneously from the properties measured and compare to those properties previously identified as markers of severity of the given neurodegenerative disease including one or more of protein deposit numbers, total area of the retina covered by protein deposits, volume or thickness of protein deposits, strength of signal(s) coming from any interaction of proteins or protein deposits with light, morphology of deposits known to change with severity, particular locations of protein deposits in the retina and deduce the severity of the disease in the retinal and by inference its severity in the brain.

* * * * *